United States Patent
Deadman et al.

(10) Patent No.: US 8,318,732 B2
(45) Date of Patent: *Nov. 27, 2012

(54) COMPOUNDS HAVING ANTIVIRAL PROPERTIES

(75) Inventors: John Joseph Deadman, Carlton (AU); Eric Dale Jones, Bentleigh East (AU); David Ian Rhodes, Heidelberg Heights (AU); Nicholas Andrew Van de Graff, Prahran (AU)

(73) Assignee: Avexa Limited, Richmond (Victoria) (AU)

( * ) Notice: Subject to any disclaimer, the term of this patent is extended or adjusted under 35 U.S.C. 154(b) by 142 days.

This patent is subject to a terminal disclaimer.

(21) Appl. No.: 12/734,036

(22) PCT Filed: Jul. 2, 2009

(86) PCT No.: PCT/AU2009/000858
§ 371 (c)(1),
(2), (4) Date: Oct. 20, 2010

(87) PCT Pub. No.: WO2010/000032
PCT Pub. Date: Jan. 7, 2010

(65) Prior Publication Data
US 2011/0039842 A1 Feb. 17, 2011

Related U.S. Application Data

(60) Provisional application No. 61/161,931, filed on Mar. 20, 2009.

(30) Foreign Application Priority Data

Jul. 2, 2008 (AU) .................. 2008903407

(51) Int. Cl.
*A61K 31/5355* (2006.01)
*A61K 31/519* (2006.01)
*A61P 31/18* (2006.01)
*A61P 31/14* (2006.01)
*C07D 471/04* (2006.01)

(52) U.S. Cl. .............. 514/233.2; 514/259.41; 544/116; 544/282

(58) Field of Classification Search .................... None
See application file for complete search history.

(56) References Cited

U.S. PATENT DOCUMENTS
2004/0229909 A1  11/2004  Kiyama et al.
2005/0256109 A1  11/2005  Naidu

FOREIGN PATENT DOCUMENTS
WO  WO2008077188  *  3/2008
WO  2008/077188     7/2008

OTHER PUBLICATIONS

Behrend et al., caplus an 1907:9348.*

* cited by examiner

*Primary Examiner* — Sun Jae Loewe
(74) *Attorney, Agent, or Firm* — Fish & Richardson P.C.

(57) ABSTRACT

The present invention provides a compound of formula (I) or a pharmaceutically acceptable derivative, salt or prodrug thereof. The present invention further provides a method of treatment or prophylaxis of a viral infection in a subject comprising administering to said subject an effective amount of a compound of formula (I) or a pharmaceutically acceptable derivative, salt or prodrug thereof. Pharmaceutical compositions comprising a compound of formula (I) are also provided.

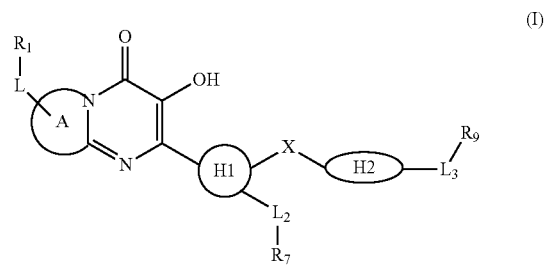

13 Claims, No Drawings

COMPOUNDS HAVING ANTIVIRAL PROPERTIES

CROSS REFERENCE TO PRIOR APPLICATIONS

This is a U.S. National Phase application under 35 U.S.C. §371 of International Patent Application No. PCT/AU2009/000858, filed Jul. 2, 2009, and claims the priority of Australian Patent Application No. 2008903407, filed Jul. 2, 2008 and U.S. Provisional Application Ser. No. 61/161,931, filed Mar. 20, 2009 all of which are incorporated by reference herein. The International Application published in English on Jan. 7, 2010 as WO 2010/000032 under PCT Article 21(2).

FIELD OF THE INVENTION

The present invention relates to a class of compounds useful in the treatment of viral infections, particularly HIV infections which show resistance to known HIV inhibitors.

BACKGROUND OF THE INVENTION

The retrovirus designated "human immunodeficiency virus" or "HIV" is the etiological agent of a complex disease that progressively destroys the immune system. This disease is known as acquired immune deficiency syndrome or AIDS. As at December 2005 an estimated 40 million people are living with HIV world wide and over 3 million deaths are occurring annually.

A feature of retrovirus replication includes the reverse transcription of the viral genome into proviral DNA and its integration into the host cell genome. These steps are required for HIV replication and are mediated by the virus encoded enzymes, reverse transcriptase and integrase respectively.

HIV infection follows a path of the virus particle binding to cell surface receptors and co-receptors resulting in fusion of the virus particle with the cell. The contents of the virus are released into the cytoplasm where reverse transcription of the HIV genome occurs. Through a series of steps a double stranded proviral DNA copy is produced. The proviral DNA is transported to the nucleus in a complex known as the pre integration complex (PIC) which contains integrase and other viral and possibly cellular proteins. Once inside the nucleus the proviral DNA is integrated into the host cell genome via the action of integrase. Once integrated, transcription and translation of the viral genome can occur resulting in the production of viral proteins and a new viral RNA genome. These proteins and genome assemble at the cell surface and, depending on cell type, possibly other intracellular membranous compartments. Assembled particles then bud out from the cell and during, or soon after, this process mature into infectious HIV particles through the action of the viral protease.

The integration of the proviral genome into the host cell genome requires the action of an integrase which carries out this process in at least three steps, possibly four. The first step involves the assembly of the viral genome into a stable nucleoprotein complex, secondly, processing of two nucleotides from the 3' termini of the genome to give staggered ends with free 3' OH residues and thirdly the transfer of these ends into the host cell genome. The final step involves the gap filling and repair of the insertion site in the host genome. There is still some conjecture over whether the integrase performs this final step or whether it is carried out by cellular repair enzymes.

Currently HIV infection can be treated with a number of inhibitors on the market which target reverse transcriptase, protease or entry into the cell. Treatment of HIV infection with these, or a combination of these, drugs is known to be an effective treatment for AIDS and similar diseases. Shortcomings with the current inhibitors include the rapid emergence and increase incidence of resistance and numerous side effects.

Certain mutations within the wild-type viral integrase enzyme are known to confer resistance to a number of known integration inhibitors published in the literature. In particular, the viral variants containing Q148H/G140S double mutation in integrase and the N155H/E92Q double mutation in integrase represent the two of the more common viruses identified that are failing treatment with Isentress (Raltegravir, MK-0518). The triple mutant Q148K/G140A/E138A is also resistant to Raltegravir. See: Kobayashi et al, Antiviral Research, received 17 Apr. 2008, accepted 17 Jun. 2008; and Vacca et al; Discovery of MK-2048—subtle changes confer unique resistance properties to a series of tricyclic hydroxy-pyrrole integrase strand transfer inhibitors; Abstract from the 4$^{th}$ IAS Conference on HIV Pathogenesis Treatment and Prevention; 22-25 Jul. 2007, Sydney, Australia.

The specifications of Australian Provisional Patent Application Nos. 2006907283, 2007902479, 2007903401 and 2007904114 and International Patent Application No PCT/AU2007/001980 which derives priority from these applications describe a broad class of compounds that inhibit HIV integrase activity. The present inventors have now determined that a sub-class of these compounds are surprisingly effective (when compared to other members of the class) against viral variants containing the Q148H/G140S double mutation in integrase and the N155H/E92Q double mutation in integrase. This sub-class of compounds also shows surprising activity against the triple mutant Q148K/G140A/E138A.

SUMMARY OF THE INVENTION

In a first aspect, the present invention provides a compound of Formula I or a pharmaceutically acceptable derivative, salt or prodrug thereof wherein:

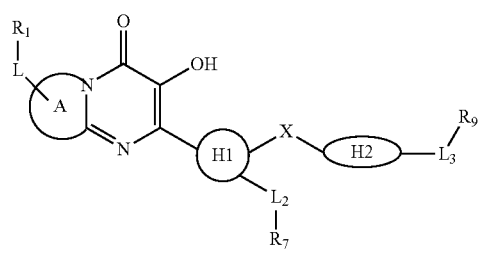

A is a six-membered aromatic or heteroaromatic moiety fused to the nitrogen-containing ring;

L-R$_1$ is 0-3 substituents wherein:
  each L is independently absent or is selected from the group consisting of Z, C$_{1-3}$alkylene, >C=Z, —CZ$_2$—, —C(=Z)C$_{1-3}$alkylene, —CZ$_2$—C$_{1-3}$alkylene, —C$_{1-3}$alkylene-C(=Z)—, —C$_{1-3}$alkylene-CZ$_2$— wherein each Z is independently selected from O, S, and NH;
  each R$_1$ is independently selected from the group consisting of hydrogen, C$_{1-10}$alkyl wherein one or more of the carbon atoms of the alkyl chain may optionally be replaced with oxygen atoms, C$_{1-10}$alkylNR$_3$R$_4$, halo, NR$_3$R$_4$, alkylaryl, S(O)NR$_3$R$_4$, SO$_2$NR$_3$R$_4$, SO$_2$C$_{1-}$ $_{10}$alkyl, and $C_{5-10}$cycloalkyl wherein one or more of the carbon atoms of the cycloalkyl ring are replaced with one or more oxygen atoms;

$R_3$ and $R_4$ are each independently selected from the group consisting of hydrogen, $C_{3-6}$cycloalkyl, $C_{1-10}$alkyl, $C_{1-10}NR_5R_6$, —(CO)(CO)$NR_5R_6$; or $R_3$ and $R_4$ taken together with the attached nitrogen form a 5-7 membered heterocyclic ring which contains zero to two additional heteroatoms selected from N, O or S where S can be at the S, S(O) or S(O)$_2$ oxidation state and wherein said heterocyclic ring is optionally substituted at the carbon or nitrogen atoms with one or more substituents selected from halo, $C_{1-4}$alkyl, $CO_2C_{1-4}$alkyl, $NR_5R_6$; $C_{1-4}$alkyl$NR_5R_6$ and further wherein one of the carbon atoms in the heterocyclic ring is optionally a carbonyl carbon;

$R_5$ and $R_6$ are each independently selected from the group consisting of H and $C_{1-4}$alkyl or $R_5$ and $R_6$ together with the attached nitrogen form a 5-7 membered heterocyclic ring which contains zero to two additional heteroatoms selected from N, O or S where S can be at the S, S(O) or S(O)$_2$ oxidation state and wherein said heterocyclic ring is optionally substituted at the carbon or nitrogen atoms with one or more substituents selected from halo and $C_{1-4}$alkyl;

when $R_1$ is alkylaryl, the aryl group of said alkylaryl substituent is optionally substituted with a substituent selected from $C_{1-10}$alkyl, —O—$C_{1-10}$alkyl, $C_{1-10}$alkylNRR$_3R_4$, —O—$C_{1-10}$alkylNR$_3R_4$, halo, $NR_3R_4$, alkylaryl, —O-alkylaryl, $SO_2NR_3R_4$;

$H_1$ is a 5- or 6-membered saturated, partially saturated or aromatic ring containing between 1 and 4 heteroatoms independently selected from the group consisting of N, O and S;

$L_2$-$R_7$ is 0-2 substituents wherein:
each $L_2$ is independently absent or is selected from the group consisting of Z, $C_{1-3}$alkylene, >C=Z, —CZ$_2$—, —C(=Z)$C_{1-3}$alkylene, —CZ$_2$—$C_{1-3}$alkylene, —$C_{1-3}$alkylene-C(=Z)—, —$C_{1-3}$alkylene-CZ$_2$— wherein each Z is independently selected from O, S, and NH;
each $R_7$ is independently selected from the group consisting of hydrogen, $C_{1-10}$alkyl wherein one or more of the carbon atoms of the alkyl chain may optionally be replaced with oxygen atoms, $C_{1-10}$alkyl$NR_3R_4$, halo, $NR_3R_4$, alkylaryl, S(O)$NR_3R_4$, $SO_2NR_3R_4$, $SO_2C_{1-10}$alkyl, and $C_{5-10}$cycloalkyl wherein one or more of the carbon atoms of the cycloalkyl ring are optionally replaced with one or more oxygen atoms;

X is $CR_8R_{8'}$
each of $R_8$ and $R_{8'}$ is independently selected from the group consisting of H and $CH_3$, preferably H;

$H_2$ is a 5- or 6-membered saturated, partially saturated or aromatic ring containing between 0 and 4 heteroatoms independently selected from the group consisting of N, O and S;

$L_3$-$R_9$ is 0-3 substituents wherein:
each $L_3$ is independently absent or is selected from the group consisting of Z, $C_{1-3}$alkylene, >C=Z, —CZ$_2$—, —C(=Z)$C_{1-3}$alkylene, —CZ$_2$—$C_{1-3}$alkylene, —$C_{1-3}$alkylene-C(=Z)—, —$C_{1-3}$alkylene-CZ$_2$— wherein each Z is independently selected from O, S, and NH;
each $R_9$ is independently selected from the group consisting of hydrogen, $C_{1-10}$alkyl wherein one or more of the carbon atoms of the alkyl chain may optionally be replaced with oxygen atoms, $C_{1-10}$alkyl$NR_3R_4$, halo, $NR_3R_4$, heterocyclyl, heteroaryl, alkylaryl, S(O)$NR_3R_4$, $SO_2NR_3R_4$, $SO_2C_{1-10}$alkyl, and $C_{5-10}$cycloalkyl wherein one or more of the carbon atoms of the cycloalkyl ring are optionally replaced with one or more oxygen atoms;
provided that at least one of L-$R_1$, $L_2$-$R_7$, and $L_3$-$R_9$ is present and is a heteroatom containing group.

In a second aspect, the present invention provides a method of treatment or prophylaxis of a viral infection in a subject comprising administering to said subject an effective amount of a compound of formula (I) or a pharmaceutically acceptable derivative, salt or prodrug thereof.

In a third aspect, there is provided the use of a compound of Formula I or a pharmaceutically acceptable derivative, salt or prodrug thereof in the preparation of a medicament for the treatment or prophylaxis of a viral infection in a subject.

In a fourth aspect, the present invention provides pharmaceutical composition comprising a compound according to the first aspect and a pharmaceutically acceptable carrier, diluent or excipient.

DETAILED DESCRIPTION OF THE INVENTION

In a first aspect, the present invention provides a compound of Formula I or a pharmaceutically acceptable derivative, salt or prodrug thereof wherein:

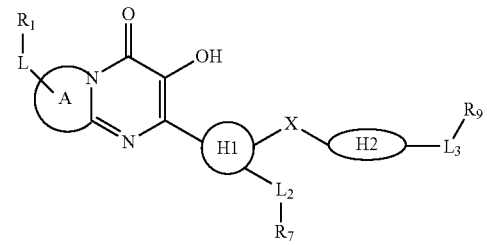

A is a six-membered aromatic or heteroaromatic moiety fused to the nitrogen-containing ring;
L-$R_1$ is 0-3 substituents wherein:
each L is independently absent or is selected from the group consisting of Z, $C_{1-3}$alkylene, >C=Z, —CZ$_2$—, —C(=Z)$C_{1-3}$alkylene, —CZ$_2$—$C_{1-3}$alkylene, —$C_{1-3}$alkylene-C(=Z)—, —$C_{1-3}$alkylene-CZ$_2$— wherein each Z is independently selected from O, S, and NH;
each $R_1$ is independently selected from the group consisting of hydrogen, $C_{1-10}$alkyl wherein one or more of the carbon atoms of the alkyl chain may optionally be replaced with oxygen atoms, $C_{1-10}$alkyl$NR_3R_4$, halo, $NR_3R_4$, alkylaryl, S(O)$NR_3R_4$, $SO_2NR_3R_4$, $SO_2C_{1-10}$alkyl, and $C_{5-10}$cycloalkyl wherein one or more of the carbon atoms of the cycloalkyl ring are replaced with one or more oxygen atoms;

$R_3$ and $R_4$ are each independently selected from the group consisting of hydrogen, $C_{3-6}$cycloalkyl, $C_{1-10}$alkyl, $C_{1-10}NR_5R_6$, —(CO)(CO)$NR_5R_6$; or $R_3$ and $R_4$ taken together with the attached nitrogen form a 5-7 membered heterocyclic ring which contains zero to two additional heteroatoms selected from N, O or S where S can be at the S, S(O) or S(O)$_2$ oxidation state and wherein said heterocyclic ring is optionally substituted at the carbon or nitrogen atoms with one or more substituents selected from halo, $C_{1-4}$alkyl, $CO_2C_{1-4}$alkyl, $NR_5R_6$; $C_{1-4}$alkyl$NR_5R_6$ and further wherein one of the carbon atoms in the heterocyclic ring is optionally a carbonyl carbon;

$R_5$ and $R_6$ are each independently selected from the group consisting of H and $C_{1-4}$alkyl or $R_5$ and $R_6$ together with the attached nitrogen form a 5-7 membered heterocyclic ring which contains zero to two additional heteroatoms selected from N, O or S where S can be at the S, S(O) or S(O)$_2$ oxidation state and wherein said heterocyclic ring is optionally substituted at the carbon or nitrogen atoms with one or more substituents selected from halo and $C_{1-4}$alkyl;

when $R_1$ is alkylaryl, the aryl group of said alkylaryl substituent is optionally substituted with a substituent selected from $C_{1-10}$alkyl, —O—$C_{1-10}$alkyl, $C_{1-10}$alkylNRR$_3$R$_4$, —O—$C_{1-10}$alkylNR$_3$R$_4$, halo, NR$_3$R$_4$, alkylaryl, —O-alkylaryl, SO$_2$NR$_3$R$_4$;

$H_1$ is a 5- or 6-membered saturated, partially saturated or aromatic ring containing between 1 and 4 heteroatoms independently selected from the group consisting of N, O and S;

$L_2$-$R_7$ is 0-2 substituents wherein:
each $L_2$ is independently absent or is selected from the group consisting of Z, $C_{1-3}$alkylene, >C═Z, —CZ$_2$—, —C(═Z)C$_{1-3}$alkylene, —CZ$_2$—C$_{1-3}$alkylene, —C$_{1-3}$alkylene-C(═Z)—, —C$_{1-3}$alkylene-CZ$_2$— wherein each Z is independently selected from O, S, and NH;
each $R_7$ is independently selected from the group consisting of hydrogen, $C_{1-10}$alkyl wherein one or more of the carbon atoms of the alkyl chain may optionally be replaced with oxygen atoms, $C_{1-10}$alkylNR$_3$R$_4$, halo, NR$_3$R$_4$, alkylaryl, S(O)NR$_3$R$_4$, SO$_2$NR$_3$R$_4$, SO$_2$C$_{1-10}$ alkyl, and $C_{5-10}$cycloalkyl wherein one or more of the carbon atoms of the cycloalkyl ring are optionally replaced with one or more oxygen atoms;

X is CR$_8$R$_{8'}$
each of R$_8$ and R$_{8'}$ is independently selected from the group consisting of H and CH$_3$, preferably H;

$H_2$ is a 5- or 6-membered saturated, partially saturated or aromatic ring containing between 0 and 4 heteroatoms independently selected from the group consisting of N, O and S;

$L_3$-$R_9$ is 0-3 substituents wherein:
each $L_3$ is independently absent or is selected from the group consisting of Z, $C_{1-3}$alkylene, >C═Z, —CZ$_2$—, —C(═Z)C$_{1-3}$alkylene, —CZ$_2$—C$_{1-3}$alkylene, —C$_{1-3}$alkylene-C(═Z)—, —C$_{1-3}$alkylene-CZ$_2$— wherein each Z is independently selected from O, S, and NH;
each $R_9$ is independently selected from the group consisting of hydrogen, $C_{1-10}$alkyl wherein one or more of the carbon atoms of the alkyl chain may optionally be replaced with oxygen atoms, $C_{1-10}$alkylNR$_3$R$_4$, halo, NR$_3$R$_4$, heterocyclyl, heteroaryl, alkylaryl, S(O)NR$_3$R$_4$, SO$_2$NR$_3$R$_4$, SO$_2$C$_{1-10}$alkyl, and $C_{5-10}$cycloalkyl wherein one or more of the carbon atoms of the cycloalkyl ring are optionally replaced with one or more oxygen atoms;

provided that at least one of L-R$_1$, L$_2$-R$_7$, and L$_3$-R$_9$ is present and is a heteroatom containing group.

In a preferred form, the compound of formula I is a compound of Formula II:

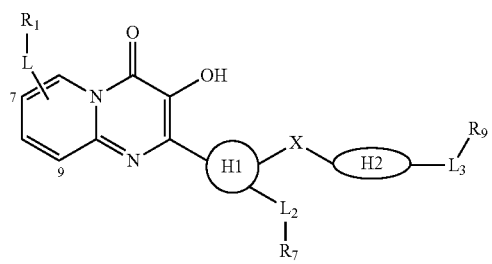

Preferably, LR$_1$ is morpholino.
Preferably, $H_1$ is a five membered aromatic heterocycle selected from the group consisting of thiazole, oxazole, oxadiazole, thiadiazole imidazole, triazole, and tetrazole.

In one embodiment, $H_1$ is selected from the group consisting of N-alkyl or N-aryl imidazole, N-alkyl or N-aryl triazole, and N-alkyl or N-aryl tetrazole.

In another embodiment, $H_1$ is selected from the group consisting of imidazole and thiazole.

Preferably, $H_2$ is phenyl.
Preferably, L$_2$-R$_7$ is absent.
Preferably, L$_3$-R$_9$ is at least 2 substituents wherein the first L$_3$-R$_9$ is halo and in the second L$_3$-R$_9$, L$_3$ is absent or is selected from >C═O and R$_9$ is selected from the group consisting of halo, NR$_3$R$_4$ and SO$_2$NR$_3$R$_4$.

Preferably, NR$_3$R$_4$ is morpholino, a five-membered cyclic sulphonamide (such as isothiazolidine) or a six membered cyclic sulphonamide.

Preferably, L-R$_1$ is at least 2 substituents wherein the first L-R$_1$ is halo and in the second L-R$_1$, L is absent or is selected from >C═O and R$_1$ is selected from the group consisting of halo, NR$_3$R$_4$ and SO$_2$NR$_3$R$_4$.

In one embodiment, L-R$_1$ consists of two substituents at positions 7 and 9.

In one embodiment, the heteroatom containing group of the proviso is selected from NR$_3$R$_4$ and SO$_2$NR$_3$R$_4$.

Preferably, the compound is selected from the group consisting of:

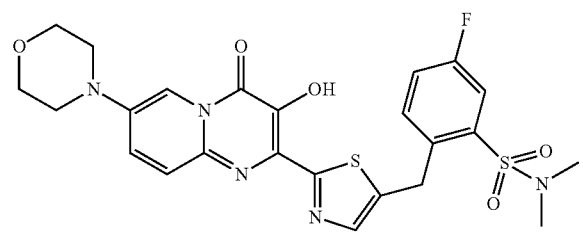

5-Fluoro-2-[2-(3-hydroxy-7-morpholin-4-yl-4-oxo-4H-pyrido[1,2-a]pyrimidin-2-yl)-thiazol-5-ylmethyl]-N,N-dimethyl-benzenesulfonamide

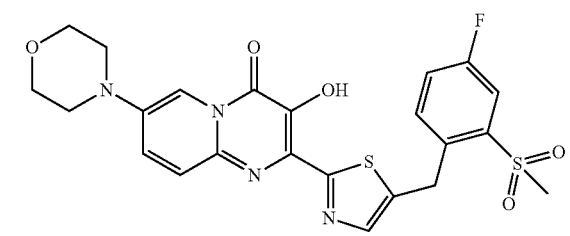

2-[5-(4-Fluoro-2-methanesulfonyl-benzyl)-thiazol-2-yl]-3-hydroxy-7-morpholin-4-yl-pyrido[1,2-a]pyrimidin-4-one

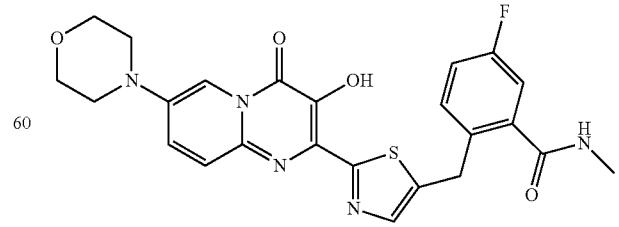

5-Fluoro-2-[2-(3-hydroxy-7-morpholin-4-yl-4-oxo-4H-pyrido[1,2-a]pyrimidin-2-yl)-thiazol-5-ylmethyl]-N-methyl-benzamide

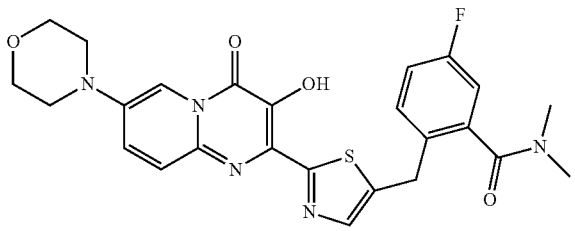

5-Fluoro-2-[2-(3-hydroxy-7-morpholin-4-yl-4-oxo-4H-pyrido[1,2-a]pyrimidin-2-yl)-thiazol-5-ylmethyl]-N-methyl-benzamide

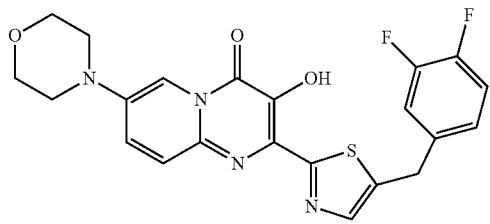

2-[5-(3,4-Difluoro-benzyl)-thiazol-2-yl]-3-hydroxy-7-morpholin-4-yl-pyrido[1,2-a]pyrimidin-4-one

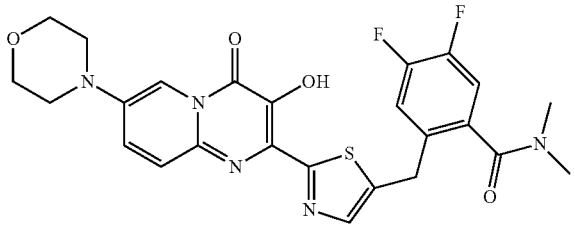

4,5-Difluoro-2-[2-(3-hydroxy-7-morpholin-4-yl-4-oxo-4H-pyrido[1,2-a]pyrimidin-2-yl)thiazol-5-ylmethyl]-N,N-dimethyl-benzamide

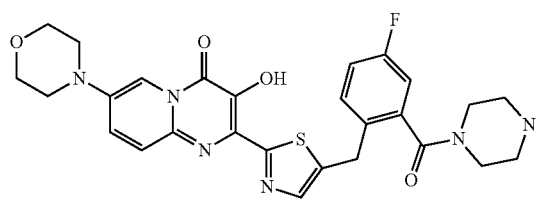

2-{5-[4-Fluoro-2-(4-methyl-piperazine-1-carbonyl)-benzyl]-thiazol-2-yl}-3-hydroxy-7-morpholin-4-yl-pyrido[1,2-a]pyrimidin-4-one

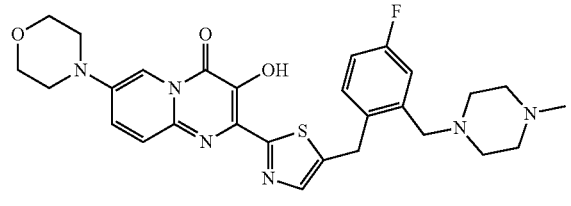

2-{5-[4-Fluoro-2-(4-methyl-piperazin-1-ylmethyl)-benzyl]-thiazol-2-yl}-3-hydroxy-7-morpholin-4-yl-pyrido[1,2-a]pyrimidin-4-one

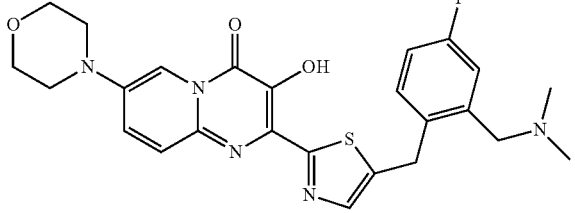

2-[5-(2-Dimethylaminomethyl-4-fluoro-benzyl)-thiazol-2-yl]-3-hydroxy-7-morpholin-4-yl-pyrido[1,2-a]pyrimidin-4-one

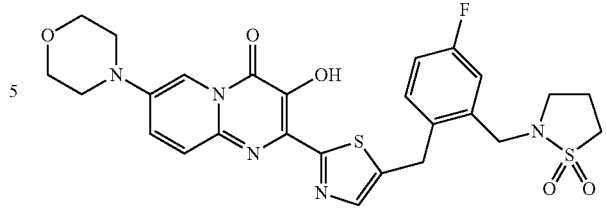

2-{5-[2-(1,1-Dioxo-1lambda*6*-isothiazolidin-2-ylmethyl]-thiazol-2-yl}-3-hydroxy-7-morpholin-4-yl-pyridol[1,2-a]pyrimidin-4-one

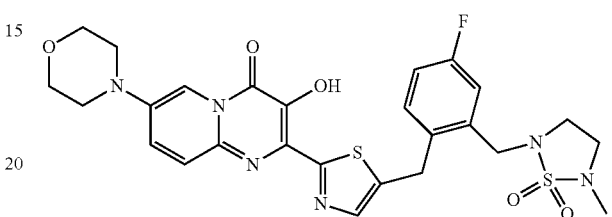

2-{5-[4-Fluoro-2-(5-methyl-1,1-dioxo-1lambda*6*[1,2,5]thiadiazolidin-2-yl)-benzyl]-thiazol-2-yl}-3-hydroxy-7-morpholin-4-yl-pyrido[1,2-a]pyrimidin-4-one

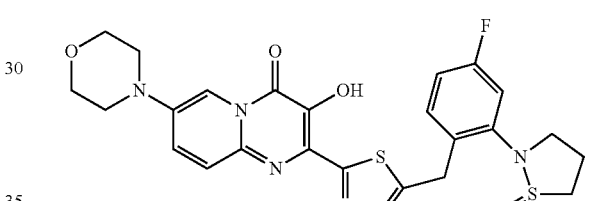

2-{5-[2(1,1-Dioxo-1lambda*6*isothiazolidin-2-yl)-4-fluoro-benzyl]thiazol-2-yl}-3-hydroxy-7-morpholin-4-yl-pyrido[1,2-a]pyrimidin-4-one

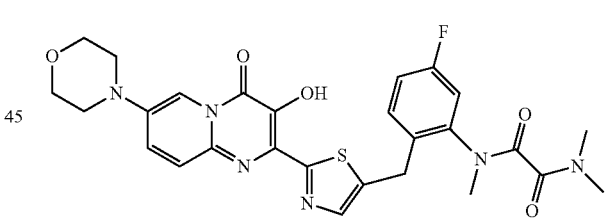

N-{5-Fluoro-2-[2-(3-hydroxy-7-morpholin-4-yl-4-oxo-4H-pyrido[1,2-a]pyrimidin-2-yl)-thiazol-5-ylmethyl]-phenyl}-N,N′,N′-trimethyl-oxalamide

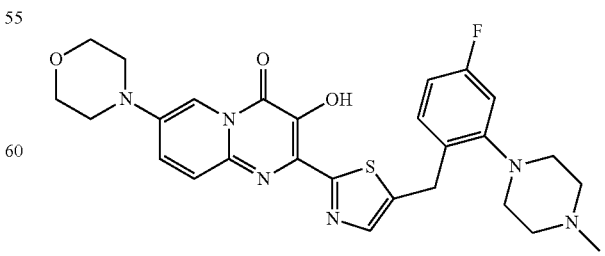

2-{5-[4-Fluoro-2-(4-methyl-piperazin-1-yl)-benzyl]-thiazol-2-yl}-3-hydroxy-7-morpholin-4-yl-pyrido[1,2-a]pyrimidin-4-one -continued

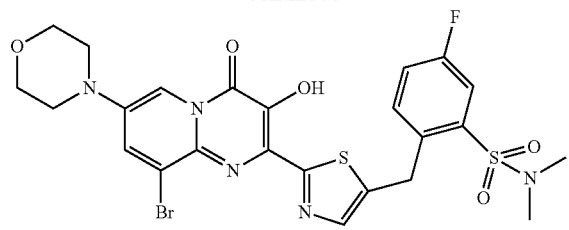

2-[2-(9-Bromo-3-hydroxy-7-morpholin-4-yl-4-oxo-4H-pyrido[1,2-a]pyrimidin-2-yl)-thiazol-5-ylmethyl]-5-fluoro-N,N-dimethyl-benzenesulfonamide

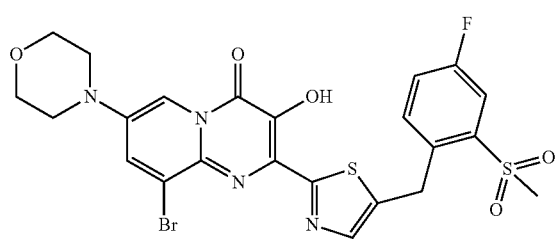

9-Bromo-2-[5-(4-fluoro-2-methanesulfonyl-benzyl)-thiazol-2-yl]-3-hydroxy-7-morpholin-4-yl-pyrido[1,2-a]pyrimidin-4-one

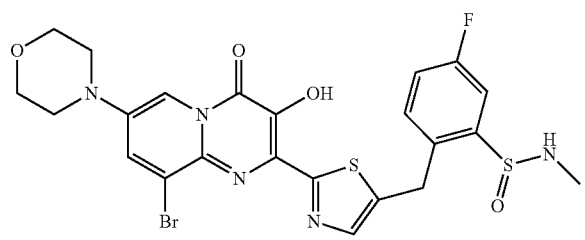

2-[2-(9-Bromo-3-hydroxy-7-morpholin-4-yl-4-oxo-4H-pyrido[1,2-a]pyrimidin-2-yl)-thiazol-5-ylmethyl]-5-fluoro-N-methyl-benzamide

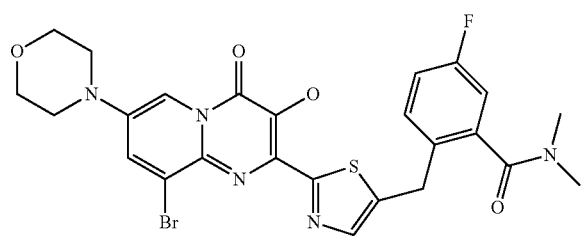

2-[2-(9-Bromo-3-hydroxy-7-morpholin-4-yl-4-oxo-4H-pyrido[1,2-a]pyrimidin-2-yl)-thiazol-5-ylmethyl]-5-fluoro-N,N-dimethyl-benzamide

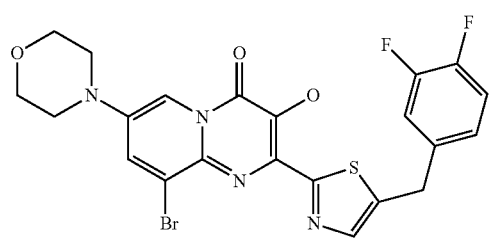

9-Bromo-2-[5-(3,4-difluoro-benzyl)-thiazol-2-yl]-3-hydroxy-7-morpholin-4-yl-pyrido[1,2-a]pyrimidin-4-one -continued

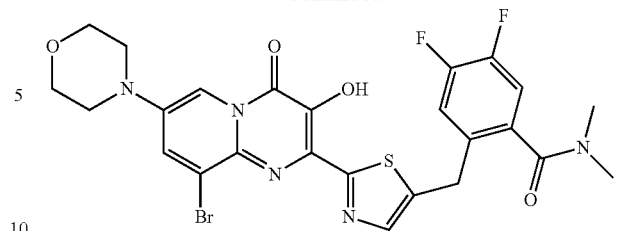

2-[2-(9-Bromo-3-hydroxy-7-morpholin-4-yl-4-oxo-4H-pyrido[1,2-a]pyrimidin-2-yl)-thiazol-5-ylmethyl]-4,5-difluoro-N,N-dimethyl-benzamide

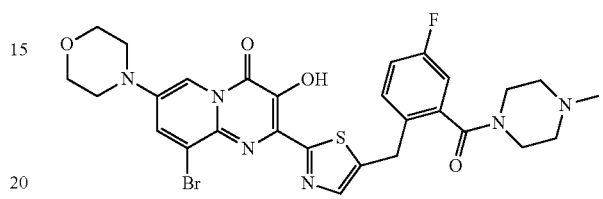

9-Bromo-2-{5-[4-fluoro-2-(4-methyl-piperazine-1-carbonyl)-benzyl]-thiazol-2-yl}-3-hydroxy-7-morpholin-4-yl-pyrido[1,2-a]pyrimidin-4-one

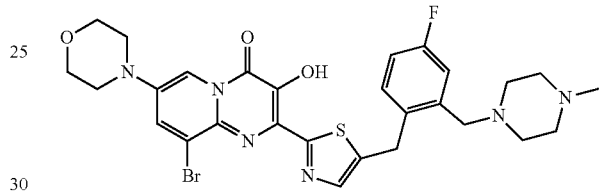

9-Bromo-2-{5-[4-fluoro-2-(4-methyl-piperazin-1-ylmethyl)-benzyl]-thiazol-2-yl}-3-hydroxy-7-morpholin-4-yl-pyrido[1,2-a]pyrimidin-4-one

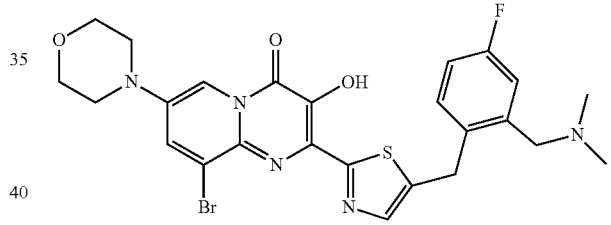

9-Bromo-2-[5-(2-dimethylaminomethyl-4-fluoro-benzyl)-thiazol-2-yl]-3-hydroxy-7-morpholin-4-yl-pyrido[1,2-a]pyrimidin-4-one

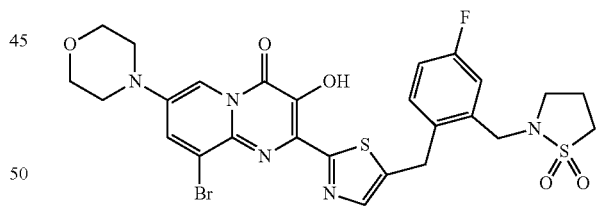

9-Bromo-2-{5-[2-{5-[2-(1,1-dioxo-1lambda*6*-isothiazolidin-2-ylmethyl)-4-fluoro-benzyl]-thiazol-2-yl}3-hydroxy-7-morpholin-4-yl-pyrido[1,2-a]pyrimidin-4-one

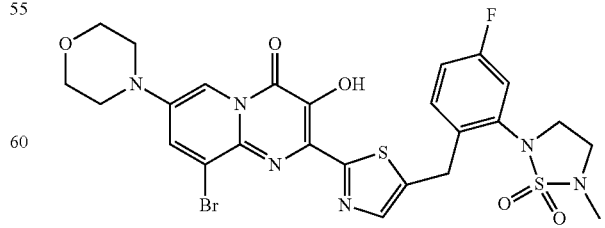

9-Bromo-2-{5-[4-fluoro-2-(5-methyl-1,1-dioxo-1lambda*6*-[1,2,5]thiadiazolidin-2-yl)-benzyl]-thiazol-2-yl}3-hydroxy-7-morpholin-4-yl-pyrido{1,2-a]pyrimidin-4-one

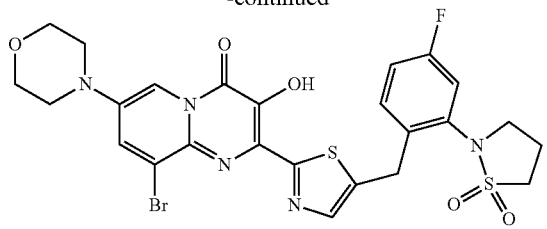

9-Bromo-2-{5-[ 2-(1,1-dioxo-1lambda*6*-isothiazolidin-2-yl)-4-fluoro-benzyl]-thiazol-2-yl}-3-hydroxy-7-morpholin-4-yl-pyrido{1,2-a]pyrimidin-4-one

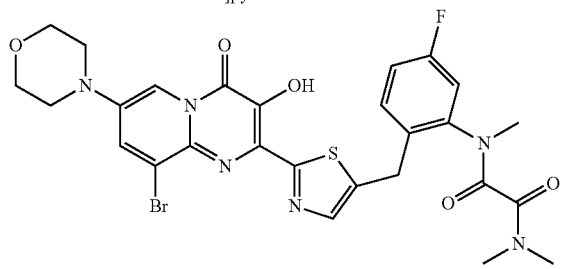

N-(2-[2-(9-Bromo-3-hydroxy-7-morpholin-4-yl-4-oxo-4H-pyrido[1,2-a]pyrimidin-2-yl)-thiazol-5-ylmethyl]-5-fluoro-phenyl}-N,N',N'-trimethyl-oxalamide

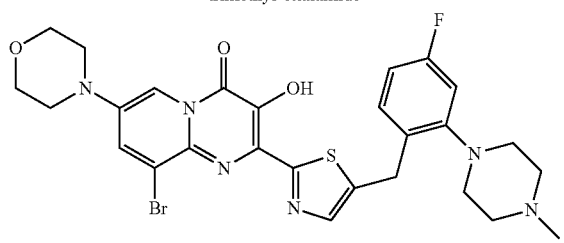

9-Bromo-2-{5-[ 4-fluoro-2-(4-methyl-piperizan-1-yl)-benzyl]-thiazol-2-yl}-3-hydroxy-7-morpholin-4-yl-pyrido{1,2-a]pyrimidin-4-one Further preferred are compounds of Formula (I) as set out in the examples.

As used herein, the term "halo" or "halogen" refers to fluorine (fluoro), chlorine (chloro), bromine (bromo) or iodine (iodo).

As used herein, the terms "alkyl" and "alkylene" either used alone or in compound terms such as NH(alkyl) or N(alkyl)$_2$, refer respectively to monovalent and divalent straight chain or branched hydrocarbon groups, having 1 to 3, 1 to 6, or 1 to 10 carbon atoms as appropriate. For example, suitable alkyl groups include, but are not limited to methyl, ethyl, propyl, isopropyl, n-butyl, sec-butyl, tert-butyl, pentyl, 2-methylbutyl, 3-methylbutyl, n-hexyl, 2-, 3- or 4-methylpentyl, 2-ethylbutyl, n-hexyl or 2-, 3-, 4- or 5-methylpentyl.

As used herein, the term "alkenyl" refers to a straight chain or branched hydrocarbon groups having one or more double bonds between carbon atoms. Suitable alkenyl groups include, but are not limited to, ethenyl, allyl, propenyl, isopropenyl, butenyl, pentenyl and hexenyl.

The term "cycloalkyl" as used herein, refers to cyclic hydrocarbon groups. Suitable cycloalkyl groups include, but are not limited to cyclopropyl, cyclobutyl, cyclopentyl and cyclohexyl.

The term "aryl" as used herein, refers to a $C_6$-$C_{10}$ aromatic hydrocarbon group, for example phenyl or naphthyl.

The term "alkylaryl" includes, for example, benzyl.

The term "heterocycle" when used alone or in compound words includes monocyclic, polycyclic, fused or conjugated hydrocarbon residues, preferably $C_{3-6}$, wherein one or more carbon atoms (and where appropriate, hydrogen atoms attached thereto) are replaced by a heteroatom so as to provide a non-aromatic residue. The bonds between atoms may be saturated or unsaturated. Suitable heteroatoms include, O, N and S. Where two or more carbon atoms are replaced, this may be by two or more of the same heteroatom or by different heteroatoms. Suitable examples of heterocyclic groups may include pyrrolidinyl, piperidyl, piperazinyl, morpholino, quinolinyl, isoquinolinyl, thiomorpholino, dioxanyl, 2,2'-dimethyl-[1,3]-dioxolanyl, tetrahydropyranyl, tetrahydropyranyl, tetrahydropyrrolyl etc.

The term "heteroaryl" includes a 5- or 6-membered heteroaromatic ring containing one or more heteroatoms selected from O, N and S. Suitable examples of heteroaryl groups include furanyl, thiophenyl, tetrazolyl, 1,2,3-triazolyl, 1,2,4-triazolyl, imidazolyl, pyrazolyl, pyridinyl, pyrimidinyl, oxazolyl, oxadiazolyl, thioazolyl, thiodiazolyl etc. The heteroaromatic ring may be fused to a 5- or 6-membered aromatic or heteroaromatic ring to form a bicyclic aromatic ring system eg benzofuran.

Unless otherwise stated, each alkyl, alkylene, cycloalkyl, alkylaryl, aryl, heterocyclyl, or heteroaryl group may be optionally substituted with one or more of $C_1$-$C_3$alkyl, $C_3$-$C_6$cycloalkyl, $C_6$aryl, heterocyclyl, heteroaryl, $C_1$-$C_3$alkylOH, alkylaryl, OH, O$C_1$-$C_3$alkyl, halo, CN, NO$_2$, CO$_2$H, CO$_2$$C_1$-$C_3$alkyl, CONH$_2$, CONH($C_1$-$C_3$alkyl), CON($C_1$-$C_3$alkyl)$_2$, trifluoromethyl, NH$_2$, NH($C_1$-$C_3$alkyl) or N($C_1$-$C_3$alkyl)$_2$. For example, an optionally substituted aryl group may be 4-methylphenyl or 4-hydroxyphenyl group, and an optionally substituted alkyl group may be 2-hydroxyethyl, trifluoromethyl, or difluoromethyl. Each optional alkyl, cycloalkyl, alkylaryl, aryl, heterocyclyl, or heteroaryl substituent may also be optionally substituted.

Examples of optional substituents also include suitable nitrogen protecting groups (see "Protective Groups in Organic Synthesis" Theodora Greene and Peter Wuts, third edition, Wiley Interscience, 1999).

The salts of the compound of formula I are preferably pharmaceutically acceptable, but it will be appreciated that non-pharmaceutically acceptable salts also fall within the scope of the present invention, since these are useful as intermediates in the preparation of pharmaceutically acceptable salts.

The term "pharmaceutically acceptable derivative" may include any pharmaceutically acceptable salt, hydrate or prodrug, or any other compound which upon administration to a subject, is capable of providing (directly or indirectly) a compound of formula I or an antibacterially active metabolite or residue thereof.

Suitable pharmaceutically acceptable salts include, but are not limited to, salts of pharmaceutically acceptable inorganic acids such as hydrochloric, sulphuric, phosphoric, nitric, carbonic, boric, sulfamic, and hydrobromic acids, or salts of pharmaceutically acceptable organic acids such as acetic, propionic, butyric, tartaric, maleic, hydroxymaleic, fumaric, malic, citric, lactic, mucic, gluconic, benzoic, succinic, oxalic, phenylacetic, methanesulphonic, toluenesulphonic, benzenesulphonic, salicylic, sulphanilic, aspartic, glutamic, edetic, stearic, palmitic, oleic, lauric, pantothenic, tannic, ascorbic and valeric acids.

Base salts include, but are not limited to, those formed with pharmaceutically acceptable cations, such as sodium, potassium, lithium, calcium, magnesium, zinc, ammonium, alkylammonium such as salts formed from triethylamine, alkoxyammonium such as those formed with ethanolamine and salts formed from ethylenediamine, choline or amino acids such as arginine, lysine or histidine. General information on types of pharmaceutically acceptable salts and their formation is known to those skilled in the art and is as described in general texts such as "*Handbook of Pharmaceutical salts*" P. H. Stahl, C. G. Wermuth, 1$^{st}$ edition, 2002, Wiley-VCH.

Basic nitrogen-containing groups may be quarternised with such agents as lower alkyl halide, such as methyl, ethyl, propyl, and butyl chlorides, bromides and iodides; dialkyl sulfates like dimethyl and diethyl sulfate; and others.

Hydroxyl groups may be esterified with groups including lower alkyl carboxylic acids, such as acetic acid and 2,2-dimethylpropionic acid, or sulfonated with groups including alkyl sulfonic acids, such as methyl sulfonic acid (see, for instance the compound of Example 15.10).

This invention also encompasses pharmaceutical compositions containing prodrugs of compounds of formula I. This invention also encompasses methods of treating or preventing a viral infection in a subject by administering prodrugs of compounds of the formula I. Compounds of formula I having free amino, amido, hydroxy or carboxylic groups can be converted into prodrugs.

Prodrugs include compounds wherein an amino acid residue, or a polypeptide chain of two or more (eg, two, three or four) amino acid residues which are covalently joined to free amino, hydroxy and carboxylic acid groups of compounds of formula I. The amino acid residues include the 20 naturally occurring amino acids commonly designated by three letter symbols and also include, 4-hydroxyproline, hydroxylysine, demosine, isodemosine, 3-methylhistidine, norvlin, beta-alanine, gamma-aminobutyric acid, citrulline, homocysteine, homoserine, ornithine and methionine sulfone. Prodrugs also include compounds wherein carbonates, carbamates, amides and alkyl esters which are covalently bonded to the above substituents of formula I through the carbonyl carbon prodrug sidechain. Prodrugs also include phosphate derivatives of compounds of formula I (such as acids, salts of acids, or esters) joined through a phosphorus-oxygen bond to a free hydroxyl of compounds of formula I.

It will also be recognised that the compounds of formula I may possess asymmetric centres and are therefore capable of existing in more than one stereoisomeric form. The invention thus also relates to compounds in substantially pure isomeric form at one or more asymmetric centres eg., greater than about 90% ee, such as about 95% or 97% ee or greater than 99% ee, as well as mixtures, including racemic mixtures, thereof. Such isomers may be prepared by asymmetric synthesis, for example using chiral intermediates, or by chiral resolution.

In a second aspect, the present invention provides a method of treatment or prophylaxis of a viral infection in a subject comprising administering to said subject an effective amount of a compound of formula (I) or a pharmaceutically acceptable derivative, salt or prodrug thereof.

In a third aspect, there is provided the use of a compound of Formula I or a pharmaceutically acceptable derivative, salt or prodrug thereof in the preparation of a medicament for the treatment or prophylaxis of a viral infection in a subject.

Preferably, the viral infection of the second and third aspects is a HIV or SIV infection.

More preferably, the HIV or SIV infection comprises a viral strain resistant to other integrase inhibitors such as Isentrass (raltregavir, MK-0158) or elvitegravir. Even more preferably, the viral strain comprises HIV integrase enzyme containing the Q148H/G140S double mutation, N155H/E92Q double mutation, the F121Y/T124K double mutation or the Q148K/G140A/E138A triple mutation.

In a preferred form of the second and third aspects of the present invention, the compound of formula (I) is co-administered with Raltegravir. The compound of formula (I) can be administered simultaneously with Raltegravir, or the compound of formula (I) can be dministered before or after the administration of Raltegravir provided they are in the same course of treatment as would be understood by the person skilled in the art.

In a fourth aspect, the present invention provides pharmaceutical composition comprising a compound according to the first aspect and a pharmaceutically acceptable carrier, diluent or excipient.

The compositions of the present invention may contain other therapeutic agents as described below, and may be formulated, for example, by employing conventional solid or liquid vehicles or diluents, as well as pharmaceutical additives of a type appropriate to the mode of desired administration (for example, excipients, binders, preservatives, stabilizers, flavors, etc.) according to techniques such as those well known in the art of pharmaceutical formulation.

The compounds of the present invention may be administered by any suitable means, for example, parenterally, such as by subcutaneous, intravenous, intramuscular, or intracisternal injection or infusion techniques (e.g., as sterile injectable aqueous or non-aqueous solutions or suspensions).

Pharmaceutical formulations include those for oral, rectal, nasal, topical (including buccal and sub-lingual), vaginal or parenteral (including intramuscular, sub-cutaneous and intravenous) administration or in a form suitable for administration by inhalation or insufflation. The compounds of the invention, together with a conventional adjuvant, carrier or diluent, may thus be placed into the form of pharmaceutical compositions and unit dosages thereof, and in such form may be employed as solids, such as tablets or filled capsules, or liquids as solutions, suspensions, emulsions, elixirs or capsules filled with the same, all for oral use, in the form of suppositories for rectal administration; or in the form of sterile injectable solutions for parenteral (including subcutaneous) use.

In addition to primates, such as humans, a variety of other mammals can be treated according to the method of the present invention. For instance, mammals including, but not limited to, cows, sheep, goats, horses, dogs, cats, guinea pigs, rats or other bovine, ovine, equine, canine, feline, rodent or murine species can be treated. However, the method can also be practiced in other species, such as avian species (e.g., chickens).

The subjects treated in the above method are mammals, including, but not limited to, cows, sheep, goats, horses, dogs, cats, guinea pigs, rats or other bovine, ovine, equine, canine, feline, rodent or murine species, and preferably a human being, male or female.

The term "effective amount" means the amount of the subject composition that will elicit the biological or medical response of a tissue, system, animal or human that is being sought by the researcher, veterinarian, medical doctor or other clinician.

As would be understood by those skilled in the art of treating viral infections, and particularly HIV infections, the term "treatment" does not necessarily mean that the viral infection is completely cured. The term "treatment" encompasses any reduction in the viral load and/or inhibition of replication in the subject being treated.

The term "composition" as used herein is intended to encompass a product comprising the specified ingredients in the specified amounts, as well as any product which results, directly or indirectly, from combination of the specified ingredients in the specified amounts. By "pharmaceutically acceptable" it is meant the carrier, diluent or excipient must be compatible with the other ingredients of the formulation and not deleterious to the recipient thereof.

The terms "administration of" and or "administering a" compound should be understood to mean providing a compound of the invention to the individual in need of treatment.

The pharmaceutical compositions for the administration of the compounds of this invention may conveniently be presented in dosage unit form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases. As used herein, the term "composition" is intended to encompass a product comprising the specified ingredients in the specified amounts, as well as any product which results, directly or indirectly, from combination of the specified ingredients in the specified amounts.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The pharmaceutical composition and method of the present invention may further comprise other therapeutically active compounds which are usually applied in the treatment of the above mentioned pathological conditions. Selection of the appropriate agents for use in combination therapy may be made by one of ordinary skill in the art, according to conventional pharmaceutical principles. The combination of therapeutic agents may act synergistically to effect the treatment or prevention of the various disorders described above. Using this approach, one may be able to achieve therapeutic efficacy with lower dosages of each agent, thus reducing the potential for adverse side effects.

When other therapeutic agents are employed in combination with the compounds of the present invention they may be used for example in amounts as noted in the Physician Desk Reference (PDR) or as otherwise determined by one of ordinary skill in the art.

In the treatment or prevention of conditions which require HIV inhibition or HIV integrase enzyme inhibition an appropriate dosage level will generally be about 0.01 to 500 mg per kg patient body weight per day which can be administered in single or multiple doses. Preferably, the dosage level will be about 0.1 to about 250 mg/kg per day; more preferably about 0.5 to about 100 mg/kg per day. A suitable dosage level may be about 0.01 to 250 mg/kg per day, about 0.05 to 100 mg/kg per day, or about 0.1 to 50 mg/kg per day. Within this range the dosage may be 0.05 to 0.5, 0.5 to 5 or 5 to 50 mg/kg per day. For oral administration, the compositions are preferably provided in the form of tablets containing 1.0 to 1000 milligrams of the active ingredient, particularly 1.0, 5.0, 10.0, 15.0, 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The compounds may be administered on a regimen of 1 to 4 times per day, preferably once or twice per day.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

In order that the nature of the present invention may be more clearly understood preferred forms thereof will now be described by reference to the following non-limiting Examples.

1. Routes of Synthesis 1.1 For Core Formation:

Scheme 1: Preparation of the pyrimidinone bicyclic system

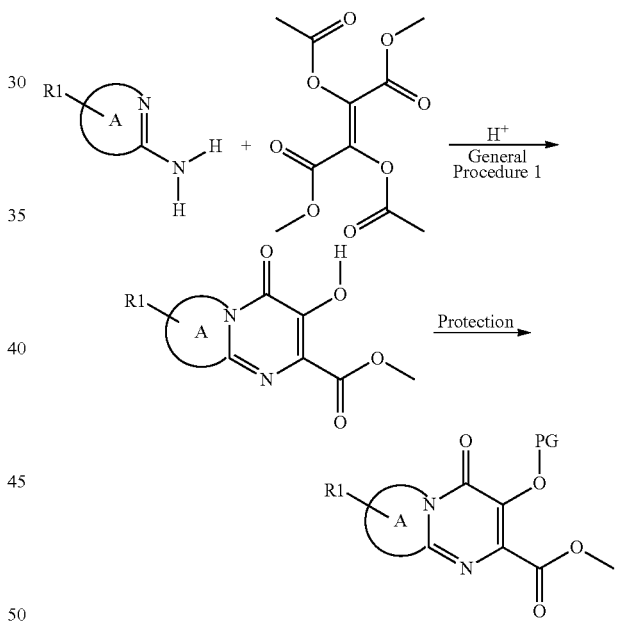

General Procedure 1: Adaption of Organic Preparations and Procedures International, 22(4), 1990, 532-534

International patent Application No. PCT/AU2007/001980 in the name of Avexa.

The amino compound can be reacted as in scheme 1 with the fumarate derivative or suitable analogues of fumarate where for example the acetyl groups can be replaced by other suitable leaving groups such as tosyl or mesyl. The reaction can be carried out in a suitable solvent such as methanol, DME, DMA, DMSO, chloroform, THF or dioxane. The reaction can be heated or subject to microwave irradiation (see for example B. R. Roberts & C. R. Strauss, Acc. Chem. Res. 2005, 38, 653-661, "Toward Rapid, 'Green' Predictable Microwave-assisted Synthesis"). The reaction can be performed in the absence or presence of catalytic amounts of acid or base.

1.2 Generic Schemes: Azole Formation
1.2.1 For H1=1,3-oxazole, 1,3-thiazole, and Imidazole:

Scheme 2: Preparation of the 1,3-oxazole and 1,3-thiazole via Gabriel or Robinson-Gabriel method

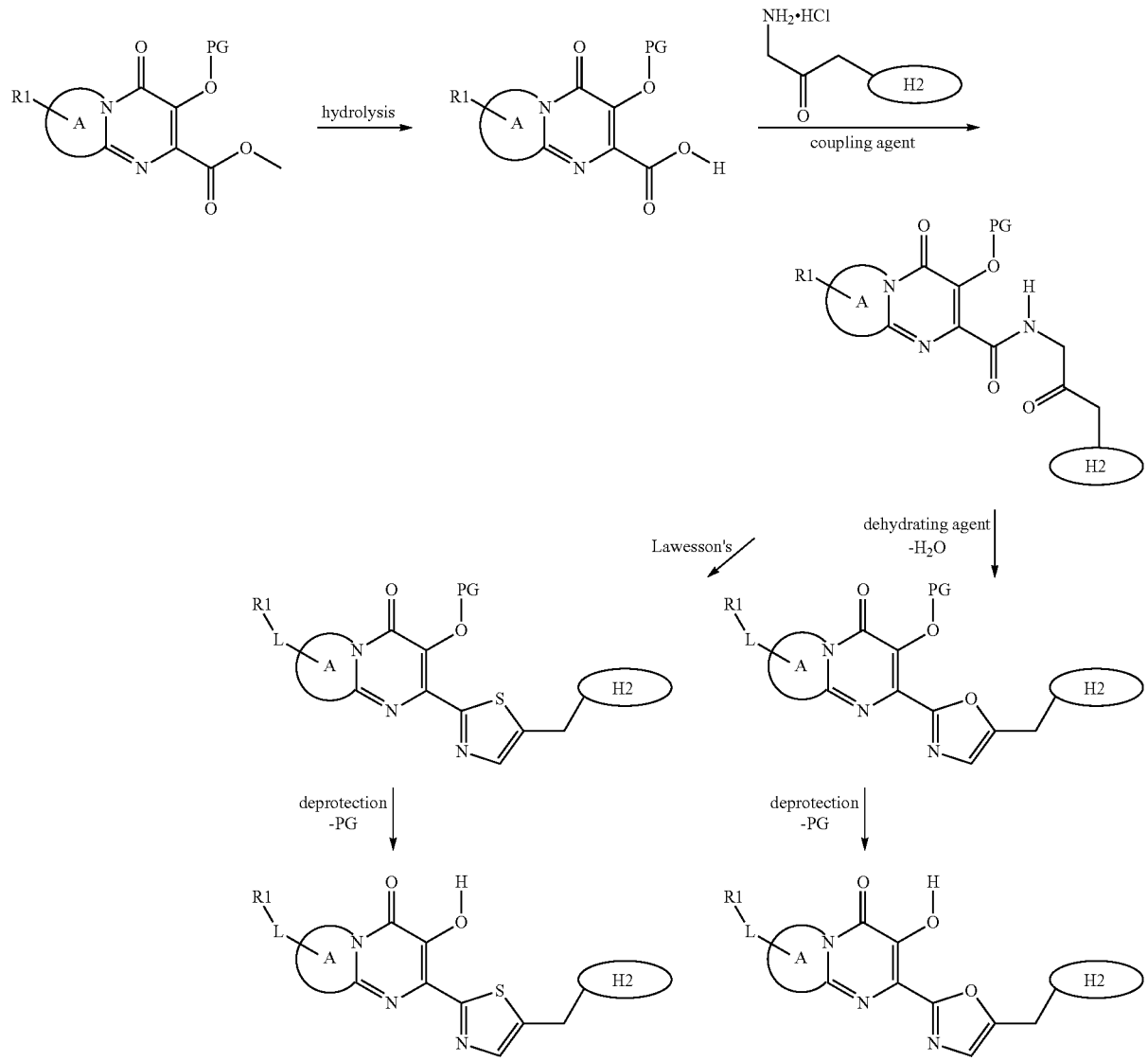

1. International patent Application No. PCT/AU2007/001980 in the name of Avexa.
2. Editor R. R. Gupta, Microwave-Assisted Synthesis of Heterocycles, Springer Berlin/Heidelberg. ISSN: 1861-9282 (Print) 1861-9290 (Online), 2006

Scheme 3: Preparation of the imidazole

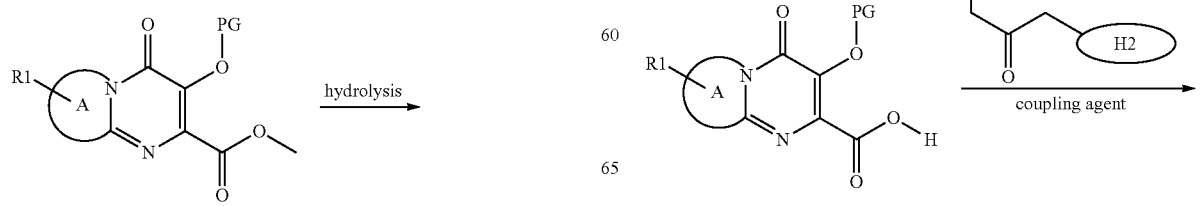

-continued

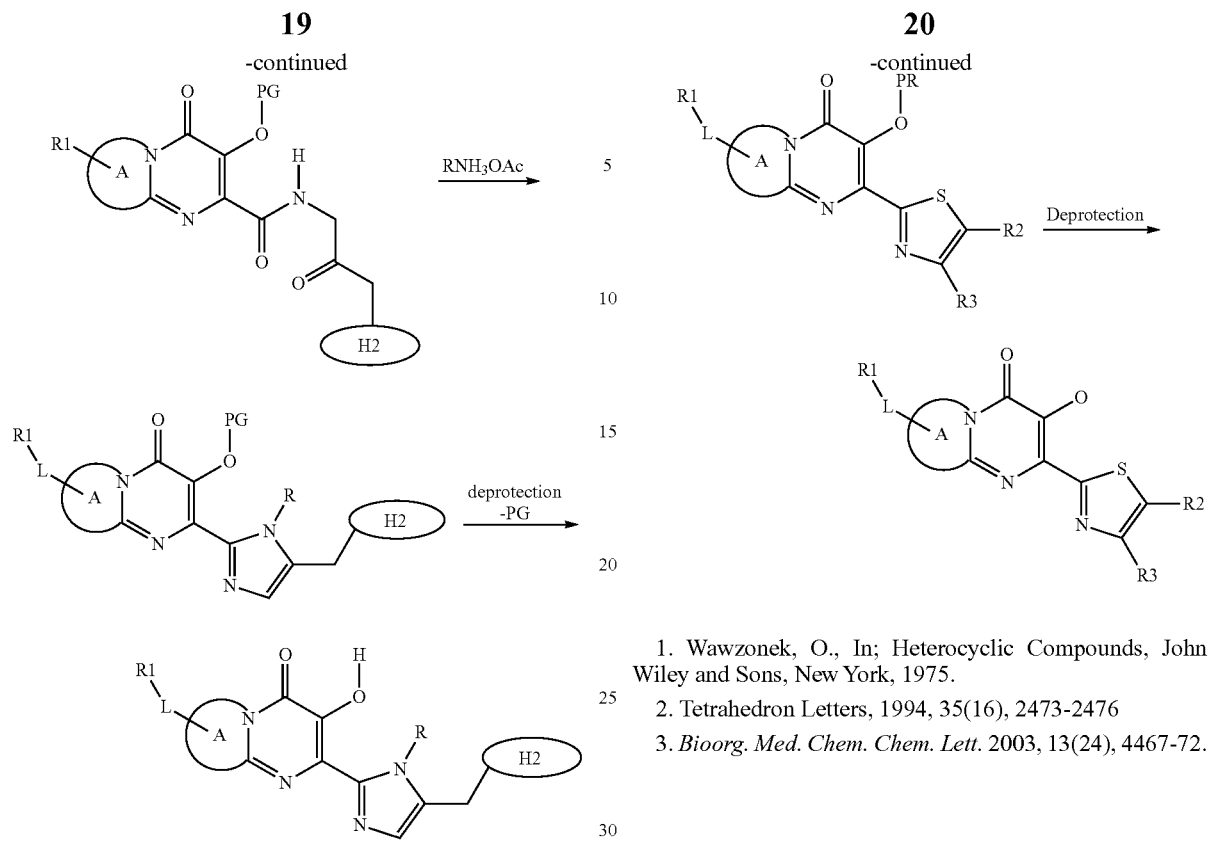
1. Wawzonek, O., In; Heterocyclic Compounds, John Wiley and Sons, New York, 1975.
2. Tetrahedron Letters, 1994, 35(16), 2473-2476
3. *Bioorg. Med. Chem. Chem. Lett.* 2003, 13(24), 4467-72.
Editor R. R. Gupta, Microwave-Assisted Synthesis of Heterocycles, Springer Berlin/Heidelberg. ISSN: 1861-9282 (Print) 1861-9290 (Online), 2006
Scheme 4: Preparation of the 1,3-thiazole via Hantzsch method
Scheme 5: Alternative preparation of the 1,3-thiazole
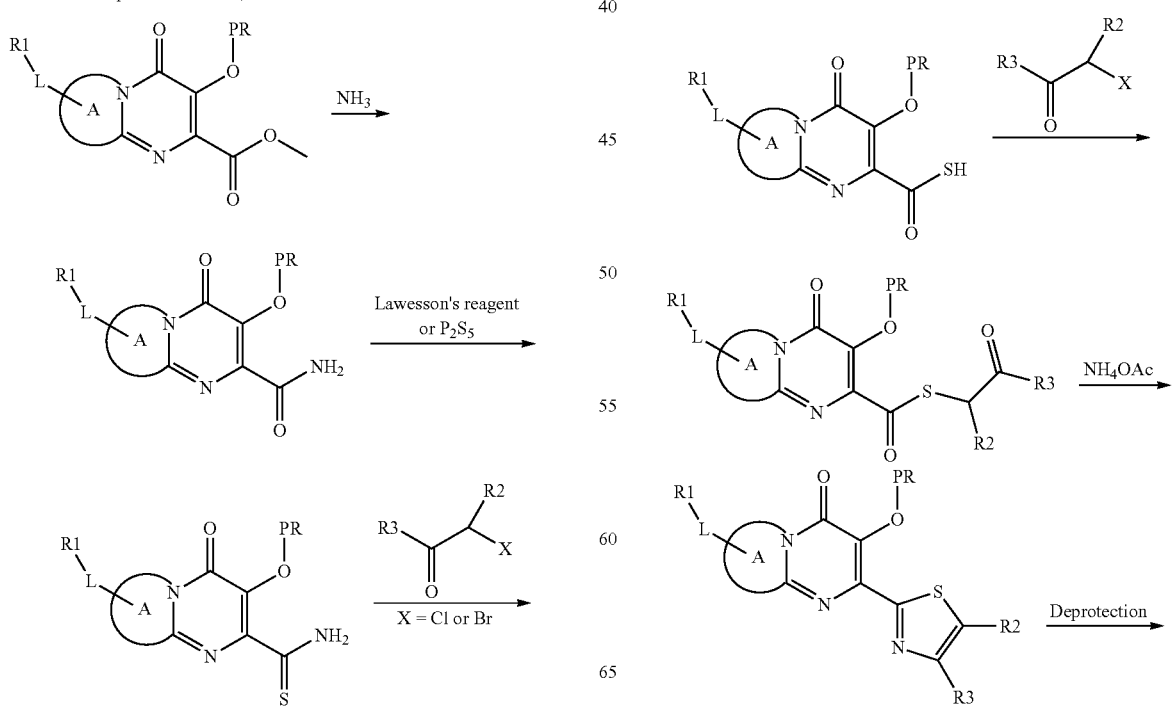

21
-continued
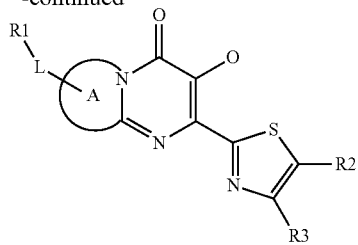
*Tetrahedron.* 2001, 57 (20), 4323-4336.
*Org. Lett.* 2003, 5(16), 2785-88;
*Synthesis.* 1976, 696-697
Scheme 6: Alternative preparation of the 1,3-thiazole from aldehyde
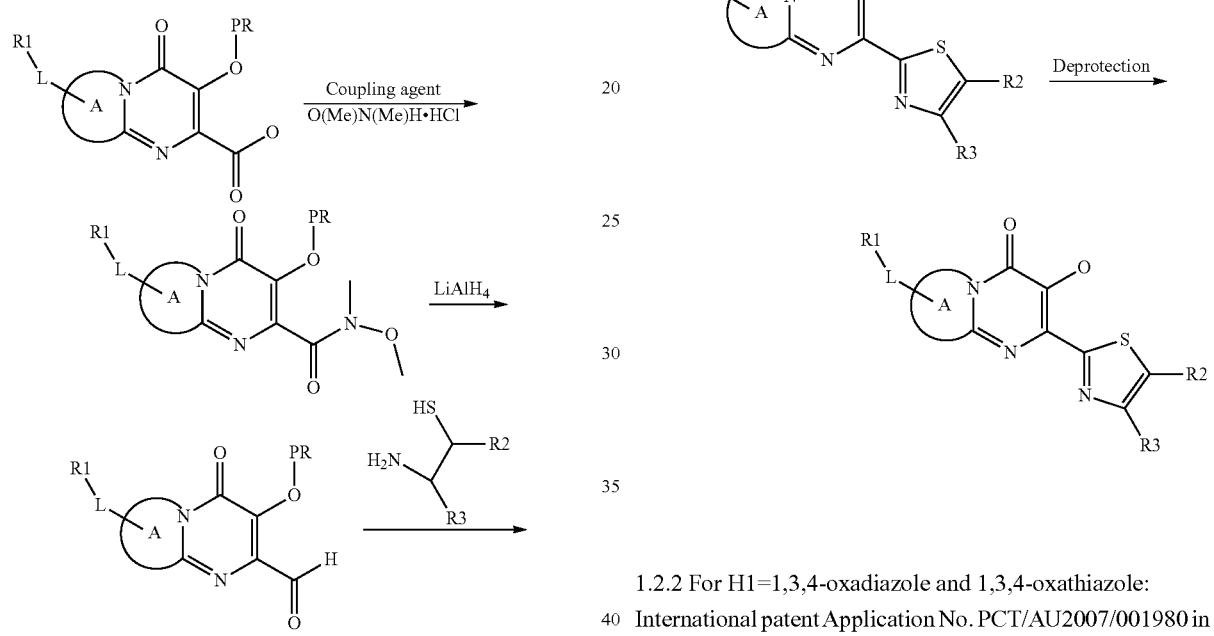
22
-continued
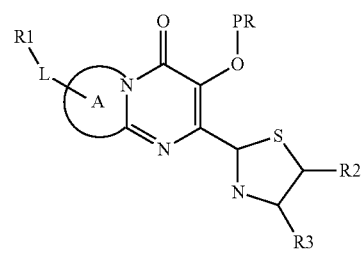
1.2.2 For H1=1,3,4-oxadiazole and 1,3,4-oxathiazole:
International patent Application No. PCT/AU2007/001980 in the name of Avexa.
Scheme 7: Preparation of the 1,3,4-oxadiazole and 1,3,4-thiadiazole
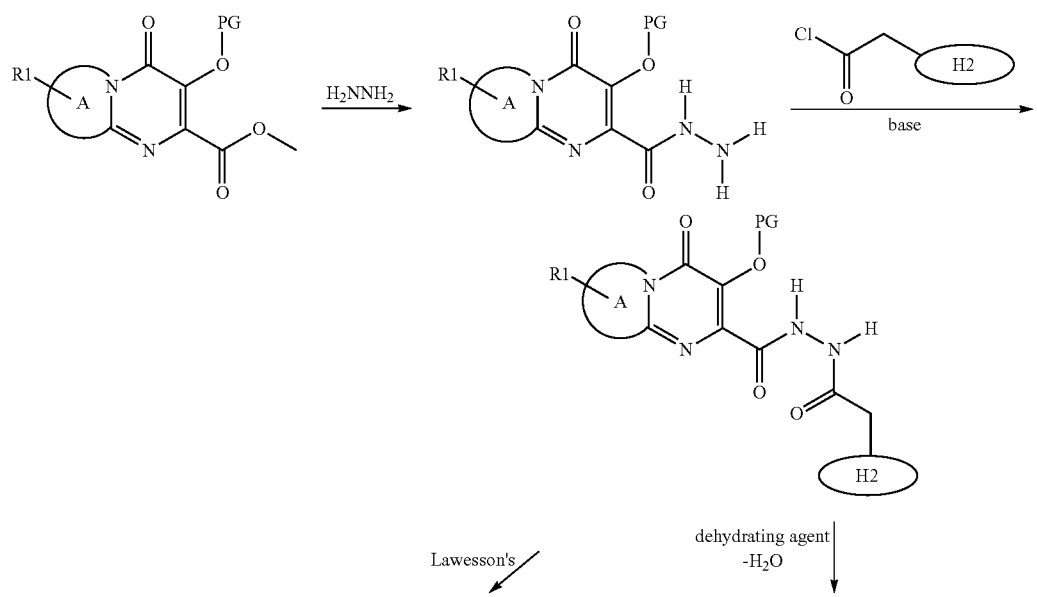

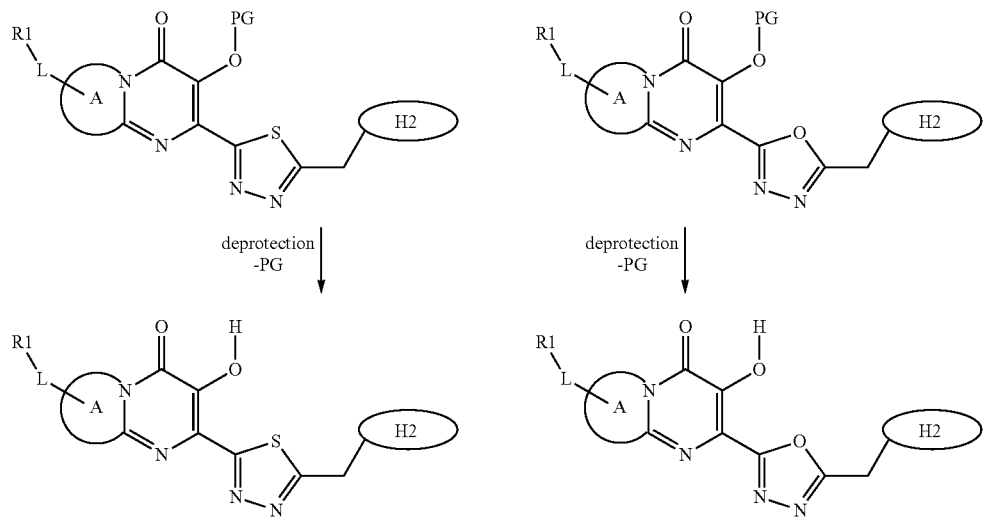
1.2.3 For H1=1,2,4-oxadiazole
Scheme 8: Preparation of the 1,2,4-oxadiazole
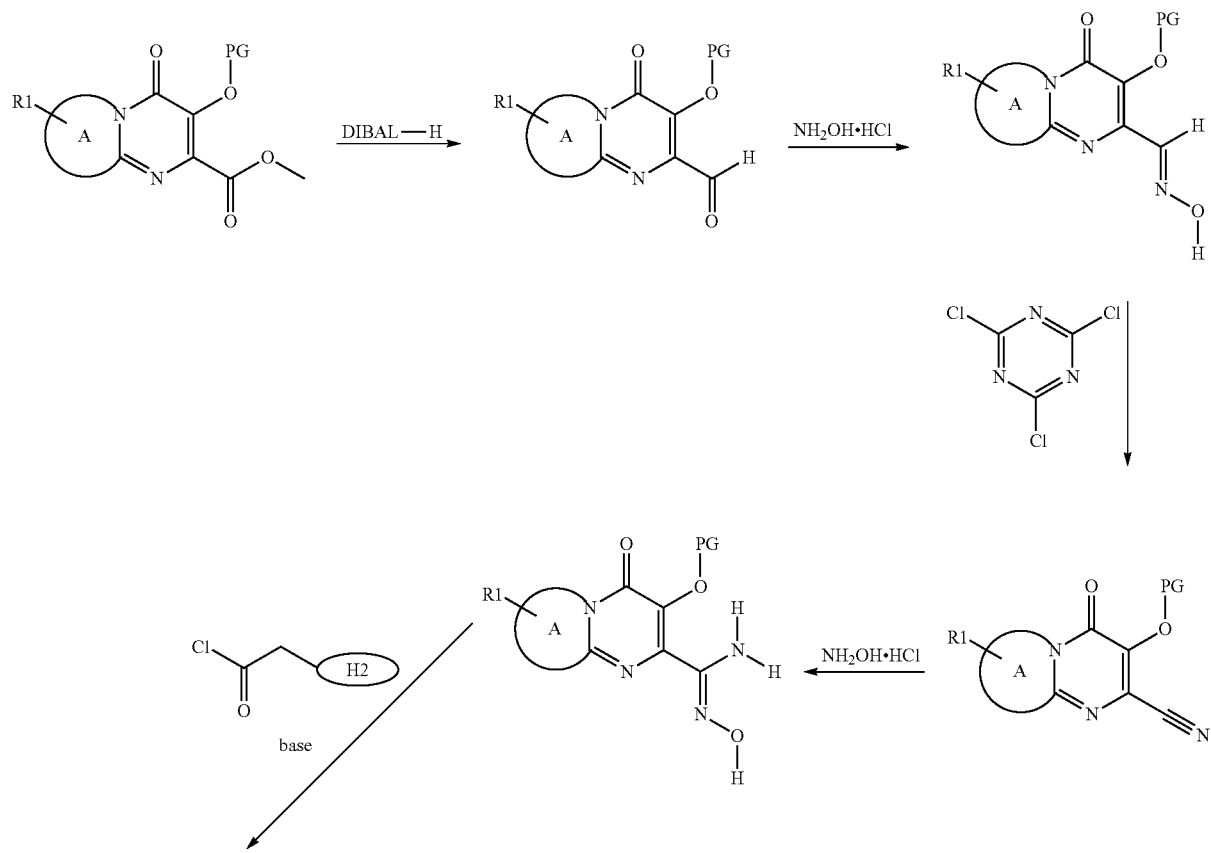

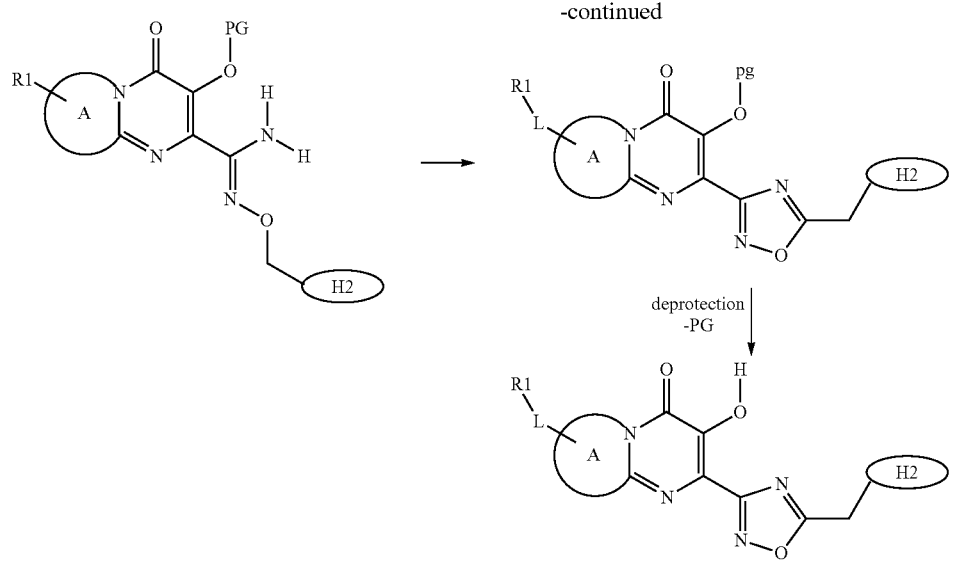

International patent Application No. PCT/AU2007/001980 in the name of Avexa.

Scheme 9: Preparation of the 1,2,4-oxadiazole (reversed roles)

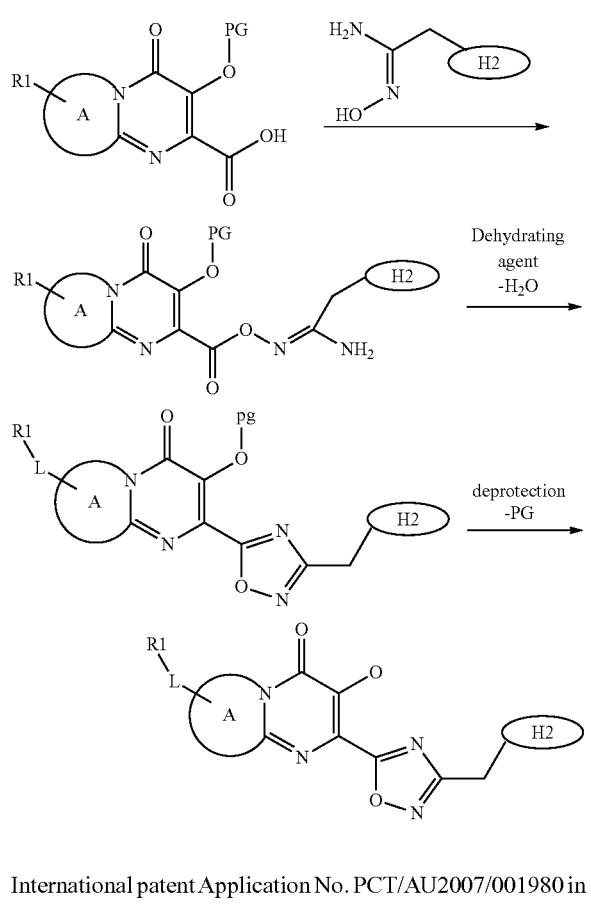

International patent Application No. PCT/AU2007/001980 in the name of Avexa.

1.3 Generic Schemes: Preparation of Ketoamines

Scheme 10: Preparation of 1-Amino-3-aryl-propan-2-one hydrochloride

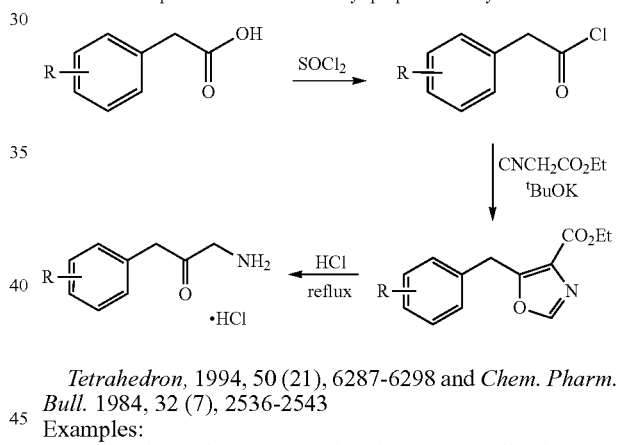

*Tetrahedron*, 1994, 50 (21), 6287-6298 and *Chem. Pharm. Bull.* 1984, 32 (7), 2536-2543

Examples:
R=3-F,4-Cl; 3-Cl,4-F International Patent Application No. PCT/AU2007/001980
R=4-F; 2,4-Cl$_2$ International Patent Application No. PCT/AU2007/001980
R=4-Cl: known. *Chem. Pharm. Bull.* 1984, 32 (7), 2536-2543
R=2-NO$_2$ known: *Tetrahedron* 1994, 50(21) 6287-6298

Scheme 11: Alternative preparation of 1-Amino-3-aryl-propan-2-one hydrochloride

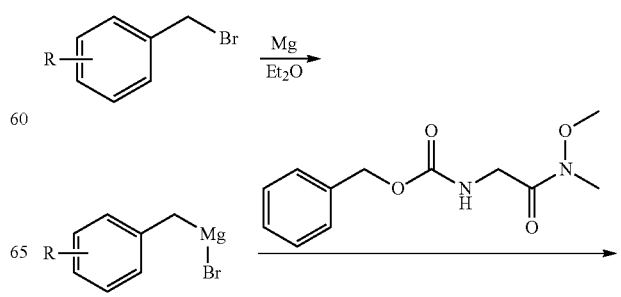

27
-continued
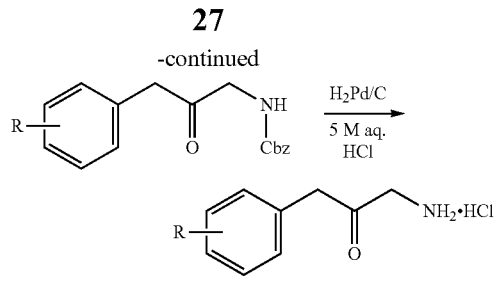
US20040229909; "Antiviral agent", Shionogi
Scheme 12: Alternative preparation of 1-Amino-3-aryl-propan-2-one hyrdrochloride
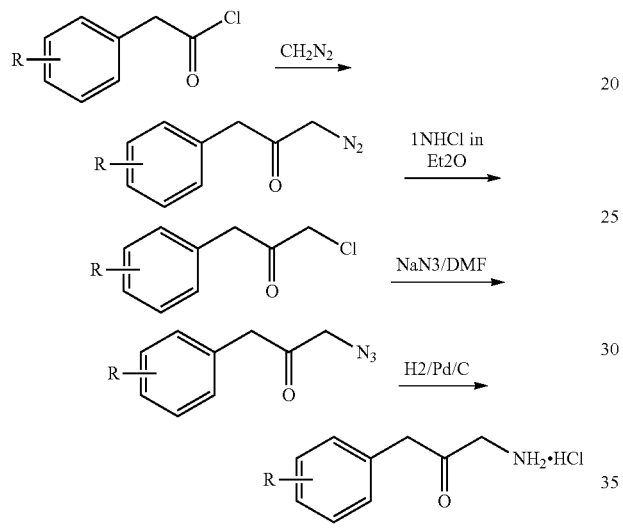
Journal of Organic Chemistry (2003), 68(7), 2798-2802. (for ketoazide from chloroketone)
Scheme 13: Alternative preparation of 1-Amino-3-aryl-propan-2-one hyrdrochloride
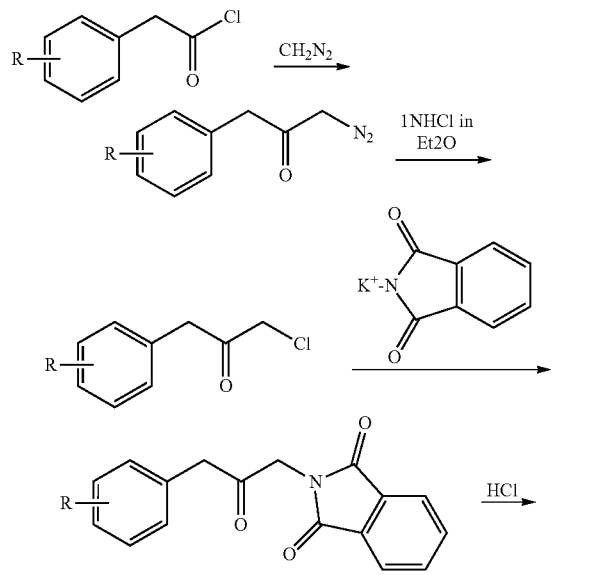
28
-continued
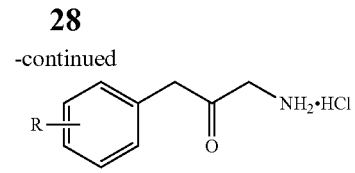
Scheme 14: Preparation of o-ester ketoamine
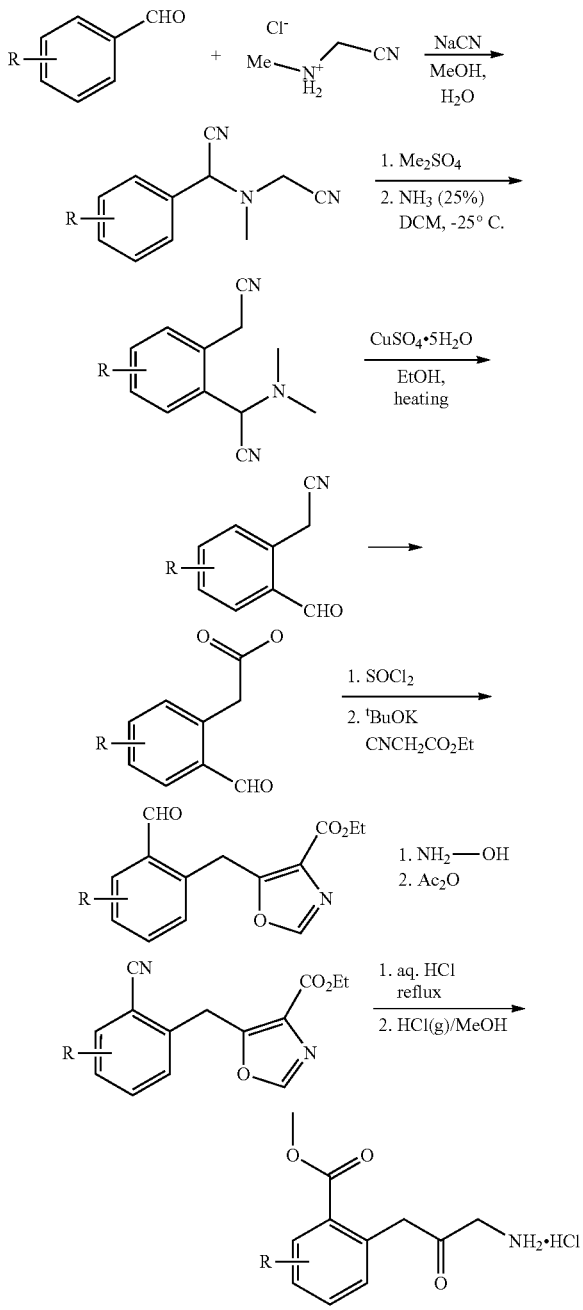
J. Org. Chem. 1991, 56(24), 6933-6937

Scheme 15: Preparation of o-aminomethyl ketoamine
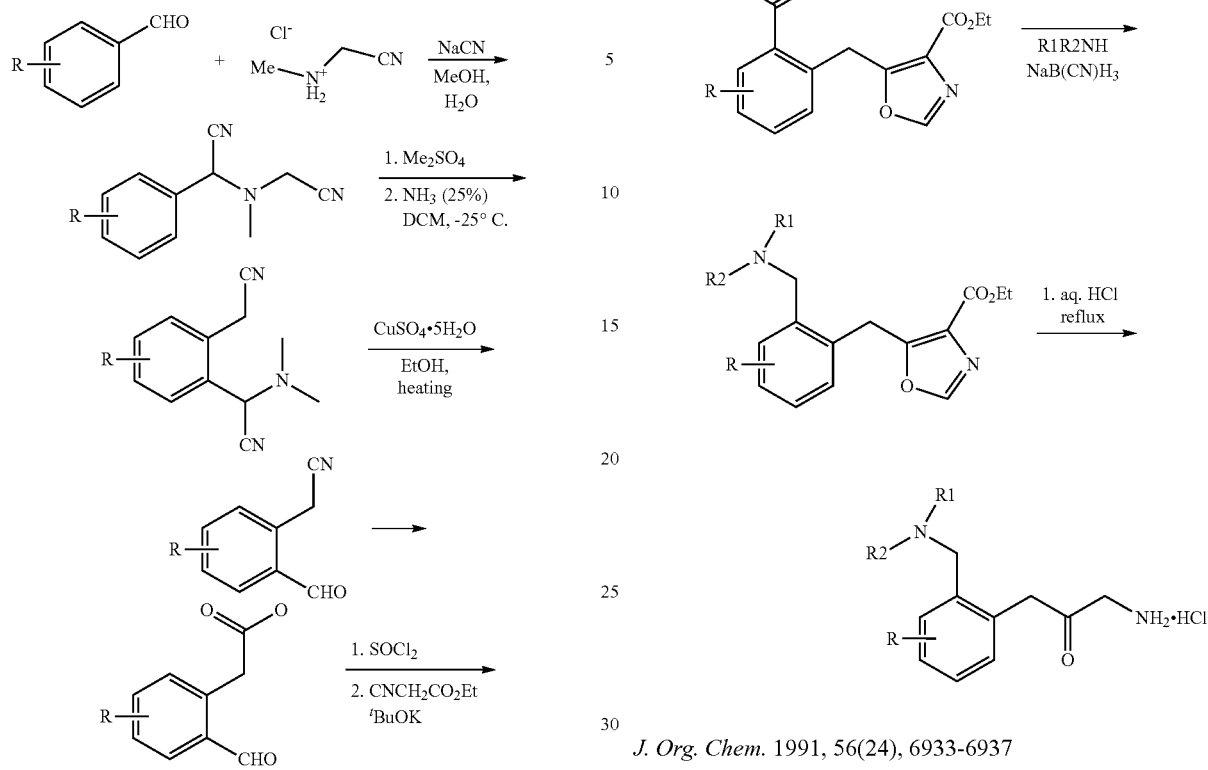
*J. Org. Chem.* 1991, 56(24), 6933-6937
1.4 Generic Schemes: Derivatization
Scheme 16: Derivatization of thiazole-imidazole examples: Variation at position 3 (via carboxamide)
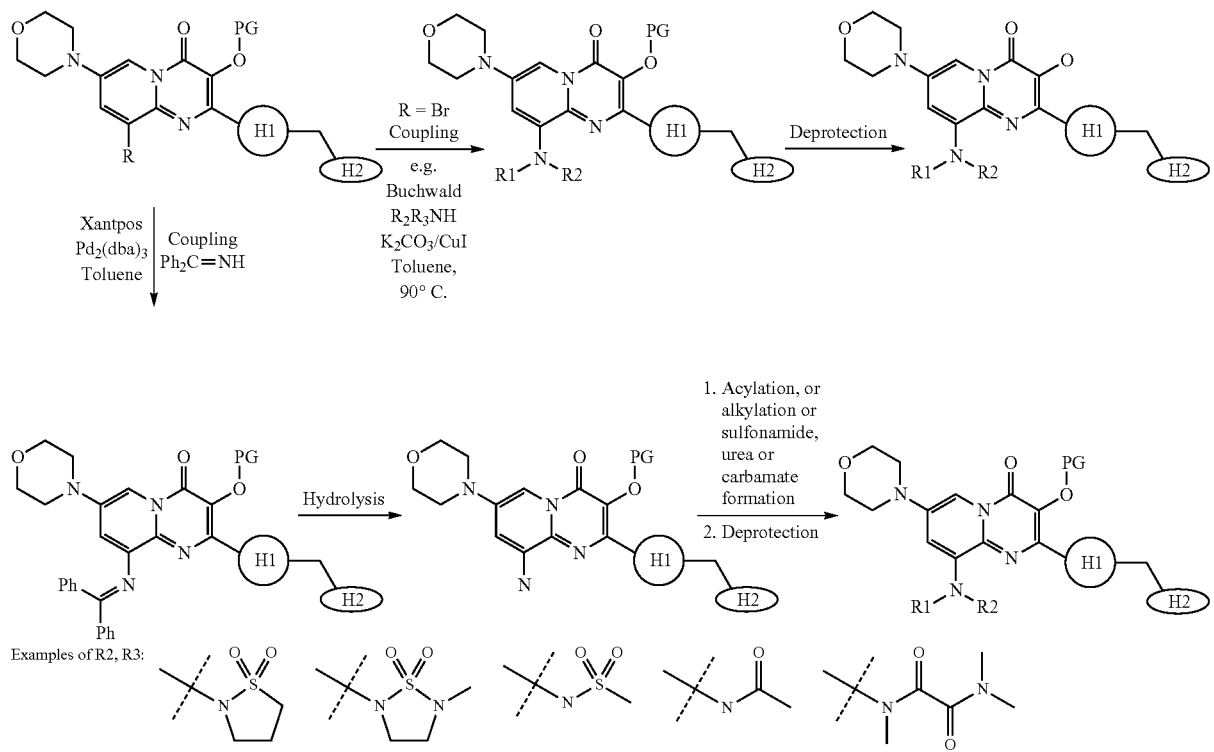

-continued
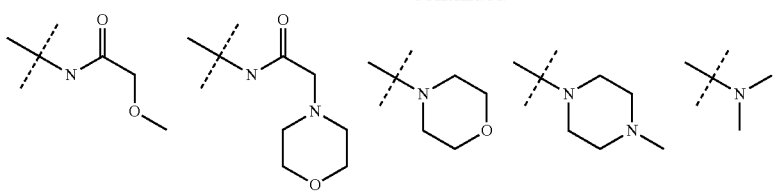
Scheme 17: Derivatization of the aromatic ring: metal mediated couplings with R2R3NH
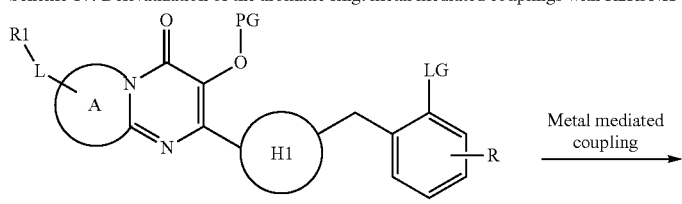
LG (leaving groups) = I, Br, Cl, F, OTf, OMs
R = 0-2 substituents
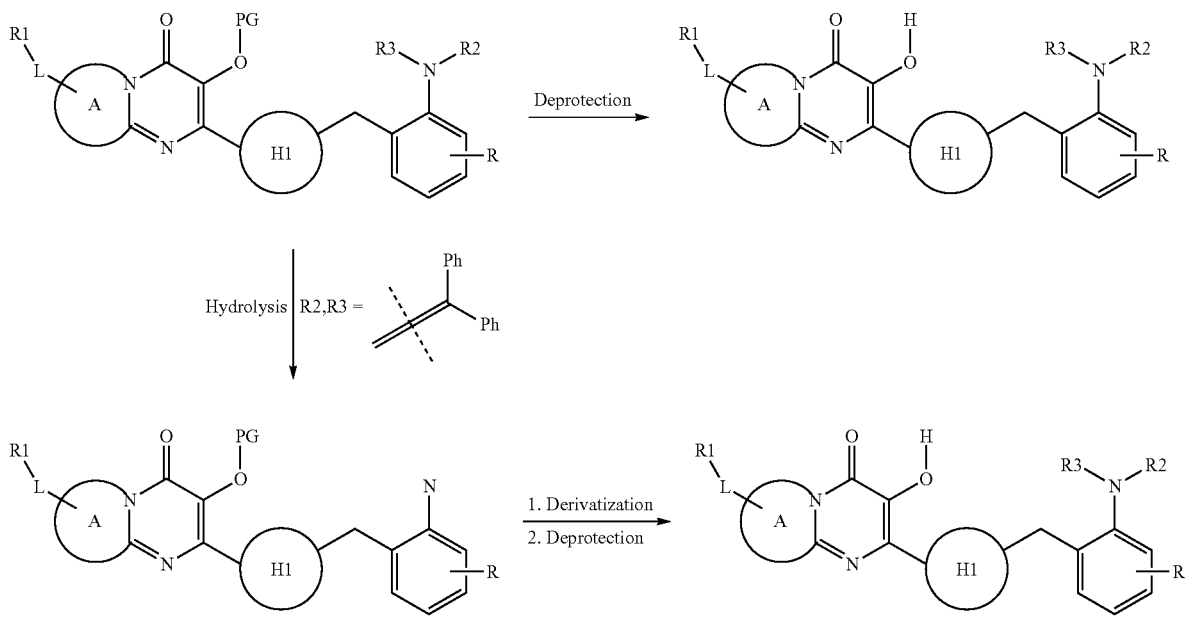
Scheme 18: Derivatization of the aromatic ring: metal mediated couplings with R2XH
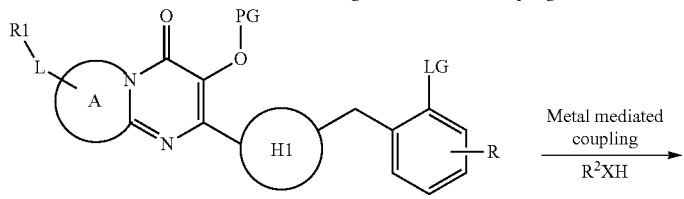
LG (leaving groups) = I, Br, Cl, F, OTf, OMs
R = 0-2 substituents 33   -continued   34
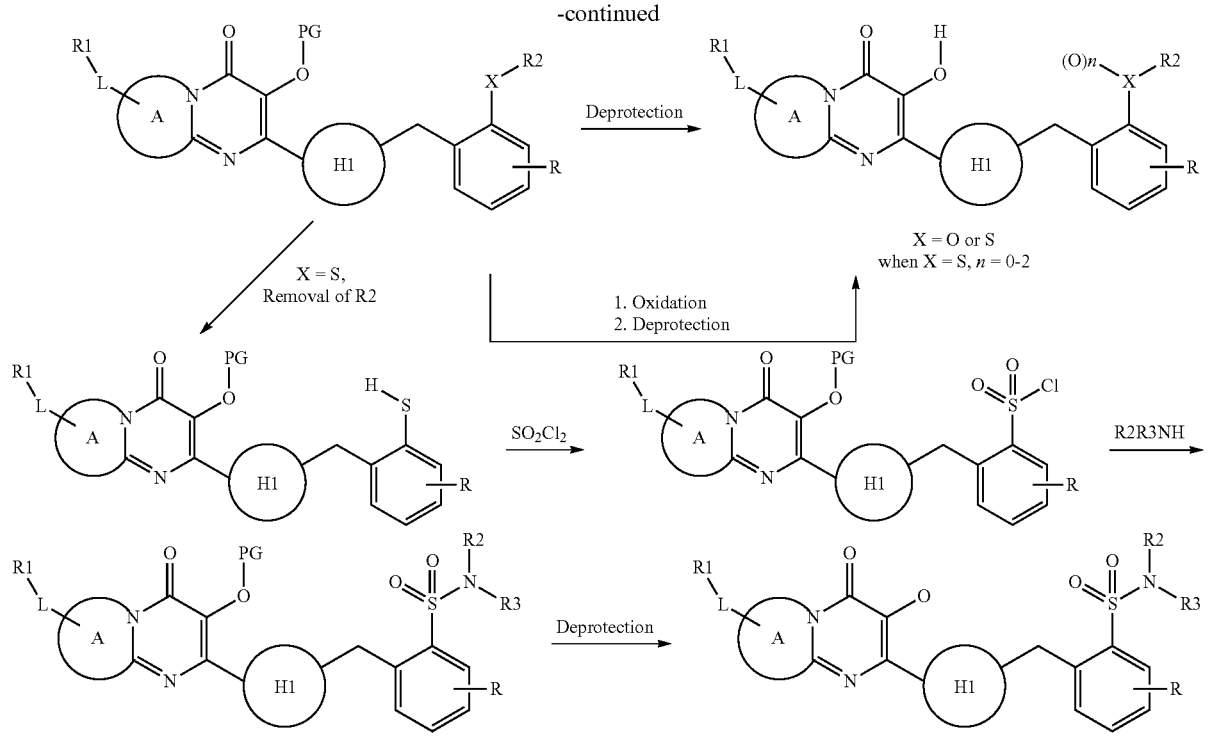
X = O or S
when X = S, n = 0-2
Scheme 19: Derivatization of the aromatic ring: metal mediated couplings with CO2
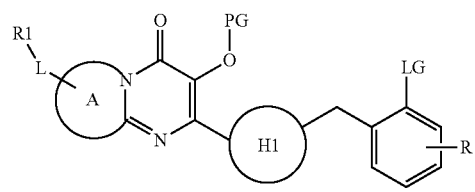
LG (leaving groups) = I, Br, Cl, F, OTf, OMs
R = 0-2 substituents
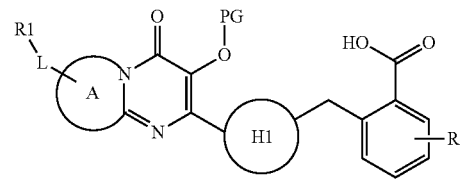
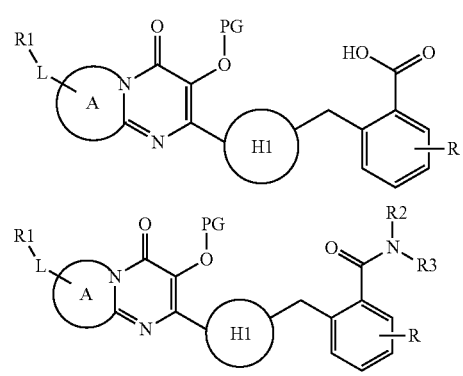
Scheme 20: Derivatization of the aromatic ring: metal mediated couplings with DMF
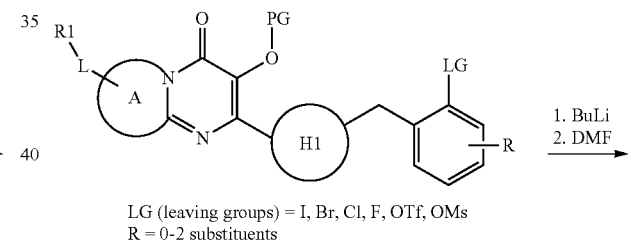
LG (leaving groups) = I, Br, Cl, F, OTf, OMs
R = 0-2 substituents
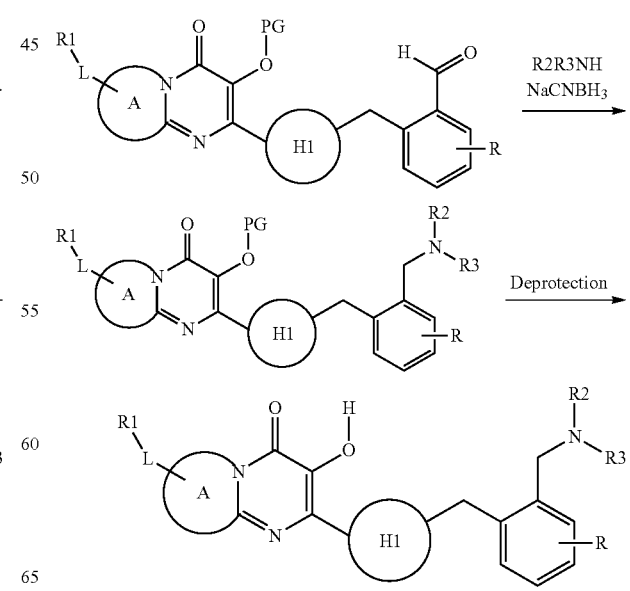

Scheme 21: Derivatization of the aromatic ring: amide formation in ortho position
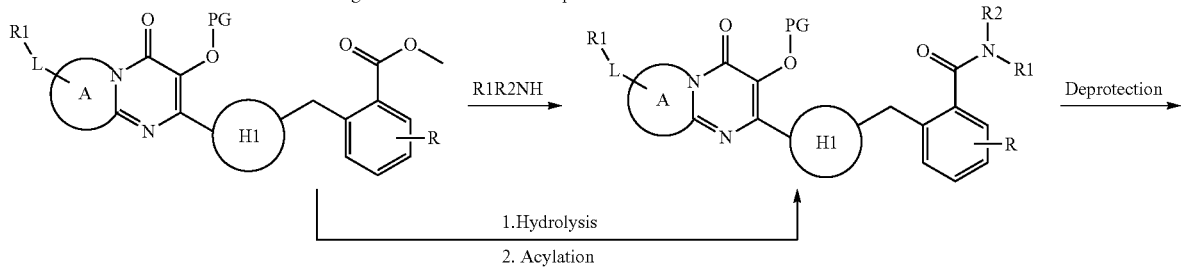
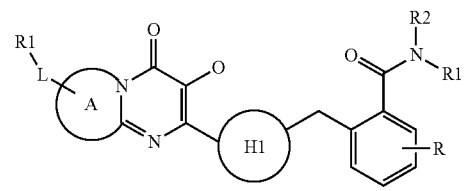
Scheme 22: Derivatization of the aromatic ring: amine in ortho position
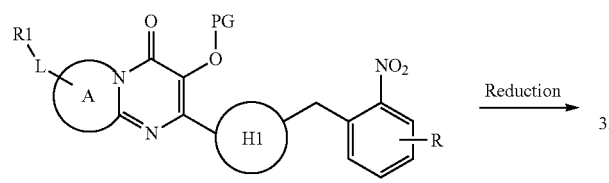
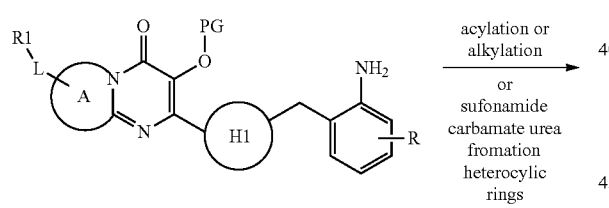
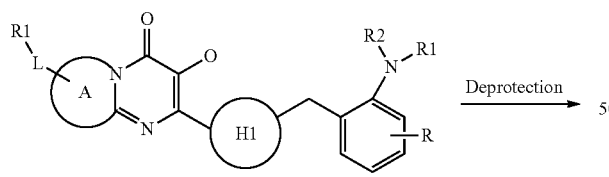
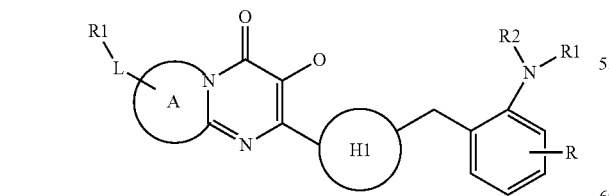
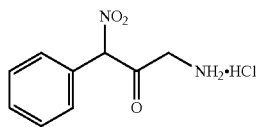
Tetrahedron (1994), 50(21), 6287-98.
Scheme 23: Derivatisation of a thiazole substituent
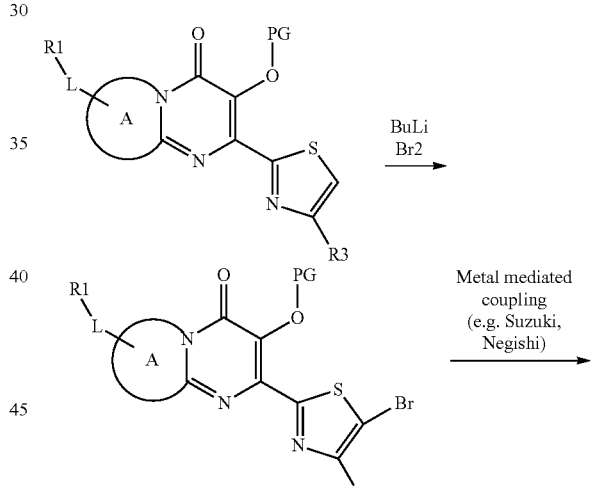
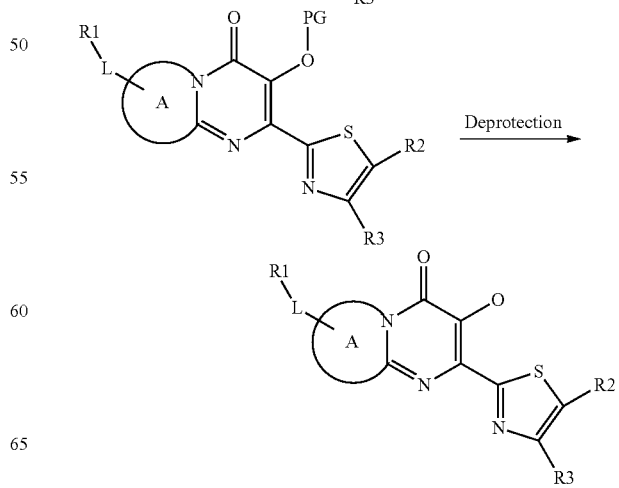

2 Synthetic Examples

Methods

HPLC Condition

All HPLC measurements were performed on a Varian ProStar System or Waters 2690 Alliance System.

Method 1
Column:
  Waters Exterra C18 Column (Part #186000410) at 30° C., flow rate 0.4 mL/min, spectra measured at 254 nM
Buffers:
  Buffer A: 100% water, Buffer B: 100% acetonitrile, Buffer C: 2% aqueous TFA
Gradient: (Linear Gradient Curve 6)

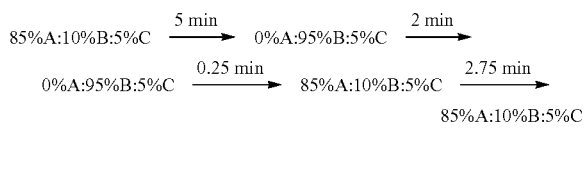

Method 2
Column:
  Merck C18 Chromolith Column (Part #1.02129.0001) at 30° C., flow rate 4 mL/min, spectra measured at 254 nM
Buffers:
  Buffer A: 100% water, Buffer B: 100% acetonitrile, Buffer C: 2% aqueous TFA
Gradient: (Linear Gradient Curve 6)

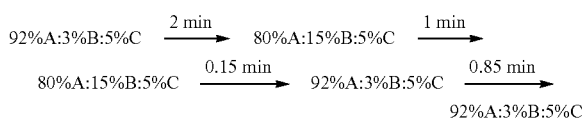

Method 3
Column:
  Merck C18 Chromolith Column (Part #1.02129.0001) at 30° C., flow rate 4 mL/min, spectra measured at 254 nM
Buffers:
  Buffer A: 100% water, Buffer B: 100% acetonitrile, Buffer C: 2% aqueous TFA
Gradient: (Linear Gradient Curve 6)

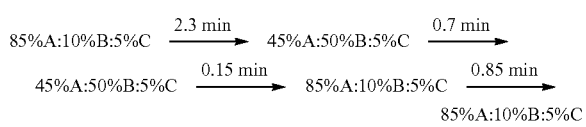

Method 4
Column:
  Merck C18 Chromolith Column (Part #1.02129.0001) at 30° C., flow rate 4 mL/min, spectra measured at 254 nM
Buffers:
  Buffer A: 100% water, Buffer B: 100% acetonitrile, Buffer C: 2% aqueous TFA
Gradient: (Linear Gradient Curve 6)

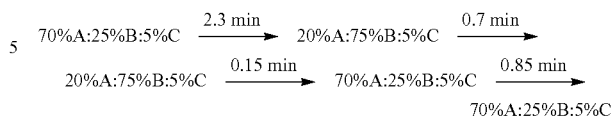

Method 5
Column:
  Phenomenex Gemini C18 Column (Part #344382-3) at 30° C., flow rate 0.4 mL/min, spectra measured at 254 nM
Buffers:
  Buffer A: 100% water, Buffer B: 100% acetonitrile, Buffer C: 2% aqueous TFA
Gradient: (Linear Gradient Curve 6)

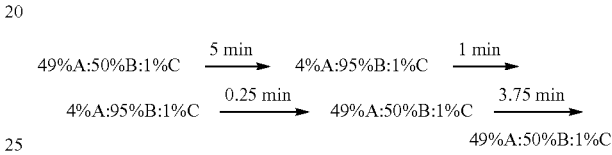

Method 6
Column:
  Phenomenex Gemini C18 Column (Part #344382-3) at 30° C., flow rate 0.4 mL/min, spectra measured at 254 nM
Buffers:
  Buffer A: 100% water, Buffer B: 100% acetonitrile, Buffer C: 2% aqueous TFA
Gradient: (Linear Gradient Curve 6)

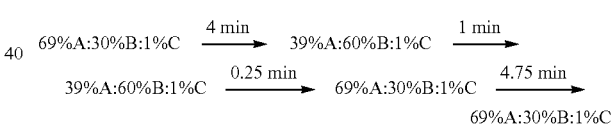

Method 7
Column:
  Waters Symmetry® C18 Column (Part No WAT045905) at 25° C., flow rate 1 mL/min, spectra measured at 254 nM
Buffers:
  Buffer A: 100% acetonitrile, Buffer B: 0.1% aqueous TFA
Gradient: (Linear Gradient Curve 6)

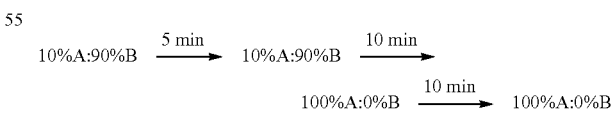

Method 8
Column:
  Waters Symmetry® C18 Column (Part No WAT045905) at 25° C., flow rate 1 mL/min, spectra measured at 254 nM
Buffers:
  Buffer A: 100% acetonitrile, Buffer B: 0.1% aqueous TFA Gradient: (Linear Gradient Curve 6)

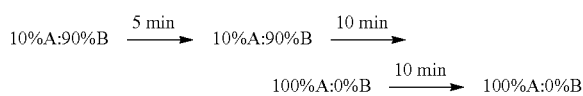

Example 1

Preparation of 3-Benzyloxy-9-bromo-7-morpholin-4-yl-4-oxo-4H-pyrido[1,2-a]pyrimidine-2-carboxylic acid

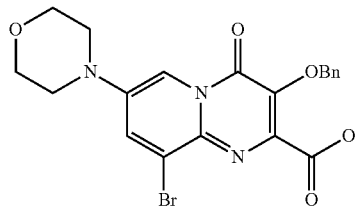

The titled compound was prepared by adapting methods described for example 8.1 of International patent Application No. PCT/AU2007/001980 in the name of Avexa.

¹HNMR (300 MHz, d-DMSO): δ 3.22 (t, J=4.5 Hz, 4H), δ 3.76 (t, J=4.5 Hz, 4H), δ 5.15 (s, 2H), δ 7.34-7.48 (m, 5H), δ 8.19 (d, J=2.4 Hz, 1H), δ 8.52 (d, J=2.4 Hz, 1H).

MS (ESI⁻) m/z 458 (M−1).

Example 2

Preparation of 3-benzyloxy-9-bromo-7-morpholin-4-yl-4-oxo-4H-pyrido[1,2-a]pyrimidine-2-carboxylic acid [3-(4-fluoro-phenyl)-2-oxo-propyl]-amide

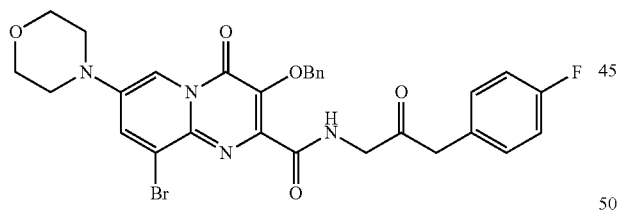

To a solution of the product of example 1 (270 mg, 0.586 mmol) in DMF ml) was added 1-amino-3-(4-fluoro-phenyl)-propan-2-one hydrochloride (240 mg, 1.176 mmol), EDCI·HCl (140 mg, 0.732 mmol), HOBt (100 mg, 0.74 mmol) and triethylamine (240 mg, 2.376 mmol) successively at room temperature. The mixture was stirred overnight, after which saturated sodium bicarbonate solution (15 ml) was added and the mixture was extracted with ethyl acetate. The combined extracts were washed with water and saturated brine, dried over sodium sulfate and concentrated under reduced pressure. The residue was purified by column chromatography (CH₂Cl₂/MeOH=100/1) to give the titled compound (190 mg, 57% yield).

¹H NMR (300 MHz, DMSO-d⁶) δ 3.20-3.30 (m, 4H), 3.74-3.82 (m, 4H), 3.88 (s, 2H), 4.28 (d, J=5.6 Hz, 2H), 5.14 (s, 2H), 7.14 (t, J=9.0 Hz, 2H), 7.24 (dd, J=6.2, 8.8 Hz, 2H), 7.28-7.40 (m, 3H), 7.47-7.54 (m, 2H), 8.20 (d, J=2.6 Hz, 1H), 8.54 (d, J=2.6 Hz, 1H), 8.75 (t, J=5.5 Hz, 1H).

MS (ESI⁺) m/z 609 (M [Br⁷⁹]+1), 611 (M [Br⁸¹]+1)

Example 3

Preparation of 3-benzyloxy-9-bromo-2-[5-(4-fluoro-benzyl)-oxazol-2-yl]-7-morpholin-4-yl-pyrido[1,2-a]pyrimidin-4-one

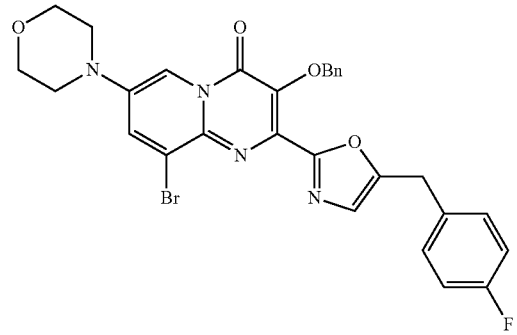

To a solution of the product of example 2 (140 mg, 0.23 mmol) in acetonitrile (2 ml), carbon tetrachloride (213 mg, 1.383 mmol), triethylamine (117 mg, 1.1584 mmol) and triphenylphosphine (302 mg, 1.151 mmol) were added successively at room temperature. The mixture was stirred for 3 hours. The product was purified by column chromatography (CH₂Cl₂/MeOH=150/1) to give the titled compound (25 mg, 20% yield).

¹H NMR (300 MHz, DMSO-d⁶) δ 3.21-3.29 (m, 4H), 3.75-3.81 (m, 4H), 4.14 (s, 2H), 5.18 (s, 2H), 7.13-7.21 (m, 3H), 7.28-7.45 (m, 7H), 8.18 (d, J=2.6 Hz, 1H), 8.52 (d, J=2.6 Hz, 1H).

MS (ESI⁺) m/z 591 (M [Br⁷⁹]+1), 593 (M [Br⁸¹]+1)

Example 4

Preparation of 2-[5-(4-fluoro-benzyl)-oxazol-2-yl]-3-hydroxy-9-iodo-7-morpholin-4-yl-pyrido[1,2-a]pyrimidin-4-one

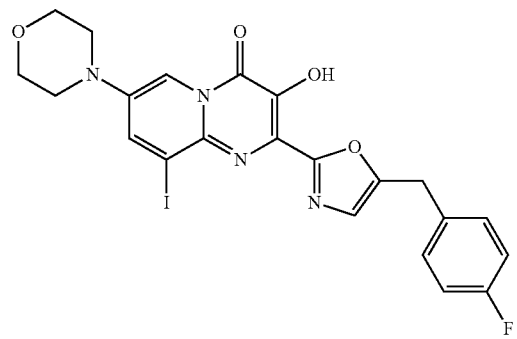

To a solution of the product of example 3 (25 mg, 0.042 mmol) in acetonitrile (1 ml) was added idodotrimethylsilane (TMSI) (0.05 ml, 0.338 mmol) at room temperature. The mixture was stirred at room temperature for 8 hours, after which methanol (0.1 ml) was added to quench the reaction.

Then saturated solution of $Na_2S_2O_3$ was added drop-wise till a yellow solid was precipitated. The resulting solids were collected by filtration, washed with ethyl acetate to give the titled compound (13 mg, 60% yield).

$^1$H NMR (300 MHz, DMSO-d$^6$) δ 3.14-3.21 (m, 4H), 3.71-3.80 (m, 4H), 4.23 (s, 2H), 7.20 (t, J=8.9 Hz, 2H), 7.26 (s, 1H), 7.42 (dd, J=5.5, 8.5 Hz, 2H), 8.04 (d, J=2.4 Hz, 1H), 8.46 (d, J=2.4 Hz, 1H), 10.60-10.80 (brs, 1H).

MS (ESI$^+$) m/z 549 (M+1)

Example 5

Preparation of 3-benzyloxy-7-morpholin-4-yl-4-oxo-4H-pyrido[1,2-a]pyrimidine-2-carboxylic acid [3-(4-fluoro-phenyl)-2-oxo-propyl]-amide

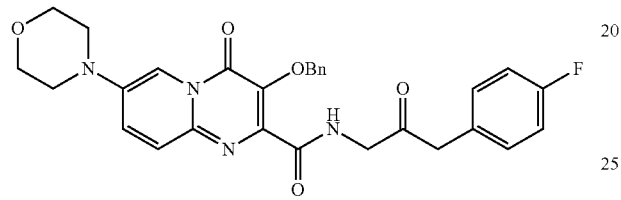

Adapted the procedure of example 2 using 3-benzyloxy-7-morpholin-4-yl-4-oxo-4H-pyrido[1,2-a]pyrimidine-2-carboxylic acid (AU2007001980) as starting material.

$^1$H NMR (300 MHz, CDCl$_3$) δ 3.24 (t, J=4.6 Hz, 4H), 3.77 (s, 2H), 3.91 (t, J=4.6 Hz, 4H), 4.34 (d, J=4.7 Hz, 2H), 5.37 (s, 2H), 7.05 (t, J=8.7 Hz, 2H), 7.22 (dd, J=5.3, 8.3 Hz, 2H), 7.25-7.36 (m, 3H), 7.48-7.62 (m, 3H), 7.70 (d, J=9.7 Hz, 1H), 8.30 (d, J=1.8 Hz, 1H), 8.32-8.40 (brs, 1H).

Example 6

Preparation of 3-benzyloxy-2-[5-(4-fluoro-benzyl)-oxazol-2-yl]-7-morpholin-4-yl-pyrido[1,2-a]pyrimidin-4-one

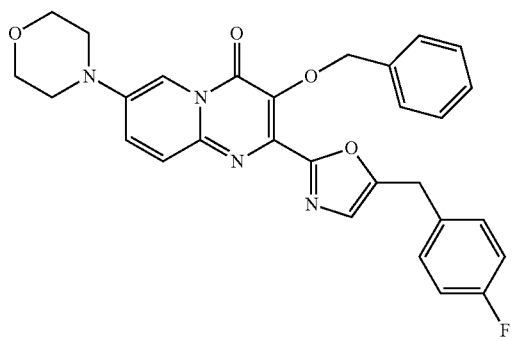

Adapted the procedure of example 3 using the product of example 5 as starting material.

$^1$H NMR (300 MHz, CDCl$_3$) δ 3.25 (t, J=4.6 Hz, 4H), 3.91 (t, J=4.6 Hz, 4H), 4.04 (s, 2H), 5.33 (s, 2H), 6.94-7.05 (m, 3H), 7.20 (dd, J=5.3, 8.3 Hz, 2H), 7.25-7.36 (m, 3H), 7.40-7.50 (m, 2H), 7.58 (dd, J=9.8, 2.6 Hz, 1H), 7.76 (d, J=9.6 Hz, 1H), 8.34 (d, J=2.4 Hz, 1H).

MS (ESI$^+$) m/z 513 (M+1)

Example 7

Preparation of 2-[5-(4-fluoro-benzyl)-oxazol-2-yl]-3-hydroxy-7-morpholin-4-yl-pyrido[1,2-a]pyrimidin-4-one

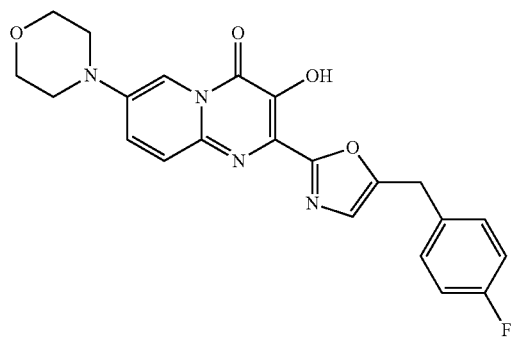

Adapted the procedure of example 4 using the product of example 6 as starting material.

$^1$H NMR (300 MHz, CDCl$_3$) δ 3.16-3.29 (m, 4H), 3.85-3.93 (m, 4H), 4.16 (s, 2H), 6.92 (s, 1H), 7.06 (t, J=8.6 Hz, 2H), 7.26 (? H), 7.45 (dd, J=9.8, 1.8 Hz, 1H), 7.63 (d, J=9.8 Hz, 1H), 8.27 (d, J=1.8 Hz, 1H), 11.03 (s, 1H).

MS (ESI$^+$) m/z 423 (M+1).

Example 8

Preparation of 3-benzyloxy-7-morpholin-4-yl-4-oxo-4H-pyrido[1,2-a]pyrimidine-2-carboxylic acid [3-(4-chloro-phenyl)-2-oxo-propyl]-amide

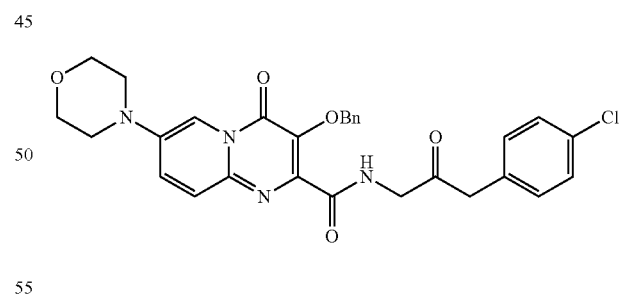

Adapted the procedure of example 2 using 3-benzyloxy-7-morpholin-4-yl-4-oxo-4H-pyrido[1,2-a]pyrimidine-2-carboxylic acid and 1-amino-3-(4-chloro-phenyl)-propan-2-one hydrochloride (AU2007001980) as starting material $^1$H NMR (300 MHz, DMSO-d$^6$): δ 3.20-3.27 (m, 4H), 3.75-3.84 (m, 4H), 3.88 (s, 2H), 4.23 (d, J=5.6 Hz, 2H), 5.14 (s, 2H), 7.19-7.25 (d, J=8.5 Hz, 2H), 7.30-7.41 (m, 5H), 7.48-7.53 (m, 2H), 7.69 (d, J=10.0 Hz, 1H), 8.04 (dd, J=2.6, 9.8 Hz, 1H), 8.20 (d, 2.4 Hz, 1H), 8.79 (t, J=5.5 Hz, 1H).

MS (ESI$^-$) m/z 545 (M−1)

Example 9

Preparation of 3-benzyloxy-2-[5-(4-chloro-benzyl)-thiazol-2-yl]-7-morpholin-4-yl-pyrido[1,2-a]pyrimidin-4-one

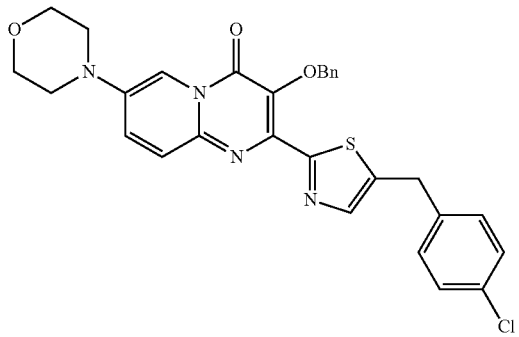

The product from example 8 (0.23 mmol) and Lawensson's Reagent (120 mg, 0.3 mmol) were mixed with toluene (10 mL) and refluxed for 12 h. The reaction mixture was concentrated in vacuo and flash chromatography afforded the titled product.

$^1$H NMR (300 MHz, DMSO-d$^6$): δ 3.17-3.27 (m, 4H), 3.74-3.85 (m, 4H), 4.28 (s, 2H), 5.22 (s, 2H), 7.30-7.45 (m, 7H), 7.49-7.55 (m, 2H), 7.66 (d, J=9.9 Hz, 1H), 7.90 (s, 1H), 8.01 (dd, J=2.7, 9.8 Hz, 1H), 8.15 (d, J=2.5 Hz, 1H).

MS (ESI$^+$) m/z 545 (M+1)

Example 10

Preparation of 2-[5-(4-Chloro-benzyl)-thiazol-2-yl]-3-hydroxy-7-morpholin-4-yl-pyrido[1,2-a]pyrimidin-4-one

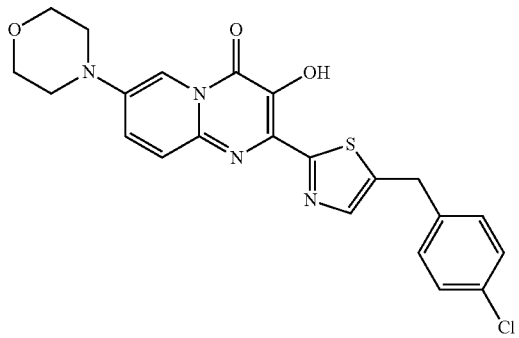

Adapted the procedure of example 4 using the product of example 9 as starting material.

$^1$H NMR (300 MHz, DMSO-d$^6$): δ 3.14-3.23 (m, 4H), 3.74-3.82 (m, 4H), 4.32 (s, 2H), 7.35-7.45 (m, 4H), 7.53 (d, J=9.8 Hz, 1H), 7.83 (dd, J=2.6, 9.6 Hz, 1H), 7.95 (s, 1H), 8.03 (d, J=2.6 Hz, 1H), 11.18-11.32 (brs, 1H).

MS (ESI$^-$) m/z 453 (M−1)

Example 11

Preparation of 3-benzyloxy-7-morpholin-4-yl-4-oxo-4H-pyrido[1,2-a]pyrimidine-2-carboxylic acid amide

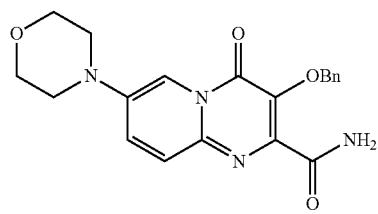

The titled compound was prepared by adapting methods described for example 8.1 of the PCT/AU2007/001980 (Avexa's patent).

$^1$H NMR (300 MHz, DMSO-d$^6$) δ 3.22-3.27 (m, 4H), 3.78-3.83 (m, 4H), 5.16 (s, 2H), 7.33-7.42 (m, 3H), 7.54 (dd, J=8.2, 1.7 Hz, 2H), 7.65-7.70 (m, 2H), 7.89 (s, 1H), 8.02 (dd, J=9.6, 1.8 Hz, 1H), 8.201-8.209 (d, J=1.8 Hz, 1H).

MS (ESI$^+$) m/z 403 (M+23).

Example 12

Preparation of 3-benzyloxy-7-morpholin-4-yl-4-oxo-4H-pyrido[1,2-a]pyrimidine-2-carbothioic acid amide

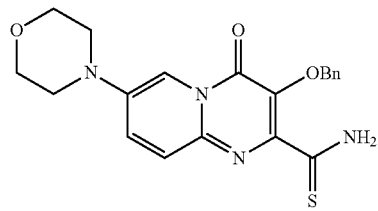

The product of example 11 (50 mg, 0.131 mmol) and Lawesson's reagent (32 mg, 0.079 mmol) were mixed in toluene (5 ml). The mixture was heated at 80-90° C. for 2 h. Then it was cooled down to room temperature and the solvent was removed under reduced pressure. The residue was subjected to column chromatography (CH$_2$Cl$_2$:CH$_3$OH=20:1) to give the titled product (12 mg, yield 24%).

$^1$H NMR (300 MHz, DMSO-d$^6$) 53.21-3.26 (m, 4H), 3.78-3.81 (m, 4H), 5.16 (s, 2H), 7.30-7.45 (m, 3H), 7.52 (dd, J=8.1, 1.8 Hz, 2H), 7.69 (d, J=9.6 Hz, 1H), 8.03 (dd, J=9.6, 2.7 Hz, 1H), 8.20 (d, J=2.6 Hz, 1H), 9.83 (s, 1H), 10.25 (s, 1H).

MS (ESI$^-$) m/z 395 (M−1)

Example 13

Preparation of 3-benzyloxy-7-morpholin-4-yl-4-oxo-4H-pyrido[1,2-a]pyrimidine-2-carboxylic acid methoxy-methyl-amide

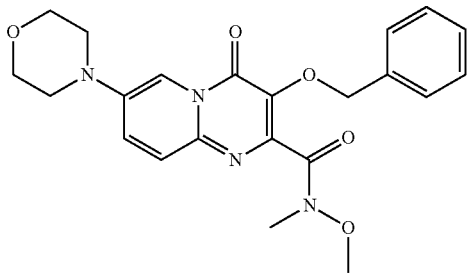

1. N,O-Dimethylhydroxylamine hydrochloride (26 mg, 0.263 mmol) was dissolved in DCM (0.5 mL) and cooled to 0° C. N-methylmorpholine (30 μL, 0.265 mmol) was added and the solution was kept cold for the next step.

2. 3-Benzyloxy-7-morpholin-4-yl-4-oxo-4H-pyrido[1,2-a]pyrimidine-2-carboxylic acid (product of example 5, 100 mg, 0.263 mmol) was dissolved in THF (1 mL) and DCM (11 mL) and cooled to −20° C. N-Methylmorpholine (30 μL, 0.265 mmol) was added and the temperature was raised to −12° C. Ethyl chloroformate was added and after 2 minutes, the solution of dimethylhydroxylamine. The reaction was warmed to room temperature and stirred for one hour. After this time, the mixture was quenched by addition of 0.2 M HCl. The layers were separated and the organic layer was washed sequentially with 0.2 M HCl, 0.5 M NaOH (2×) and brine. Then dried and concentrated. The product was isolated as a yellow solid (112 mg, 100% yield) and was used without further purification.

$^1$H NMR (300 MHz, CDCl$_3$): 8.39 (1H, s, Ar—CH), 7.70-7.51 (4H, m, Ar—CH), 7.40-7.31 (3H, m, Ar—CH), 5.30 (2H, s, CH$_2$Ar), 3.91 (4H, t, J=4.5 Hz, CH$_2$OCH$_2$), 3.61 (3H, s, OCH$_3$), 3.37 (3H, s, CH$_3$N), 3.25 (4H, t, J=4.5 Hz, CH$_2$NCH$_2$).

MS m/z 425 [M+H]$^+$

Example 14

Preparation of 3-benzyloxy-7-morpholin-4-yl-4-oxo-4H-pyrido[1,2-a]pyrimidine-2-carbaldehyde

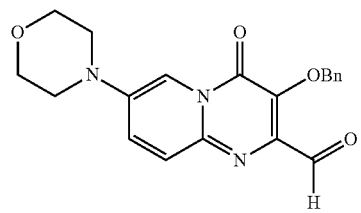

3-Benzyloxy-7-morpholin-4-yl-4-oxo-4H-pyrido[1,2-a]pyrimidine-2-carboxylic acid methoxy-methyl-amide (product of example 14, 112 mg, 0.264 mmol) was dissolved in THF (1 mL) and added to a stirred solution of LAH (14 mg, 0.369 mmol) in THF at −45° C. The reaction was warmed to room temperature and stirred for 2 days. After this time, the reaction was quenched by addition of water and the residue filtered through celite, washing with ether. The combined organic layers where extracted with 1M HCl. The aqueous layer was basified with saturated aqueous bicarbonate solution and extracted with EtOAc. The combined organic layers were washed with water and brine, then dried and concentrated. Purification was achieved by column chromatography to afford the product (25 mg, 26% yield) as a yellow solid.

$^1$H NMR (300 MHz, CDCl$_3$): 10.3 (1H, s, CHO), 8.32 (1H, d, J=3.0 Hz, Ar—CH), 7.75 (1H, d, J=9.9 Hz, Ar—CH), 7.58 (1H, dd, J=9.9, 2.7 Hz, Ar—CH), 7.45-7.42 (2H, m, Ar—CH), 7.38-7.34 (3H, m, Ar—CH), 5.50 (2H, s, CH$_2$Ar), 3.92 (4H, t, J=4.5 Hz, CH$_2$OCH$_2$), 3.27 (4H, t, J=4.5 Hz, CH$_2$NCH$_2$).

MS m/z 366 [M+H]$^+$

Example 15

Preparation of 3-benzyloxy-7-morpholin-4-ylmethyl-4-oxo-4H-pyrido[1,2-a]pyrimidine-2-carboxylic acid hydrazide

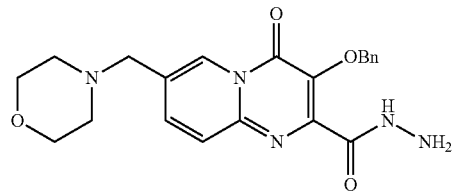

To a solution of 3-benzyloxy-7-morpholin-4-ylmethyl-4-oxo-4H-pyrido[1,2-a]pyrimidine-2-carboxylic acid methyl ester (AU2007001980) (1 g, 2.44 mmol) in methanol (15 ml), hydrazine hydrate (1.44 g, 85% content, 24.4 mmol) was added at room temperature. The mixture was stirred for 1 hour. After most of the solvent was evaporated under reduced pressure, 15 ml of water was added. The mixture was extracted with dichloromethane three times, and the extracts were washed with brine, dried over anhydrous sodium sulfate and concentrated to dryness to give the titled product (807 mg, 80.7%).

$^1$H NMR (300 MHz, DMSO-d$^6$) δ 2.43 (t, J=4.5 Hz, 4H), 3.57-3.63 (m, 6H), 4.55 (d, J=3.6 Hz, 2H), 5.14 (s, 2H), 7.30-7.54 (m, 5H), 7.69 (dd, J=9.0 Hz, 1.1 Hz, 1H), 7.87 (dd, J=9.0 Hz, 2.1 Hz, 1H), δ 8.84 (dd, J=1.1, 2.1 Hz, 1H), δ 9.63 (s, 1H).

MS (ESI$^-$) m/z 408 (M−1)

Example 16

Preparation of 3-benzyloxy-7-morpholin-4-ylmethyl-4-oxo-4H-pyrido[1,2-a]pyrimidine-2-carboxylic acid N'-[2-(4-fluoro-phenyl)-acetyl]-hydrazide

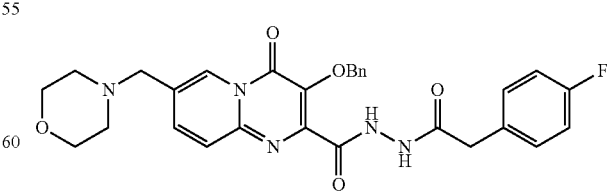

To a mixture of the product of example 15 (807 mg, 1.97 mmol) and sodium carbonate (418 mg, 3.95 mmol) in tetrahydrofuran (25 ml), 4-fluorophenylacetyl chloride (374 mg, 2.17 mmol) was added drop-wise. The resulting mixture was stirred overnight at room temperature. Then water (25 ml) was added and the mixture was stirred for 1 hour. The resulting solids were collected by filtration, washed with water and PE successively and dried to give the titled product (697 mg, 64.8%).

$^1$H NMR (300 MHz, DMSO-d$^6$) δ 2.43 (t, J=3.6 Hz, 4H), 3.55-3.63 (m, 8H), 5.16 (s, 2H), 7.12-7.20 (m, 2H), δ 7.29-7.41 (m, 5H), 7.54 (dd, J=8.0 Hz, 1.5 Hz, 2H), δ 7.71 (dd, J=9.0 Hz, 0.9 Hz, 1H), δ 7.88 (dd, J=9.0 Hz, 1.8 Hz, 1H), δ 8.85 (dd, J=1.8, 0.9 Hz, 1H), 10.44 (s, H), 10.52 (s, 1H)

MS (ESI$^-$) m/z 544 (M−1)

Example 17

Preparation of 3-benzyloxy-2-[5-(4-fluoro-benzyl)-[1,3,4]oxadiazol-2-yl]-7-morpholin-4-ylmethyl-pyrido[1,2-a]pyrimidin-4-one

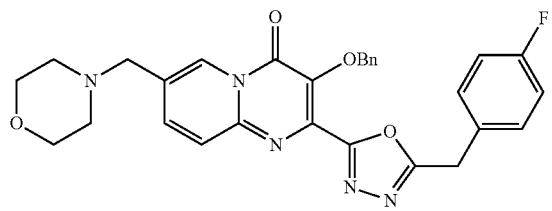

The product of example 16 (250 mg, 0.46 mmol), carbon tetrachloride (354 mg, 2.3 mmol) and triethylamine (116 mg, 1.15 mmol) were mixed in acetonitrile (15 ml). To the above mixture was added triphenylphosphine (302 mg, 1.15 mmol) at room temperature and stirred overnight. Then water (50 ml) was added and the mixture was extracted with dichloromethane three times. The combined organic layers were washed with brine, dried over anhydrous sodium sulfate and evaporated into dryness. The residue was subjected to silica gel chromatography using PE-ethyl acetate (1:4 v/v) as eluent to give the titled product (195 mg, 80.7%).

$^1$H NMR (300 MHz, DMSO-d$^6$) δ 2.45 (t, J=4.5 Hz, 4H), 3.57-3.65 (m, 6H), 4.39 (s, 2H), 5.22 (s, 2H), 7.15-7.25 (m, 2H), 7.27-7.45 (m, 7H), 7.74 (d, J=9.0 Hz, 1H), 7.88 (d, J=9.0 Hz, 1H), 8.85 (s, 1H)

MS (ESI$^-$) m/z 526 (M−1)

Example 18

2-[5-(4-Fluoro-benzyl)-[1,3,4]oxadiazol-2-yl]-3-hydroxy-7-morpholin-4-ylmethyl-pyrido[1,2-a]pyrimidin-4-one

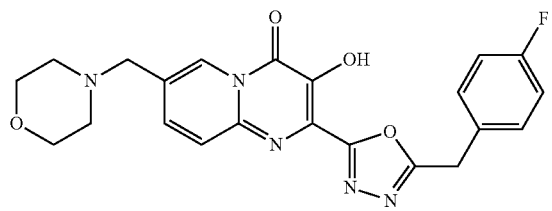

To a solution of the product of example 17 (34 mg, 0.065 mmol) in acetonitrile (7 ml), TMSI (0.08 ml, 0.516 mmol) was added dropwise in the presence of N$_2$ at room temperature and then stirred at room temperature for 2 hours. Methanol (5 ml) was added to quench the reaction. Then the mixture was poured into water (15 ml) and 0.5 N sodium hydroxide solution was added dropwise to adjust the pH 8-9. The mixture was extracted with dichloromethane three times. The combined extracts were washed with aqueous sodium bisulfite and water, dried over anhydrous sodium sulfate and evaporated into dryness. The residue was recrystallized for a mixed solvent of DCM/PE to give the titled product (18 mg, 63.8%). $^1$H NMR (300 MHz, DMSO-d$^6$) δ 2.43 (t, J=4.5 Hz, 4H), 3.54-3.62 (m, 6H), 4.43 (s, 2H), 7.16-7.25 (m, 2H), 7.39-7.46 (m, 2H), 7.59-7.68 (m, 2H), 8.66 (s, 1H), 10.55 (brs, 1H).

MS (ESI$^-$) m/z 436 (M−1)

HPLC: 98.2%

Example 19

Preparation of 3-benzyloxy-7-morpholin-4-yl-4-oxo-4H-pyrido[1,2-a]pyrimidine-2-carbonitrile

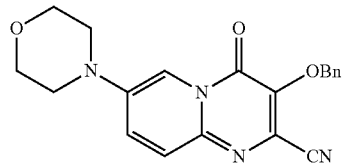

To a solution of the product of example 11 (32 mg, 0.079 mmol) in DMF (1.0 ml), cyanuric chloride (16.0 mg, 0.087 mmol) was added at room temperature. The mixture was stirred for 2 hour and then poured into water (10 ml). The resulting solids were collected by filtration and dried in vacuo to give the titled product (27 mg, yield 88.4%).

$^1$H NMR (300 MHz, DMSO) δ 8.16 (d, J=2.6 Hz, 1H), 8.07 (dd, J=2.7, 9.9 Hz, 1H), 7.70 (d, J=9.7 Hz, 1H), 7.46 (dd, J=2.1, 8.2 Hz, 2H), 7.41-7.33 (m, 3H), 5.38 (s, 2H), 3.78 (t, J=4.3 Hz, 4H), 3.25 (t, J=4.7 Hz, 4H)

MS (ESI$^+$) m/z 363 (M+1)

Example 20

Preparation of 3-benzyloxy-N-hydroxy-7-morpholin-4-yl-4-oxo-4H-pyrido[1,2-a]pyrimidine-2-carboxamidine

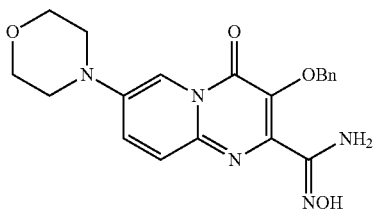

The product of example 10 (1.10 g, 3.04 mmol) was dissolved EtOH (10 ml). To the above solution was added NH$_2$OH.HCl (1.07 g, 15.2 mmol) and saturated aqueous solution of NaHCO$_3$ (1.28 g, 15.2 mmol), and then the mixture was heated at reflux for 4 hours. After cooled to room temperature, the solids were collected by filtration, washed with ethanol and dried to give the titled product (1.11 g, yield 92.0%).

¹H NMR (300 MHz, DMSO) δ 9.86 (s, 1H), 8.17 (d, J=2.4 Hz, 1H), 8.00 (dd, J=2.5, 9.6 Hz, 1H), 7.65 (d, J=9.8 Hz, 1H), 7.56 (dd, J=1.7, 8.2 Hz, 2H), 7.41-7.31 (m, 3H), 5.77 (s, 2H), 5.09 (s, 2H), 3.79 (t, J=4.6 Hz, 4H), 3.22 (t, J=4.8 Hz, 4H).

Example 21

Preparation of 3-benzyloxy-N-[2-(4-fluoro-phenyl)-acetoxy]-7-morpholin-4-yl-4-oxo-4H-pyrido[1,2-a]pyrimidine-2-carboxamidine

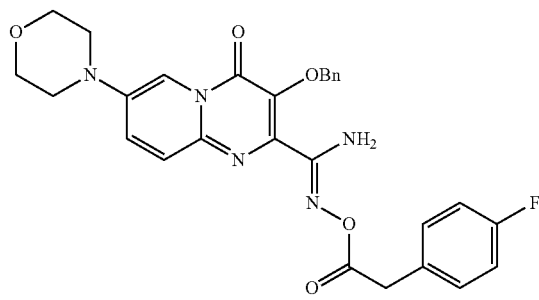

The product of example 20 (200 mg, 0.51 mmol) and 4-fluorophenylacetyl chloride (0.073 mL, 0.53 mmol) were dissolved in THF (5 ml). To this solution was added TEA (0.14 mL, 1.02 mmol) dropwise at 0° C. The mixture was stirred at room temperature overnight and then poured into water (30 ml). The crude product was obtained by filtration. It was recrystallized from CH₂Cl₂/PE to give the titled product (261 mg, yield 97.0%)

¹H NMR (300 MHz, DMSO) δ 8.20 (d, J=2.6 Hz, 1H), 8.03 (dd, J=2.5, 9.9 Hz, 1H), 7.69 (d, J=9.9 Hz, 1H), 7.52-7.47 (m, 2H), 7.38 (dd, J=5.6, 8.7 Hz, 2H), 7.35-7.28 (m, 3H), 7.17 (t, J=8.8 Hz, 2H), 7.02-6.92 (brs, 2H), 5.12 (s, 2H), 3.81-3.75 (m, 6H), 3.23 (t, J=4.8 Hz, 4H)

Example 22

Preparation of 3-benzyloxy-2-[5-(4-fluoro-benzyl)-[1,2,4]oxadiazol-3-yl]-7-morpholin-4-yl-pyrido[1,2-a]pyrimidin-4-one

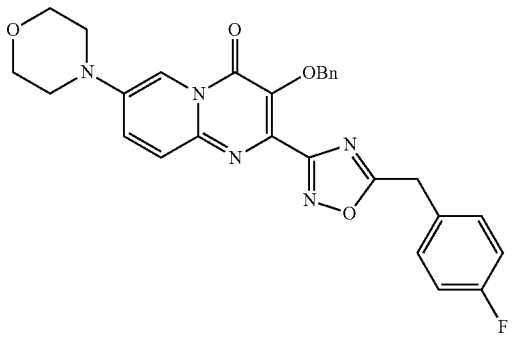

The solution of the product of example 21 (261 mg, 0.49 mmol) in toluene (5 ml) was heated at reflux for 2 h. After cooled to room temperature, the solids were collected by filtration, washed with diethyl ether and dried to give the titled product (190 mg, yield 75.3%).

¹H NMR (300 MHz, DMSO) δ 8.22 (d, J=2.6 Hz, 1H), 8.04 (dd, J=2.9, 9.9 Hz, 1H), 7.71 (d, J=9.9 Hz, 1H), 7.46 (dd, J=5.5, 8.8 Hz, 2H), 7.37-7.27 (m, 5H), 7.21 (t, J=8.8 Hz, 2H), 5.15 (s, 2H), 4.47 (s, 2H), 3.80 (t, J=4.5 Hz, 4H), 3.25 (t, J=4.5 Hz, 4H)

Example 23

Preparation of 2-[5-(4-fluoro-benzyl)-[1,2,4]oxadiazol-3-yl]-3-hydroxy-7-morpholin-4-yl-pyrido[1,2-a]pyrimidin-4-one

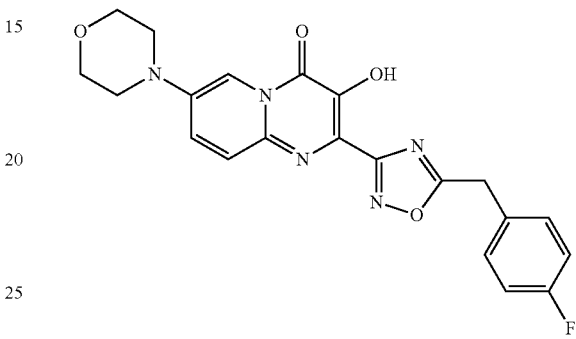

To a solution of the product of example 22 (40 mg, 0.078 mmol) in dichloromethane (5 ml) was added FeCl₃ (38 mg, 0.234 mmol), and the mixture was stirred at room temperature for 30 min. Then 1M HCl (8 ml) was added and the mixture was extracted with dichloromethane three times. The combined extracts were washed with water and brine, dried and evaporated into dryness. The residue was recrystallized from CH₂Cl₂/MeOH to give the titled products (10 mg, yield 30.3%).

¹H NMR (300 MHz, DMSO) δ 10.13 (s, 1H), 8.00 (d, 2.3 Hz, 1H), 7.82 (dd, J=2.3, 9.7 Hz, 1H), 7.58 (d, J=9.8 Hz, 1H), 7.46 (dd, J=5.6, 8.8 Hz, 2H), 7.22 (t, J=8.8 Hz, 2H), 4.46 (s, 2H), 3.77 (t, J=4.7 Hz, 4H), 3.19 (t, J=4.9 Hz, 4H)

MS (ESI⁺) m/z 424 (M+1)

HPLC 98.1%

Example 24

Preparation of 3-benzyloxy-2-[5-(3,4-dichloro-benzyl)-[1,2,4]oxadiazol-3-yl]-7-morpholin-4-yl-pyrido[1,2-a]pyrimidin-4-one

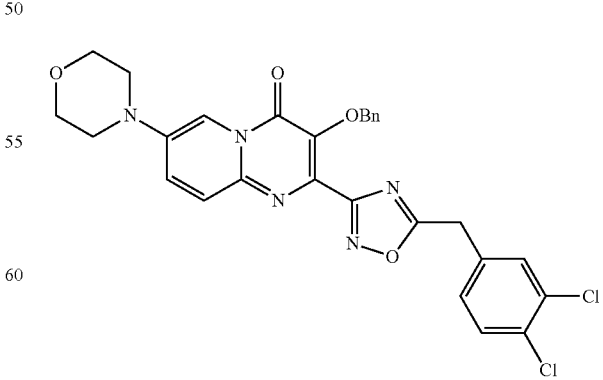

Using the product of example 20 and 3,4-dichlorophenylacetyl chloride following the procedure of example 21.

¹H NMR (300 MHz, DMSO) δ 8.21 (d, J=2.6 Hz, 1H), 8.05 (dd, J=2.8, 9.9 Hz, 1H), 7.77-7.62 (m, 3H), 7.42 (dd, J=1.9, 8.4 Hz, 1H), 7.36-7.25 (m, 5H), 5.14 (s, 2H), 4.52 (s, 2H), 3.80 (t, J=4.5 Hz, 4H), 3.25 (t, J=4.6 Hz, 4H)

MS (ESI⁻) m/z 562 (M−1)

Example 25

Preparation of 2-[5-(3,4-dichloro-benzyl)-[1,2,4]oxadiazol-3-yl]-3-hydroxy-7-morpholin-4-yl-pyrido[1,2-a]pyrimidin-4-one

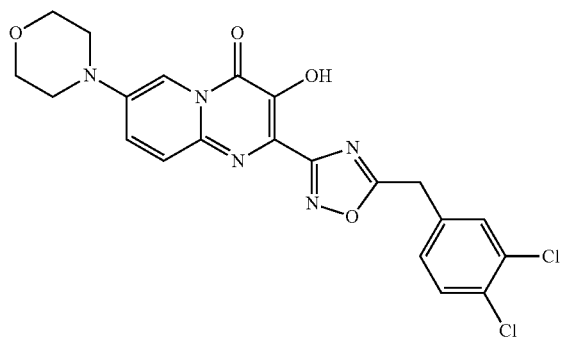

Adapted the procedure for example 23 using the product of example 24 as starting material.

¹H NMR (300 MHz, CDCl₃) δ 8.44 (s, 1H), 8.15-8.23 (m, 1H), 7.71 (d, J=10.0 Hz, 1H), 7.40-7.55 (m, 3H), 7.20-7.30 (1H), 4.37 (s, 2H), 3.86-3.96 (m, 4H), 3.15-3.32 (m, 4H)

MS (ESI⁺) m/z 474 (M+1)

HPLC 96.4%

Example 26

Preparation of (4-chloro-3-fluoro-phenyl)-acetonitrile

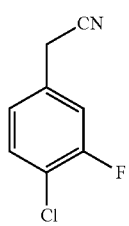

To a boiling solution of 4-chloro-3-fluororobenzyl bromide (10 g, 44.8 mmol) in absolute ethanol (40 ml) was added a solution of potassium cyanide (2.9 g, 44.8 mmol) in water (6 ml). The mixture was refluxed for 1.5 hours, then most of the ethanol was distilled off under reduced pressure and the cooled residue poured into water. The solution was extracted three times with ether. The combined organic layers were washed with brine, dried and concentrated into dryness to give the titled product (7.8 g, 93% yield)

¹H NMR (300 MHz, DMSO-d⁶) 4.09 (s, 2H), 7.25 (ddd, J=0.8, 2.0, 8.2 Hz, 1H), 7.43 (dd, J=2.0, 10.0 Hz, 1H), 7.64 (t, J=8.2 Hz, 1H).

MS (ESI⁻) m/z 168 (M−1)

Example 27

Preparation of (4-chloro-3-fluoro-phenyl)-acetic acid

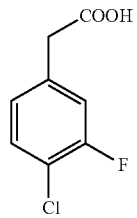

A mixture of the product of example 26 (7.8 g, 0.046 mol), water (7.5 ml), concentrated sulfuric acid (7.5 ml) and acetic acid (7.5 ml) was heated at reflux for 2 hours. After being cooled to room temperature, the mixture was poured into ice-water. The resulting solids were collected by filtration and washed by diethyl ether to give the titled product (6.8 g, 79%)

¹H NMR (300 MHz, DMSO-d⁶) 3.64 (s, 2H), 7.14 (ddd, J=0.6, 2.1, 8.2 Hz, 1H), 7.34 (dd, J=2.1, 10.6 Hz, 1H), 7.52 (t, J=8.1 Hz, 1H).

MS (ESI⁻) m/z 187 (M−1)

Example 28

Preparation of (4-chloro-3-fluoro-phenyl)-acetyl chloride

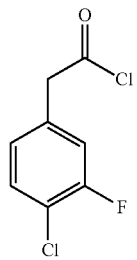

A mixture of the product of example 28 (4.9 g, 26 mmol) with thionyl chloride (50 ml) was refluxed for 3 hours. Then thionyl chloride was removed under reduced pressure. The residue was redistilled under reduced pressure to give crude titled acyl chloride, which was used directly in the next step reaction. (3.2 g, 60% yield)

Example 29

Preparation of 5-(4-chloro-3-fluoro-benzyl)-oxazole-4-carboxylic acid ethyl ester

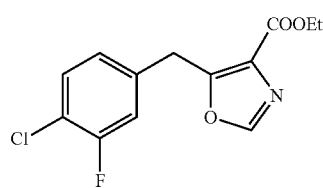

To a solution of potassium tert-butoxide (3.5 g, 31.25 mmol) in THF (50 ml) was added ethyl isocyanoacetate (3.5 g, 31.25 mmol) dropwise at 5° C. After stirring for 45 minutes, the product of example 28 (3.2 g, 15.5 mmol) was added dropwise. Then the mixture was stirred overnight at room temperature. The reaction mixture was filtered and the filtrate was concentrated. The residue was purified by column chromatography (PE/EA=5/1) to give the titled compound (2.5 g, 67.7 yield)

$^1$H NMR (300 MHz, DMSO-d$^6$) 1.29 (t, J=7.1 Hz, 3H), 4.30 (q, J=7.1 Hz, 2H), 4.41 (s, 2H), 7.11 (ddd, J=0.6, 2.1, 8.3 Hz, 1H), 7.34 (dd, J=2.0, 10.4 Hz, 1H), 7.54 (t, J=8.1 Hz, 1H), 8.40 (s, 1H).

MS (ESI$^+$) m/z 306 (M+23)

Example 30

Preparation of 1-amino-3-(4-chloro-3-fluoro-phenyl)-propan-2-one hydrochloride

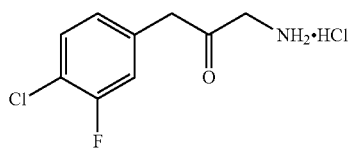

A mixture of the product of example 29 (2.5 g, 10.53 mmol) with hydrochloride acid (6 mol/l, 30 ml) was refluxed for about 3 hours and then cooled to room temperature. The solids were collected by filtration, washed with EA and dried to give the titled product (1.7 g, 81%)

$^1$H NMR (300 MHz, DMSO-d$^6$) 3.96 (s, 2H), 4.03 (s, 2H), 7.10 (dd, J=1.9, 8.2 Hz, 1H), 7.29 (d, J=1.9, 10.4 Hz, 1H), 7.56 (t, J=8.1 Hz, 1H), 8.15-8.42 (brs, 3H).

MS (ESI$^+$) m/z 202 (M+1)

Example 31

Preparation of 5-fluoro-2,N,N-trimethyl-benzenesulfonamide

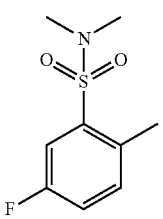

A mixture of 5-fluoro-2-methylbenzene sulfonylchloride (2.1 mL, 14.3 mmol) in THF (18 mL) and 2 M dimethylamine in methanol (18 mL), was stirred at room temperature for 0.5 h. The resulting mixture was concentrated under reduced pressure to give a crude product as a mixture of white solid and colourless oil. The crude product was purified by column (30% EtOAc in Hexane) to give the titled compound as a colourless oil (3.09 g, 99% yield).

Example 32

Preparation of 2-bromomethyl-5-fluoro-N,N-dimethyl-benzenesulfonamide

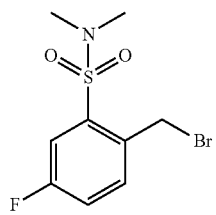

To a solution of the product of example 31 (3 g, 13.8 mmol) in DCE (40 mL), was added n-bromosuccinamide (2.8 g, 15.19 mmol) and stirred at 80° C. for 5 min before AIBN (300 mg, 0.016 mmol) was added and heated at 80° C. for 5 h (95% conversion). The reaction mixture was concentrated under reduced pressure to give a crude product as a yellow solid. The crude product was purified by column (10-20% ethylacetate in hexane) to give the titled product. (50% yield)

MS (ESI$^+$) m/z 296, 298 Br [M+H$^+$]

Example 33

Preparation of 2-cyanomethyl-5-fluoro-N,N-dimethyl-benzenesulfonamide

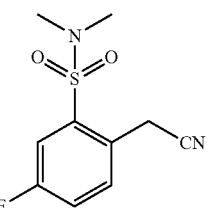

A mixture of the product of example 32 (~90% pure, 729 mg, 2.46 mmol) in a mixture of DMF:H$_2$O (3 mL:2 mL) and sodium cyanide (362 mg, 7.4 mmol) was stirred at room temperature overnight. The resulting mixture was quenched with saturated NaHCO$_3$ (12 mL) and extracted with ethylacetate (3×30 mL). The extracts were combined and washed with saturated NaCl (2×30 mL) and water (2×30 mL). The organic layer was separated, dried over anhydrous MgSO$_4$ and concentrated under reduced pressure to give the titled product as a colourless oil (503 mg, 85% yield).

$^1$H NMR CDCl$_3$, 300 MHz: δ 2.86 (s, 6H, —N(CH$_3$)$_2$), 4.19 (s, 2H, —CH$_2$C≡N), 7.35 (m, 1H, ArH), 7.69 (m, 2H, ArH).

MS (ESI$^+$) m/z 243 [M+H$^+$], 265 [M+Na$^+$]

Example 34

Preparation of (2-dimethylsulfamoyl-4-fluoro-phenyl)-acetic acid

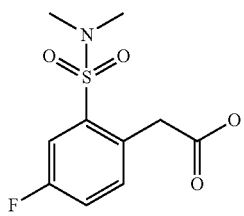

A solution of the product of example 33 (300 mg, 1.24 mmol) in 4M HCl in dioxane (14 mL) was heated at 40° C. for 2 h. The reaction mixture was concentrated under reduced pressure to give the title compound as a yellow oil and was used without further purification.

MS (ESI$^+$) m/z 261 [M$^+$]

Example 35

Preparation of 1-chloro-3-(4-fluoro-phenyl)-propan-2-one

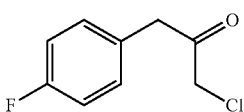

1. To a chilled (0° C.) solution of 4-fluoro-phenylacetyl chloride (14.07 mmol, 2.43 g) in diethylether (15 mL), was added a cold solution of freshly distilled diazomethane in diethylether (16 mmol) and stirred at 0° C. for 15 min and then at room temperature for 15 min. The resulting mixture of diazoketone was used in the next step without further purification (confirmed by mass spec).

2. One third of the above diazoketone solution (in diethyl ether) was cooled to −30° C. and 4M HCl in dioxane (3 mL) was added and stirred at −30° C. for 0.5 h and then at room temperature for 0.5 h. The reaction mixture was quenched with water (20 mL) and extracted with ethyl acetate (30 mL). The organic layer was separated and dried over anhydrous MgSO$_4$ and concentrated under reduced pressure to give a crude product as slightly yellow oil. The crude product was purified by column chromatography (15-20% EtOAc in hexane) to give the titled compound with R$_f$=0.016 (200 mg, 19% yield)

$^1$H NMR: CDCl$_3$, 300 MHz: δ 3.88 (s, 2H, —CH$_2$Cl), 4.11 (s, 2H, —CH$_2$(C=O)), 7.04 (t, J=8.7 Hz, 2H, ArH), 7.20 (t, dd=4.8, 8.8 Hz, 2H, ArH).

Example 36

Preparation of 2-[3-(4-fluoro-phenyl)-2-oxo-propyl]-isoindole-1,3-dione

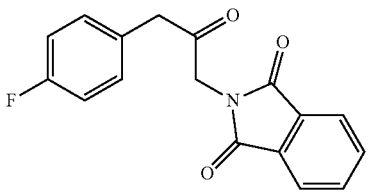

To a solution of the product of example 35 (85 mg, 0.45 mmol) in DMF (1 mL), under a nitrogen atmosphere, was added potassium salt of phthalamide (96 mg, 0.52 mmol). The resulting mixture was stirred at room temperature for 1 h. The reaction mixture was quenched with a mixture of ice-water and filtered. The slightly pink solid was washed with water to give the titled compound as a white product (79 mg, 62% yield).

$^1$H NMR CDCl$_3$, 300 MHz: δ 3.82 (s, 2H, —CH$_2$N—), 4.51 (s, 2H, —CH$_2$(C=O)), 7.04 (m, 2H, ArHF), 7.23 (m, 2H, ArHF), 7.74 (m, 2H, ArH), 7.86 (m, 2H, ArH).

MS (ESI$^+$) m/z 298 [M+H$^+$]

Example 37

Preparation of 2-[5-(3,4-Dichloro-benzyl)-[1,3,4]oxadiazol-2-yl]-3-hydroxy-7-morpholin-4-yl-pyrido[1,2-a]pyrimidin-4-one This example corresponds to Example 9.6 in International Patent Application No. PCT/AU2007/001980.

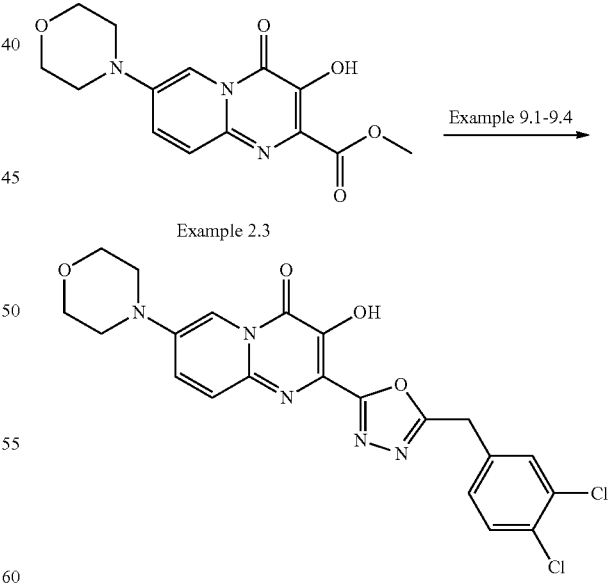

Using the starting material prepared in Example 2.3 of International Patent Application No. PCT/AU2007/001980, the procedure described in Example 9.1-9.4 of International Patent Application No. PCT/AU2007/001980, was adapted to prepare 2-[5-(3,4-dichloro-benzyl)-[1,3,4]oxadiazol-2-yl]-3-hydroxy-7-methyl-pyrido[1,2-c]pyrimidin-4-one.

¹H NMR (300 MHz, DMSO-d⁶) δ 3.18-3.24 (m, 4H), 3.75-3.83 (m, 4H), 4.47 (s, 2H), 7.40 (dd, J=8.3, 2.0 Hz, 1H), 7.61 (d, J=9.8 Hz, 1H), 7.65 (d, J=8.5 Hz, 1H), 7.72 (d, J=2.0 Hz, 1H), 7.85 (dd, J=9.9, 2.5 Hz, 1H), 8.01 (d, J=2.5 Hz, 1H), 10.41 (s, 1H)

HPLC$_{method\ 7}$ 94.1%/17.2 min

Example 38

Preparation of 2-[5-(4-Fluoro-benzyl)-[1,3,4]oxadiazol-2-yl]-3-hydroxy-7-morpholin-4-yl-pyrido[1,2-a]pyrimidin-4-one This example corresponds to Example 9.7 in International Patent Application No. PCT/AU2007/001980.

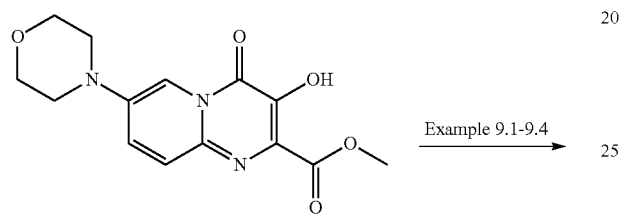

Example 2.3

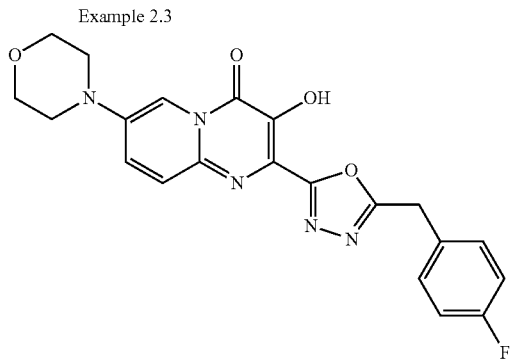

Using the starting material prepared in Example 2.3 of International Patent Application No. PCT/AU2007/001980, the procedure described in Example 9.1-9.4 of International Patent Application No. PCT/AU2007/001980, was adapted to prepare 2-[5-(4-fluoro-benzyl)-[1,3,4]oxadiazol-2-yl]-3-hydroxy-7-methyl-pyrido[1,2-a]pyrimidin-4-one.

¹H NMR (300 MHz, DMSO-d⁶) δ 3.20 (t, J=4.8 Hz, 4H), 3.79 (t, J=4.8 Hz, 4H), 4.42 (s, 2H), 7.21 (t, J=9.0 Hz, 2H), 7.43 (dd, J=8.8, 5.5 Hz, 2H), 7.61 (d, J=9.9 Hz, 1H), 7.85 (dd, J=9.8, 2.5 Hz, 1H), 8.00 (d, J=2.5 Hz, 1H), 10.39 (s, 1H).

MS (ESI⁻) m/z 422 (M−1)

HPLC$_{method\ 7}$ 94.1%/14.7 min

Example 39

Preparation of 2-[5-(3,4-Dichloro-benzyl)-[1,3,4]thiadiazol-2-yl]-3-hydroxy-7-morpholin-4-yl-pyrido[1,2-a]pyrimidin-4-one This example corresponds to Example 10.4 in International Patent Application No. PCT/AU2007/001980.

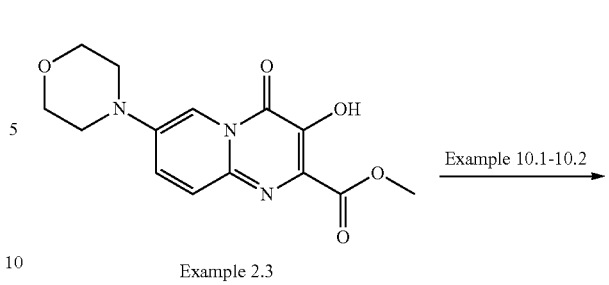

Example 2.3

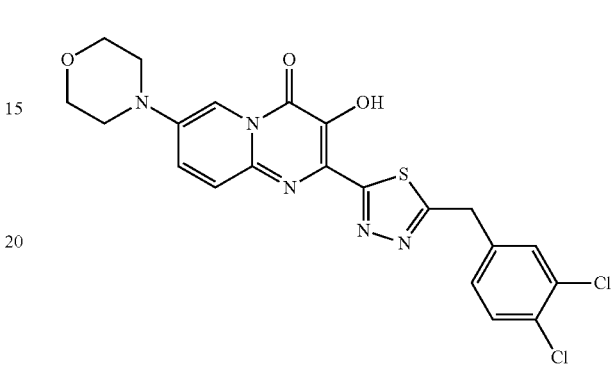

Using the starting material prepared in Example 2.3 of International Patent Application No. PCT/AU2007/001980, the procedure described in Example 10.1-10.2 of International Patent Application No. PCT/AU2007/001980, was adapted to prepare 2-[5-(3,4-dichloro-benzyl)-[1,3,4]thiadiazol-2-yl]-3-hydroxy-7-morpholin-4-yl-pyrido[1,2-a]pyrimidin-4-one ¹H NMR (300 MHz, DMSO-d⁶) δ 3.15-3.25 (m, 4H), 3.70-3.85 (m, 4H), 4.60 (s, 2H), 7.42 (dd, J=8.2 Hz, 2.1 Hz, 1H), 7.60 (d, J=9.8 Hz, 1H), 7.65 (d, J=8.2 Hz, 1H), 7.74 (d, J=2.1 Hz, 1H), 7.86 (dd, J=9.8 Hz, 2.5 Hz, 1H), 8.01 (d, J=2.3 Hz, 1H), 10.50-11.10 (brs, 1H)

MS (ESI⁻) m/z 488 (M−1)

HPLC$_{method\ 7}$ 97.6%/19.3 min

Example 40

Preparation of 2-[5-(4-Fluoro-benzyl)-[1,3,4]thiadiazol-2-yl]-3-hydroxy-7-morpholin-4-yl-pyrido[1,2-a]pyrimidin-4-one This example corresponds to Example 10.5 in International Patent Application No. PCT/AU2007/001980.

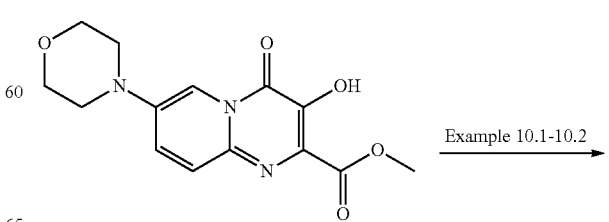

Example 2.3

-continued

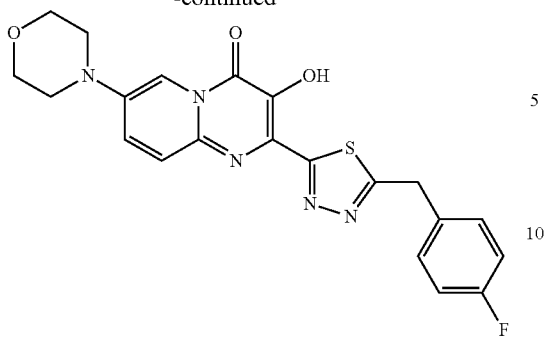

Using the starting material prepared in Example 2.3 of International Patent Application No. PCT/AU2007/001980, the procedure described in Example 9.1-9.4 of International Patent Application No. PCT/AU2007/001980, was adapted to prepare 2-[5-(4-fluoro-benzyl)-[1,3,4]thiadiazol-2-yl]-3-hydroxy-7-morpholin-4-yl-pyrido[1,2-a]pyrimidin-4-one $^1$H NMR (300 MHz, DMSO-d$^6$) δ 3.20 (t, J=4.8 Hz, 4H), 3.78 (t, J=4.8 Hz, 4H), 4.56 (s, 2H), 7.21 (t, J=8.8 Hz, 2H), 7.47 (dd, J=8.8 Hz, 5.5 Hz, 2H), 7.59 (d, J=9.8 Hz, 1H), 7.85 (dd, J=9.9 Hz, 2.7 Hz, 1H), 8.01 (d, J=2.6 Hz, 1H), 10.80 (s, 1H)

MS (ESI$^-$) m/z 438 (M−1)
HPLC$_{method\ 7}$ 94.1%/14.2 min

Example 41

Preparation of 2-[5-(4-Fluoro-benzyl)-thiazol-2-yl]-3-hydroxy-7-morpholin-4-yl-pyrido[1,2-a]pyrimidin-4-one This example corresponds to Example 13.5 in International Patent Application No. PCT/AU2007/001980.

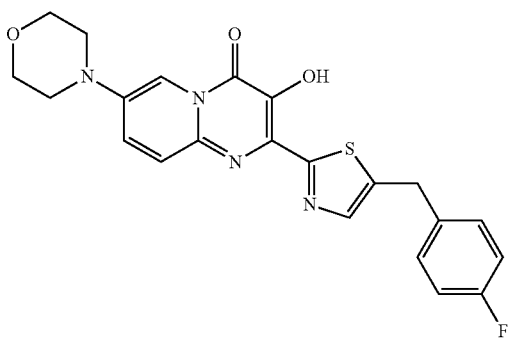

Using the materials from Example 2.3 and Example 12.7 of International Patent Application No. PCT/AU2007/001980, and adapting the procedures from Examples 13.1 to 13.2 of International Patent Application No. PCT/AU2007/001980, afforded 2-[5-(4-fluoro-benzyl)-thiazol-2-yl]-3-hydroxy-7-morpholin-4-yl-pyrido[1,2-c]pyrimidin-4-one $^1$H NMR (300 MHz, DMSO-d$^6$) δ 3.14-3.21 (m, 4H), 3.74-3.81 (m, 4H), 4.31 (s, 2H), 7.18 (t, J=8.9 Hz, 2H), 7.39 (dd, J=8.8 Hz, 5.5 Hz, 2H), 7.53 (d, J=9.9 Hz, 1H), 7.83 (dd, J=9.9 Hz, 2.6 Hz, 1H), 7.95 (s, 1H), 8.04 (d, J=2.5 Hz, 1H), 11.25 (s, 1H)

MS (ESI$^+$) m/z 461 (M+Na$^+$)
HPLC$_{method\ 7}$ 86.3%/19.6 min

Example 42

Preparation of 2-[5-(3,4-Dichloro-benzyl)-thiazol-2-yl]-3-hydroxy-7-morpholin-4-yl-pyrido[1,2-a]pyrimidin-4-one This example corresponds to Example 13.6 in International Patent Application No. PCT/AU2007/001980.

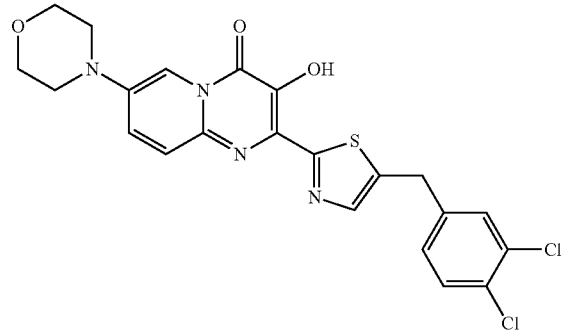

Using the materials from Example 2.3 and Example 12.8 of International Patent Application No. PCT/AU2007/001980 and adapting the procedures from Examples 13.1 to 13.2 of International Patent Application No. PCT/AU2007/001980 afforded 2-[5-(3,4-dichloro-benzyl)-thiazol-2-yl]-3-hydroxy-7-morpholin-4-yl-pyrido[1,2-a]pyrimidin-4-one.

$^1$H NMR (300 MHz, DMSO-d$^6$) δ 3.14-3.21 (m, 4H), 3.74-3.82 (m, 4H), 4.33 (s, 2H), 7.36 (dd, J=8.2 Hz, 2.1 Hz, 1H), 7.53 (d, J=10.0 Hz, 1H), 7.62 (d, J=8.2 Hz, 1H), 7.67 (d, J=2.1 Hz, 1H), 7.74-7.86 (m, 1H), 7.96 (s, 1H), 8.01-8.06 (m, 1H), 11.18-11.28 (brs, 1H)

MS (ESI$^-$) m/z 487 (M−1)
HPLC$_{method\ 7}$ 97.1%/19.7 min

Example 43

Preparation of 2-[5-(4-Fluoro-benzyl)-thiazol-2-yl]-3-hydroxy-7-morpholin-4-ylmethyl-pyrido[1,2-a]pyrimidin-4-one

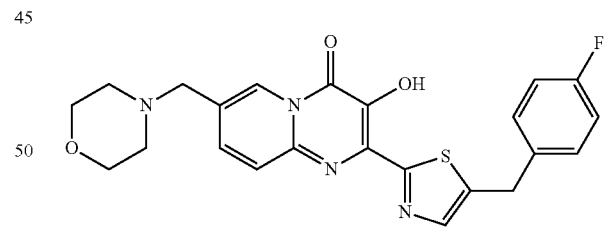

This example corresponds to Example 13.7 in International Patent Application No. PCT/AU2007/001980.
Step 1:

The product from Example 2.1 of International Patent Application No. PCT/AU2007/001980 (3.66 g, 15.6 mmol), t-butyldimethylsilyl chloride (3.52 g) and imidazole (2.66 g) were added to dichloromethane/DMF (30 mL/10 mL) and the mixture stirred at room temperature for 2 h. The mixture was diluted with dichloromethane (30 mL) and the organic phase washed with water, dried, filtered and concentrated in vacuo. The residue was subjected to column chromatography (hexane/ethyl acetate 4:1) to afford the desired compound (5.02 g, 92%).

$^1$H NMR (300 MHz, CDCl$_3$): δ 0.32 (s, 6H), 0.99 (s, 9H), 2.39 (s, 3H), 3.97 (s, 3H), 7.42 (dd, J=9.1, 1.8 Hz, 1H), 7.62 (d, J=9.2 Hz, 1H), 8.68 (bs, 1H).

Step 2:

To a stirred solution of the product from Step 1 (5 g, 14 mmol) in carbon tetrachloride (80 mL) was added N-bromosuccinimide (4.1 g) and t-butyl peroxide (0.348 g) under a nitrogen atmosphere. The reaction mixture was refluxed for 5 h and then cooled to room temperature. The solution was diluted with dichloromethane (200 mL), washed with water, dried, filtered and concentrated in vacuo. The residue was subjected to column chromatography (hexane/ethyl acetate 8:1) to afford the desired compound (3.0 g, 48%) as a yellow solid.

$^1$H NMR (300 MHz, DMSO-d$^6$): δ 0.26 (s, 6H), 0.94 (s, 9H), 3.86 (s, 3H), 4.88 (s, 2H), 7.66 (d, J=9.2 Hz, 1H), 7.79 (dd, J=9.3, 2.0 Hz, 1H), 9.03 (d, J=1.8 Hz, 1H)

Step 3:

The product from Step 2 (1.1 g, 2.6 mmol) and morpholine (672 mg, 7.73 mmol) were dissolved in a mixed solvent of dichloromethane/methanol (1:1, 20 mL). The solution was stirred at room temperature for 4 h then partially concentrated in vacuo and diluted with dichloromethane (40 mL) which was washed with brine, dried, filtered and evaporated under reduced pressure. Purification by silica gel column chromatography (hexane/ethyl acetate 1:1) afforded the desired product (1.03 g, 92%).

$^1$H NMR (300 MHz, DMSO-d$^6$): δ 0.26 (s, 6H), 0.93 (s, 9H), 2.43 (t, J=4.5 Hz, 4H), 3.53-3.62 (m, 6H), 3.86 (s, 3H), 7.64 (dd, J=9.1, 0.6 Hz, 1H), 7.76 (dd, J=9.2, 1.9 Hz, 1H), 8.74 (dd, J=1.8, 0.6 Hz, 1H)

Step 4:

The product from Step 4 (100 mg, 0.23 mmol) was added to a stirred mixed solvent of glacial acetic acid/water/tetrahydrofuran (1:1:3, 5 mL) and the mixture was stirred overnight at room temperature. Water (10 mL) was added and then solid sodium hydrogen carbonate was added to adjust the pH ~7. The mixture was extracted with twice with dichloromethane and the combined organic layers were washed, dried and concentrated in vacuo to give the desired compound (65 mg, 88%).

$^1$H NMR (300 MHz, DMSO-d$^6$): δ 2.42 (t, J=4.5 Hz, 4H), 3.53-3.63 (m, 6H), 3.88 (s, 3H), 7.58 (d, J=9.2 Hz, 1H), 7.64 (dd, J=9.4, 1.7 Hz, 1H), 8.62-8.67 (m, 1H), 10.24 (s, 1H)

Step 5-9:

The procedures described in Example 8.1 of International Patent Application No. PCT/AU2007/001980 (except the reaction was performed at 70° C. using DMF as the solvent), Example 8.2, Example 12.2, Example 13.1 and Example 12.4 of International Patent Application No. PCT/AU2007/001980 were adapted to provide of 2-[5-(4-fluoro-benzyl)-thiazol-2-yl]-3-hydroxy-7-morpholin-4-ylmethyl-pyrido[1,2-a]pyrimidin-4-one.

$^1$H NMR (300 MHz, DMSO-d$^6$) δ 2.40 (m, 4H, N—CH$_2$—CH$_2$—O), 3.53 (s, 2H, Ar—CH2-N), 3.57 (t, J=4.7 Hz, 4H, N—CH$_2$—CH$_2$—O), 4.30 (s, 2H, CH$_2$-thiazole), 7.17 (t, J=8.9 Hz, 2H, ArH), 7.39 (dd, J=8.9 Hz, 5.4 Hz, 2H, ArH), 7.52 (d, J=8.9 Hz, 1H, H9), 7.65 (dd, J=8.9, 2.4 Hz, 1H, H8), 7.95 (s, 1H, CH(thiazole)), 8.66 (m, 1H, H6), 11.33 (s, 1H, OH).

MS (ESI$^+$) m/z 453 (M+1)

Reaction Scheme for Examples 44 and 45

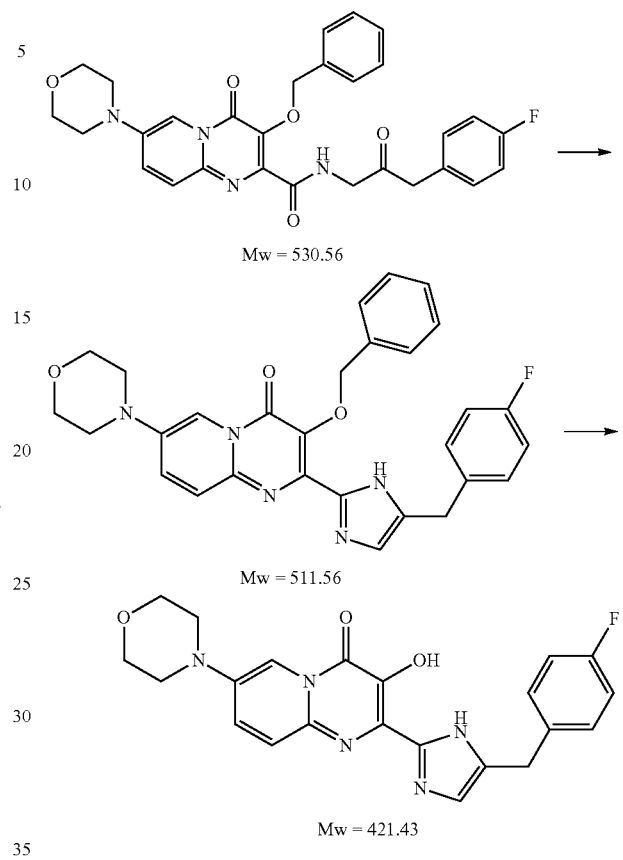

Example 44

Trifluoro-acetate2-(3-benzyloxy-7-morpholin-4-yl-4-oxo-4H-pyrido[1,2-a]pyrimidin-2-yl)-5-(4-fluoro-benzyl)-1H-imidazol-1-ium

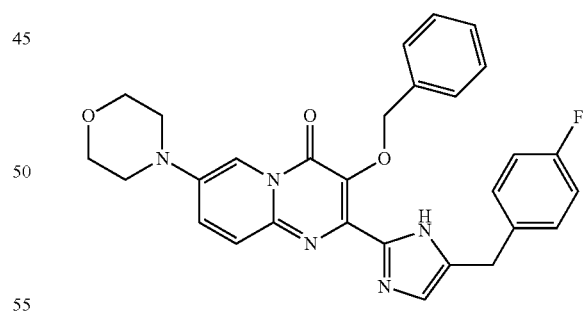

3-Benzyloxy-7-morpholin-4-yl-4-oxo-4H-pyrido[1,2-a]pyrimidine-2-carboxylic acid [3-(4-fluoro-phenyl)-2-oxo-propyl]-amide (Example 5) (225 mg) was dissolved in acetic acid (10 ml) and p-xylene (35 ml). Ammonium acetate (4 g) was added and the reaction mixture was stirred under reflux using Dear-Stark receiver to remove water. After 4 hours all solvents were removed under vacuum and the residue was purified on reverse phase preparative HPLC to afford a yellow solid. 103 mg (TFA salt), 38.8%.

MS: [M+H]$^+$512

LC: Rf: 1.89 min; 95.8% purity.

$^1$H NMR (300 MHz, CDCl$_3$): δ: 8.14 (1H, d), 7.63 (2H, m), 7.28 (2H, m), 7.24 (2H, m), 7.15 (2H, m), 7.0 (2H, m), 6.91 (1H, s), 6.50 (br), 5.52 (2H, s), 3.93 (6H, m); 3.26 (4H, m).

Example 45

5-(4-Fluoro-benzyl)-2-(3-hydroxy-7-morpholin-4-yl-4-oxo-4H-pyrido[1,2-a]pyrimidin-2-yl)-1H-imidazol-1-ium chloride

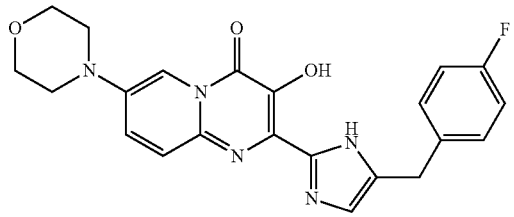

3-Benzyloxy-2-[5-(4-fluoro-benzyl)-1H-imidazol-2-yl]-7-morpholin-4-yl-pyrido[1,2-a]pyrimidin-4-one (91 mg, 0.145 mmol) was dissolved in acetonitrile (2 ml) and TMSBr (0.6 ml) was added. The reaction mixture was stirred overnight at room temperature. All the volatile solvents were removed, and the residue was evaporated from MeOH (10 ml). The residue was purified on reverse phase preparative HPLC. The obtained TFA salt was dissolved in acetonitrile (10 ml) and water (0.5 ml), and saturated ethereal solution of HCl (5 ml) was added. All solvents were removed under vacuum and the procedure repeated two more times. The residue was freeze-dried from acetonitrile water mixture to afford the title product as brownish solid.

51 mg, 76.5%

MS: [M+H]$^+$ 422

LC: Rf: 2.36 min; 96.19% purity.

$^1$H NMR (300 MHz, DMSO-d6): δ: 9.60 (1H, br), 8.05 (1H, s), 7.85 (1H, d, J=9.64 Hz), 7.58 (1H, d, J=9.59 Hz), 7.49 (1H, s), 7.39 (2H, dd; J=8.54, 5.86 Hz); 7.15 (2H, dd; J=9.09, 8.62 Hz); 4.13 (2H, br), 3.78 (4H, br), 3.20 (4H, br).

Reaction Scheme for Examples 46 and 47

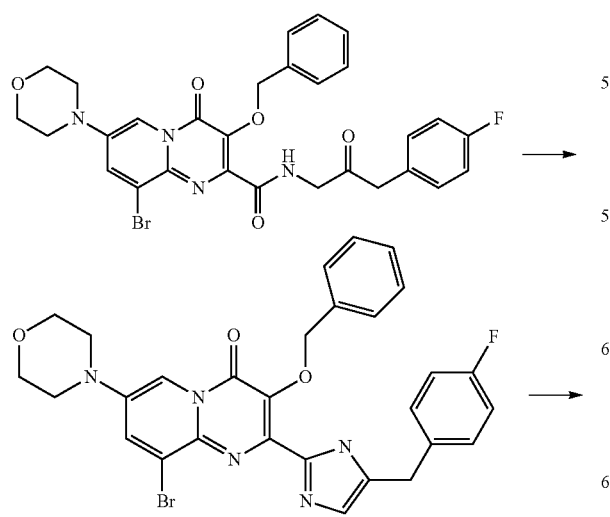

-continued

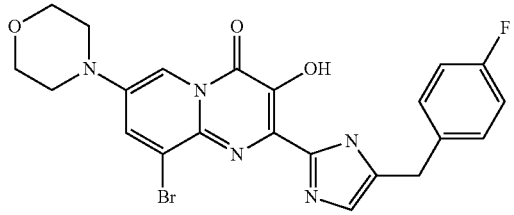

Example 46

Trifluoro-acetate2-(3-benzyloxy-9-bromo-7-morpholin-4-yl-4-oxo-4H-pyrido[1,2-a]pyrimidin-2-yl)-5-(4-fluoro-benzyl)-1H-imidazol-1-ium

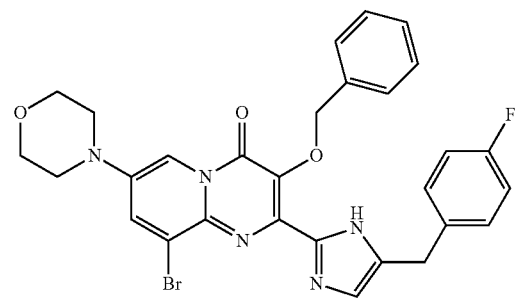

Starting from 235 mg of 3-benzyloxy-9-bromo-7-morpholin-4-yl-4-oxo-4H-pyrido[1,2-]pyrimidine-2-carboxylic acid [3-(4-fluoro-phenyl)-2-oxo-propyl]-amide (Example 2) using the procedure of Example 208 the title product was obtained in 16.6% yield (45.5 mg)

MS: [M+H]$^+$ 590/592

LC: Rf: 1.93 min; 95% purity.

Example 47

2-(9-Bromo-3-hydroxy-7-morpholin-4-yl-4-oxo-4H-pyrido[1,2-a]pyrimidin-2-yl)-5-(4-fluoro-benzyl)-1H-imidazol-1-ium chloride

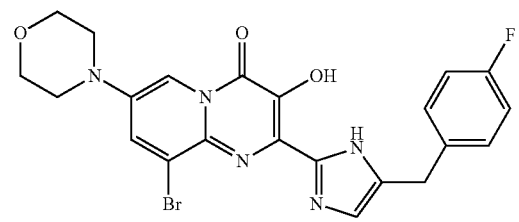

Starting from 45 mg of trifluoro-acetate2-(3-benzyloxy-9-bromo-7-morpholin-4-yl-4-oxo-4H-pyrido[1,2-a]pyrimidin-2-yl)-5-(4-fluoro-benzyl)-1H-imidazol-1-ium and using the procedure of example 209 the title product was obtained in 33.6% yield (14 mg)

MS: [M+H]$^+$500/502

LC: Rf: 2.76 min; 96.52% purity.

¹H NMR (300 MHz, DMSO-d6): δ: 8.38 (1H, br), 8.04 (1H, s), 7.38 (3H, m, br), 7.15 (2H, dd, J=8.59, 8.69 Hz), 4.12 (2H, s), 3.76 (4H, br), 3.20 (4H, br).

Example 48

3-Benzyl-9-(1-butoxy-vinyl)-7-morpholin-4-yl-4-oxo-4H-pyrido[1,2-a]pyrimidine-2-carboxylic acid methyl ester

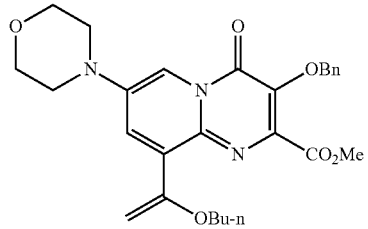

3-Benzyl-9-iodo-7-morpholin-4-yl-4-oxo-4H-pyrido[1,2-a]pyrimidine-2-carboxylic acid methyl ester (1 g, 1.92 mmol), n-Butyl vinyl ether (961 mg, 9.59 mmol), 1,3-Bis(diphenylphosphino)propane (DPPP) (24 mg, 0.058 mmol), Pd(OAc)₂ (11 mg, 0.048 mmol) were mixed in DMF (15 ml). The mixture was heated at 80° C. under the atmosphere of N₂ overnight, after which water was added and then extracted with dichloromethane. The extracts were combined, washed with brine, dried over sodium sulfate and evaporated under reduced pressure. The residue was purified by column chromatography to give the desired product (540 mg, yield 54%).

¹H NMR (300 MHz, DMSO-d⁶) δ 0.91 (t, J=7.5 Hz, 3H), 1.35-1.49 (m, 2H), 1.61-1.74 (m, 2H), 3.23 (t, J=4.6 Hz, 4H), 3.73-3.90 (m, 9H), 4.67 (d, J=2.0 Hz, 1H), 5.06 (d, J=2.1 Hz, 1H), 5.18 (s, 2H), 7.30-7.48 (m, 5H), 8.03 (d, J=2.7 Hz, 1H), 8.26 (d, J=2.7 Hz, 1H)

MS (ESI⁺) m/z 516 (M+23)

Example 49

9-Acetyl-3-benzyl-7-morpholin-4-yl-4-oxo-4H-pyrido[1,2-a]pyrimidine-2-carboxylic acid methyl ester

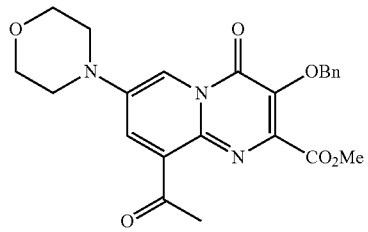

The mixture of the product of example 212 (100 mg, 0.20 mmol), dilute hydrochloric acid (2N, 1.6 ml) was stirred at room temperature for 5 h. The reaction mixture was extracted with dichloromethane. The combined organic layers were washed with water, dried and concentrated. The residue was purified by column chromatography to give the title compound (79 mg, 89% yield)

¹H NMR (300 MHz, CDCl₃) 2.90 (s, 3H), 3.26 (t, J=4.6 Hz, 4H), 3.84-3.96 (m, 7H), 5.33 (s, 2H), 7.30-7.43 (m, 3H), 7.46-7.57 (m, 2H), 7.97 (d, J=2.4 Hz, 1H), 8.44 (d, J=2.6 Hz, 1H)

MS (ESI⁺) m/z 460 (M+23)

Example 50

9-Acetyl-3-benzyloxy-7-morpholin-4-yl-4-oxo-4H-pyrido[1,2-a]pyrimidine-2-carboxylic acid

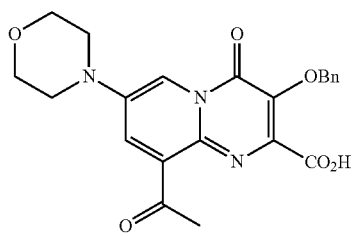

The title compound was prepared by adapting methods described in example 8.2 of International Patent Application No PCT/AU2007/001980 to Avexa using the product of example 49.

¹H NMR (300 MHz, DMSO-d⁶) 2.71 (s, 3H), 3.21-3.31 (m, 4H), 3.73-3.86 (m, 4H), 5.18 (s, 2H), 7.29-7.44 (m, 3H), 7.45-7.56 (m, 2H), 8.10 (d, J=2.6 Hz, 1H), 8.28 (d, 2.6 Hz, 1H)

MS (ESI⁺) m/z 446 (M+23)

Example 51

Preparation of 9-Acetyl-3-benzyloxy-7-morpholin-4-yl-4-oxo-4H-pyrido[1,2-a]pyrimidine-2-carbothioic acid S-[2-(4-fluoro-phenyl)-1-formyl-ethyl]ester

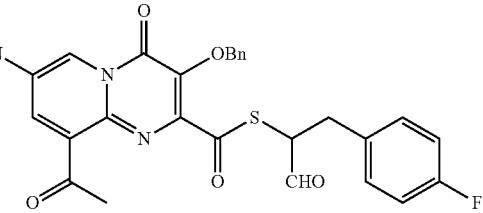

This compound was prepared by adapting examples 36 and 39 of co-pending International Patent Application filed 2 Jul. 2009 to Avexa Ltd entitled "Imidazopyrimidinones and uses thereof" using the product of example 50.

MS (ESI⁺) m/z 628 (M+39), 644 (M+55)

Example 52

Preparation of 9-Acetyl-3-benzyloxy-2-[5-(4-fluoro-benzyl)-thiazol-2-yl]-7-morpholin-4-yl-pyrido[1,2-a]pyrimidin-4-one

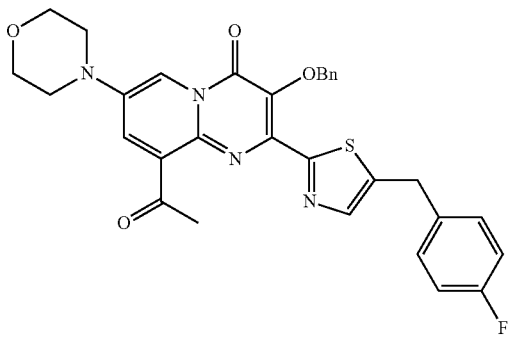

This compound was prepared by adapting examples 36 and 39 of co-pending International Patent Application filed 2 Jul. 2009 to Avexa Ltd entitled "Imidazopyrimidinones and uses thereof" using the product of example 51.

$^1$H NMR (300 MHz, DMSO-d$^6$) 2.81 (s, 3H), 3.20-3.27 (m, 4H), 3.74-3.84 (m, 4H), 4.28 (s, 2H), 5.24 (s, 2H), 7.17 (t, J=8.6 Hz, 2H), 7.28-7.42 (m, 5H), 7.51-7.60 (m, 2H), 7.92 (s, 1H), 8.07 (d, J=2.8 Hz, 1H), 8.24 (d, J=2.6 Hz, 1H).

MS (ESI$^+$) m/z 593 (M+23)

Example 53

Preparation of 9-Acetyl-2-[5-(4-fluoro-benzyl)-thiazol-2-yl]-3-hydroxy-7-morpholin-4-yl-pyrido[1,2-a]pyrimidin-4-one

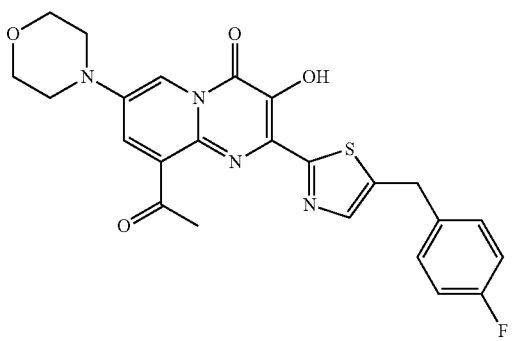

The product of example 52 was dissolved in anhydrous trifluoroactic acid and heated at 70° C. until consumption of all starting material. The volatiles were removed under vacuum and the residue was purified by preparative HPLC to afford the title product.

$^1$H NMR (300 MHz, DMSO-d$^6$) 2.77 (s, 3H), 3.12-3.24 (m, 4H), 3.70-3.84 (m, 4H), 4.32 (s, 2H), 7.17 (t, J=8.3 Hz, 2H), 7.32-7.46 (m, 2H), 7.88-8.03 (m, 2H), 8.13 (s, 1H), 11.29 (s, 1H).

MS (ESI$^+$) m/z 503 (M+23)

Example 54

3-Benzyloxy-9-bromo-2-[5-(4-fluoro-benzyl)-thiazol-2-yl]-7-morpholin-4-yl-pyrido[1,2-a]pyrimidin-4-one

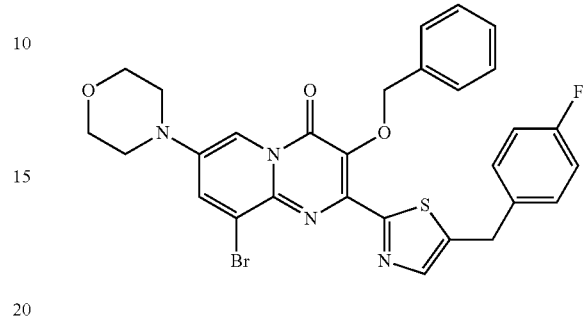

This compound was prepared by adapting examples 36, 39 and 40 of co-pending International Patent Application filed 2 Jul. 2009 to Avexa Ltd entitled "Imidazopyrimidinones and uses thereof" using the product of example 1.

$^1$H NMR (300 MHz, CDC$_3$) 3.207-3.24 (m, 4H), 3.89-3.92 (m, 4H), 4.20 (s, 2H), 5.44 (s, 2H), 7.05 (m, 2H), 7.19-7.31 (m, 5H), 7.52-54 (m, 2H), 7.88 (s, 1H), 7.94 (d, J=2.7 Hz, 1H), 8.29 (d, J=1.8 Hz, 1H).

MS (ESI$^+$) m/z 607/609 (M+1)

Example 55

Preparation of 3-Benzyloxy-2-[5-(4-fluoro-benzyl)-thiazol-2-yl]-9-(3-isopropyl-2-oxo-imidazolidin-1-yl)-7-morpholin-4-yl-pyrido[1,2-a]pyrimidin-4-one

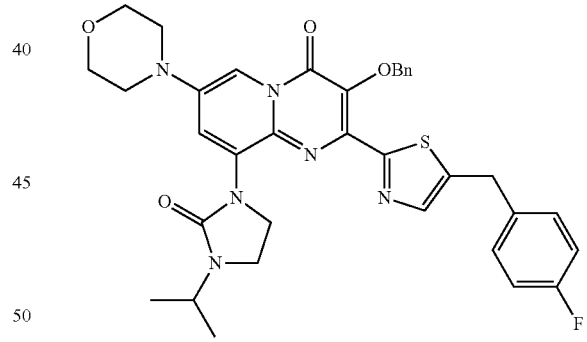

3-Benzyloxy-9-bromo-2-[5-(4-fluoro-benzyl)-thiazol-2-yl]-7-morpholin-4-yl-pyrido[1,2-a]pyrimidin-4-one (product of example 218, 110 mg, 0.18 mmol), 1-isopropyl-imidazolidin-2-one (30 mg, 0.22 mmol), Pd$_2$(dba)$_3$ (15 mg, 0.02 mmol), Xantphos (15 mg, 0.2 mmol), Cs$_2$CO$_3$ (58.5 mg, 0.18 mmol) were mixed in anhydrous dioxane (5 ml). The mixture was heated at 90° C. under the atmosphere of N$_2$ for 4 h, after which water was added and then extracted with ethyl acetate. The extracts were combined, washed with brine, dried over sodium sulfate and evaporated under reduced pressure. The residue was purified by column chromatography to give the desired product (95 mg, yield 81%).

$^1$H NMR (300 MHz, CDCl$_3$) δ 1.13 (d, J=6.7 Hz, 6H), 3.17-3.29 (m, 4H), 3.56 (t, J=7.6 Hz, 2H), 3.80-3.92 (m, 4H), 4.06-4.25 (m, 3H), 4.44 (t, J=7.9 Hz, 2H), 5.43 (s, 2H), 7.03

(t, J=8.4 Hz, 2H), 7.12-7.38 (m, 5H), 7.45-7.57 (m, 2H), 7.84 (s, 1H), 7.96 (s, 1H), 8.22 (s, 1H).
MS (ESI+) m/z 677 (M+23)

Example 56

Preparation of 2-[5-(4-Fluoro-benzyl)-thiazol-2-yl]-3-hydroxy-9-(3-isopropyl-2-oxo-imidazolidin-1-yl)-7-morpholin-4-yl-pyrido[1,2-a]pyrimidin-4-one

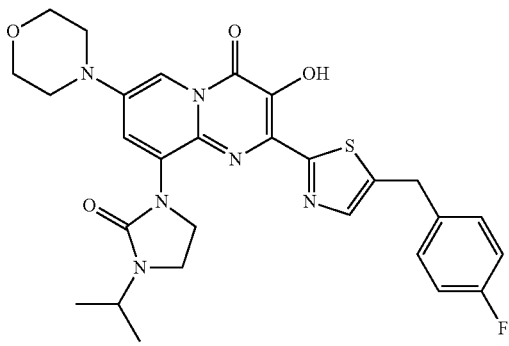

Adapted from example 53 using the product of example 55.
$^1$H NMR (300 MHz, DMSO-d$^6$) δ 1.12 (d, J=6.8 Hz, 6H), 3.08-3.21 (m, 4H), 3.47 (t, J=7.7 Hz, 2H), 3.68-3.82 (m, 4H), 3.94-4.08 (m, 3H), 4.31 (s, 2H), 7.17 (t, J=9.0 Hz, 2H), 7.36 (dd, J=5.8, 8.8 Hz, 2H), 7.84 (d, J=2.3 Hz, 1H), 7.95 (s, 1H), 7.98 (d, J=2.4 Hz, 1H), 11.17 (s, 1H).
MS (ESI⁻) m/z 563 (M−1)

Example 57

Preparation of 3-Benzyloxy-9-(3-methyl-2-oxo-imidazolidin-1-yl)-7-morpholin-4-yl-4-oxo-4H-pyrido[1,2-a]pyrimidine-2-carboxylic acid methyl ester

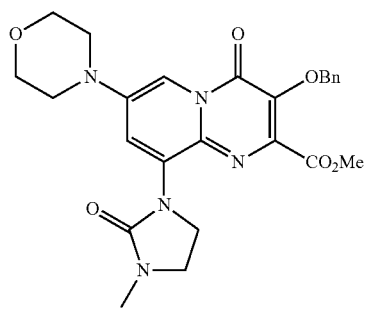

3-Benzyloxy-9-bromo-7-morpholin-4-yl-4-oxo-4H-pyrido[1,2-a]pyrimidine-2-carboxylic acid methyl ester (1 g, 2.1 mmol) 1-methylimidazolidin-2-one (300 mg, 3 mmol), Pd$_2$(dba)$_3$ (100 mg, 0.11 mmol), Xantphos (100 mg, 0.17 mmol), Cs$_2$CO$_3$ (800 mg, 2.46 mmol) were mixed in anhydrous dioxane (25 ml). The mixture was heated at 100° C. under the atmosphere of N$_2$ for 4 h, after which water was added and then extracted with ethyl acetate. The extracts were combined, washed with brine, dried over sodium sulfate and evaporated under reduced pressure. The residue was purified by column chromatography to give the desired product (0.7 g, 67% yield).

$^1$H NMR (300 MHz, CDCl$_3$) δ 2.93 (s, 3H), 3.25 (m, 4H), 3.54 (t, 7.8 Hz, 2H), 3.82-3.92 (m, 7H), 4.08 (t, J=7.8 Hz, 2H), 5.31 (s, 2H), 7.29-7.56 (m, 5H), 7.96 (d, 2.1 Hz, 1H), 8.25 (d, 2.1 Hz, 1H)

Example 58

Preparation of 3-Benzyloxy-9-(3-methyl-2-oxo-imidazolidin-1-yl)-7-morpholin-4-yl-4-oxo-4H-pyrido[1,2-a]pyrimidine-2-carboxylic acid [3-(3-chloro-4-fluoro-phenyl)-2-oxo-propyl]-amide

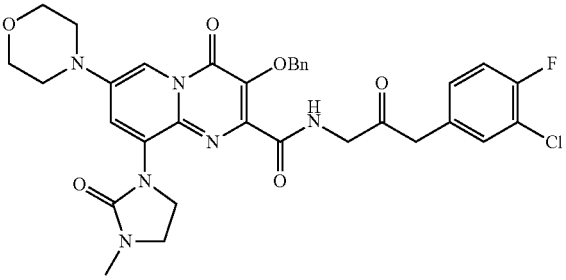

Adapted from examples 1 and 2 using the product of example 221.

H NMR (300 MHz, DMSO-d$^6$) δ 2.78 (s, 3H), 3.15-3.26 (br, 4H), 3.41-3.52 (t, J=8.1 Hz, 2H), 3.72-3.83 (m, 4H), 3.91 (s, 2H), 4.05-4.14 (t, J=7.5 Hz, 2H), 4.22-4.30 (d, J=5.1 Hz, 2H), 5.15 (s, 2H), 7.16-7.60 (m, 8H), 7.69-7.76 (m, 1H), 7.94-8.02 (d, J=2.4 Hz, 1H), 8.11-8.17 (d, J=2.4 Hz, 1H), 8.64-8.73 (m, 1H)

Example 59

Preparation of 3-Benzyloxy-2-[5-(3-chloro-4-fluoro-benzyl)-thiazol-2-yl]-9-(3-methyl-2-oxo-imidazolidin-1-yl)-7-morpholin-4-yl-pyrido[1,2-a]pyrimidin-4-one

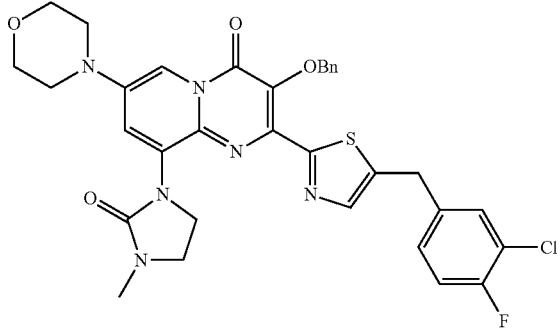

Adapted from example 9 using the product of example 58.
$^1$H NMR (300 MHz, CDCl$_3$) δ 2.93 (s, 3H), 3.18-3.29 (br, 4H), 3.55-3.67 (t, J=8.1 Hz, 2H), 3.80-3.93 (br, 4H), 4.16 (s, 2H), 4.37-4.49 (t, J=7.8 Hz, 2H), 5.44 (s, 2H), 7.04-7.16 (m, 2H), 7.23-7.36 (m, 4H), 7.48-7.56 (m, 2H), 7.81-7.86 (d, J=2.4 Hz, 1H), 7.92 (s, 1H), 8.22 (s, 1H)
MS (ESI⁻) m/z 659 (M−1)

Example 60

Preparation of 2-[5-(3-Chloro-4-fluoro-benzyl)-thiazol-2-yl]-3-hydroxy-9-(3-methyl-2-oxo-imidazolidin-1-yl)-7-morpholin-4-yl-pyrido[1,2-a]pyrimidin-4-one

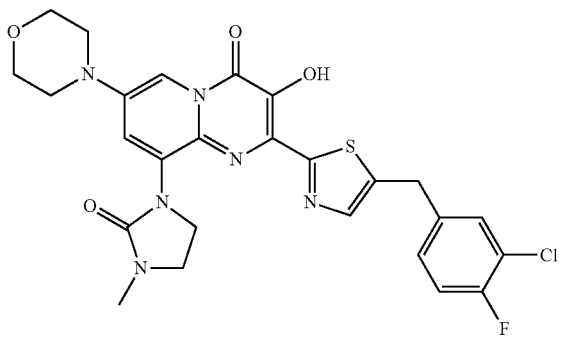

A solution of 3-Benzyloxy-2-[5-(3-chloro-4-fluoro-benzyl)-thiazol-2-yl]-9-(3-methyl-2-oxo-imidazolidin-1-yl)-7-morpholin-4-yl-pyrido[1,2-a]pyrimidin-4-one (50 mg, 0.076 mmol) in trifluoroacetic acid (1 ml) was refluxed for 3 h. Then trifluoroacetic acid was removed under reduced pressure and MeOH (3 ml) was added. The resulting precipitate was collected by filtration and washed with MeOH to give title compound (40 mg, 93%).

$^1$H NMR (300 MHz, DMSO-d$^6$) δ 2.80 (s, 3H), 3.08-3.22 (br, 4H), 3.45-3.60 (t, J=8.1 Hz, 2H), 3.68-3.85 (br, 4H), 3.98-4.13 (t, J=8.1 Hz, 2H), 4.33 (s, 2H), 7.30-7.43 (m, 2H), 7.56-7.66 (d, J=6.3 Hz, 1H), 7.80 (s, 1H), 7.96 (s, 1H), 7.98 (s, 1H)

MS (ESI$^+$) m/z 571 (M+1)

Example 61

Preparation of 3-Iodo-5-nitro-pyridin-2-ylamine

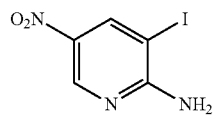

5-nitropyridin-2-amine (14 g, 10 mmol), KI (16.6 g, 10 mmol), KIO$_3$ (10.7 g, 5 mmol) were mixed in dilute sulfuric acid (2N, 200 ml). The mixture was stirred at 80° C. overnight, after which NaOH solution (5N, 80 ml) was added to adjust the pH to about 10. The resulting solids were collected by filtration, washed with water and ethanol successively, and then dried in vacuo to give the titled compound (25 g, 94% yield).

$^1$H NMR (300 MHz, DMSO-d$^6$) δ 6.80-8.40 (brs, 2H), 8.57 (d, J=2.4 Hz, 1H), 8.84 (d, J=2.4 Hz, 1H).

MS (ESI$^-$) m/z 264 (M−1)

Example 62

Preparation of 3-Iodo-pyridine-2,5-diamine

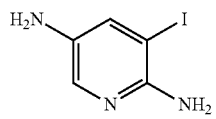

The product of Example 225 (5.3 g, 20 mmol), SnCl$_2$.2H$_2$O (22.6 g, 100 mmol) was mixed in EtOH (100 ml). The mixture was refluxed for 10 h, after which the mixture was poured into water (200 ml) and extracted with ethyl acetate for three times. The extracts were combined, dried over sodium sulfate. The product was purified by column chromatography to give the desired product (2.5 g, 50% yield).

$^1$H NMR (300 MHz, DMSO-d$^6$) δ 4.54 (s, 2H), 5.06 (s, 2H), 7.32 (d, J=2.4 Hz, 1H), 7.45 (d, J=2.6 Hz, 1H).

MS (ESI$^+$) m/z 236 (M+1)

Example 63

Preparation of Preparation of 3-iodo-N$^5$,N$^5$-dimethylpyridine-2,5-diamine

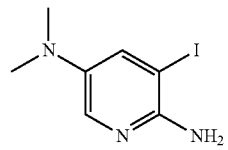

Paraformaldehyde (1 g, 33.3 mmol) was suspended in MeOH (30 ml) and refluxed for 2 h, then cooled to room temperature. Then 3-iodopyridine-2,5-diamine (2 g, 8.5 mmol) was added to the above mixture, followed by NaCNBH$_3$ (4.7 g, 76 mmol) in small portions. After TLC plate indicated that the reaction was over, most of the solvent was removed under reduced pressure. Water was added and the mixture was extracted with ethyl acetate. The combined organic layers were washed with water, dried and concentrated in vacuo. The residue was purified by column chromatography to give the desired product (0.8 g, 35% yield).

$^1$H NMR (300 MHz, DMSO-d$^6$) δ 2.72 (s, 6H), 5.32 (s, 2H), 7.48 (d, J=2.6 Hz, 1H), 7.62 (d, J=2.6 Hz, 1H)

MS (ESI$^+$) m/z 264 (M+1)

Example 64

Preparation of 3-Acetoxy-7-dimethylamino-9-iodo-4-oxo-4H-pyrido[1,2-a]pyrimidine-2-carboxylic acid methyl ester

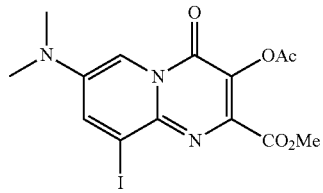

The product of example 227 (100 mg, 0.38 mmol), p-toluenesulfonic acid (10 mg, 0.52 mmol), DAF (400 mg, 1.53 mmol) were mixed in MeOH (0.5 ml). The mixture was stirred at 80° C. for 8 h, after which the solvent was evaporated and acetic anhydride (400 mg, 4 mmol) in pyridine (5 ml) was added. The mixture was refluxed for 1 h. After cooling to the room temperature, the mixture was concentrated under reduced pressure. The resulting residue was purified by column chromatography to give the desired product (20 mg, 12% yield).

¹H NMR (300 MHz, DMSO-d⁶) δ 2.31 (s, 3H), 3.03 (s, 6H), 3.90 (s, 3H), 8.00 (d, J″ 2.4 Hz, 1H), 8.56 (d, J=2.7 Hz, 1H)

MS (ESI⁺) m/z 454 (M+23)

Example 65

Preparation of methyl 7-(dimethylamino)-3-hydroxy-9-iodo-4-oxo-4H-pyrido[1,2-a]pyrimidine-2-carboxylate

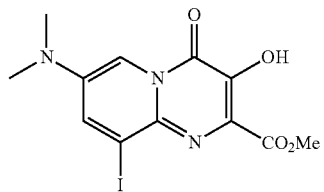

To a solution of the product of example 228 (15 mg, 0.035 mmol) in MeOH (5 ml) was added K₂CO₃ (30 mg, 0.217 mmol). The mixture was refluxed for 5 h and then extracted with dichloromethane and water. Organic layer was concentrated into dryness to give the titled product (12 mg, yield 80%).

¹H NMR (300 MHz, DMSO-d⁶) δ 2.97 (s, 6H), 3.89 (s, 3H), 7.84 (d, 2.3 Hz, 1H), 8.35 (d, J=2.5 Hz, 1H), 10.18 (s, 1H)

Example 66

Preparation of 3-Benzyloxy-7-dimethylamino-9-iodo-4-oxo-4H-pyrido[1,2-a]pyrimidine-2-carboxylic acid methyl ester

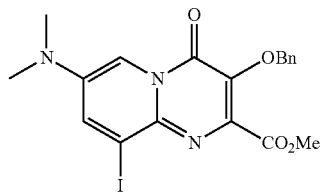

The title compound was prepared by adapting methods described in example 8.1-8.2 of International Patent Application No. PCT/AU2007/001980 to Avexa Limited using the product of example 65.

¹H NMR (300 MHz, DMSO-d⁶) δ 3.02 (s, 6H), 3.84 (s, 3H), 5.17 (s, 2H), 7.28-7.48 (m, 5H), 8.05 (d, J=2.7 Hz, 1H), 8.49 (d, J=2.7 Hz, 1H)

Example 67

Preparation of 3-Benzyloxy-7-dimethylamino-9-(3-methyl-2-oxo-imidazolidin-1-yl)-4-oxo-4H-pyrido[1,2-a]pyrimidine-2-carboxylic acid methyl ester

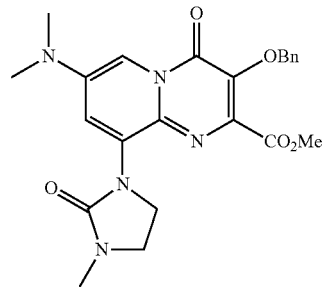

Adapted from example 57 using the product of example 66.

¹H NMR (300 MHz, DMSO-d⁶) δ 2.50 (s, 3H? overlapped with DMSO?) 3.04 (s, 6H), 3.54 (t, J=7.3 Hz, 2H), 3.84 (s, 3H), 3.94 (t, J=7.1 Hz, 2H), 5.17 (s, 2H), 7.32-7.50 (m, 5H), 7.89 (d, J=2.7 Hz, 1H), 7.99 (d, J=2.9 Hz, 1H)

MS (ESI⁺) m/z 474 (M+23)

Example 68

Preparation of 3-Benzyloxy-7-dimethylamino-9-(3-methyl-2-oxo-imidazolidin-1-yl)-4-oxo-4H-pyrido[1,2-a]pyrimidine-2-carboxylic acid [3-(4-fluoro-phenyl)-2-oxo-propyl]-amide

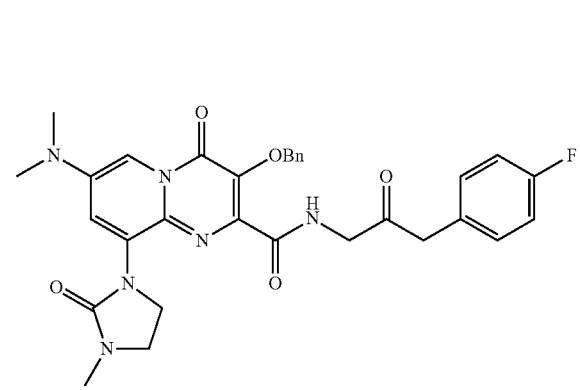

Adapted from example 1 and 2 using the product of example 67.

¹H NMR (300 MHz, DMSO-d⁶) δ 2.77 (s, 3H), 3.01 (s, 6H), 3.47 (t, J=7.9 Hz, 2H), 3.88 (s, 2H), 4.10 (t, J=7.8 Hz, 2H), 4.24 (d, J=5.5 Hz, 2H), 5.14 (s, 2H), 7.14 (t, J=9.0 Hz, 2H), 7.24 (dd, J=5.8, 9.1 Hz, 2H), 7.28-7.40 (m, 3H), 7.48-7.56 (m, 2H), 7.88 (d, J=2.9 Hz, 1H), 7.97 (d, J=2.7 Hz, 1H), 8.66 (t, J=5.5 Hz, 1H)

MS (ESI⁺) m/z 609 (M+23)

Example 69

Preparation of 3-Benzyloxy-7-dimethylamino-2-[5-(4-fluoro-benzyl)-thiazol-2-yl]-9-(3-methyl-2-oxo-imidazolidin-1-yl)-pyrido[1,2-a]pyrimidin-4-one

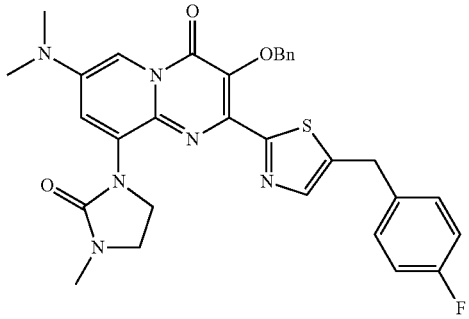

Adapted from example 9 using the product of example 68.

$^1$H NMR (300 MHz, DMSO-d$^6$) δ 2.78 (s, 3H), 3.00 (s, 6H), 3.51 (t, J=7.8 Hz, 2H), 4.12 (t, J=8.1 Hz, 2H), 4.27 (s, 2H), 5.20 (s, 2H) ☐7.18 (t, J=8.6 Hz, 2H), 7.27-7.43 (m, 5H), 7.53-7.60 (m, 2H), 7.84-7.96 (m, 3H)

MS (ESI$^+$) m/z 607 (M+23)

Example 70

Preparation of 7-Dimethylamino-2-[5-(4-fluoro-benzyl)-thiazol-2-yl]-3-hydroxy-9-(3-methyl-2-oxo-imidazolidin-1-yl)-pyrido[1,2-a]pyrimidin-4-one

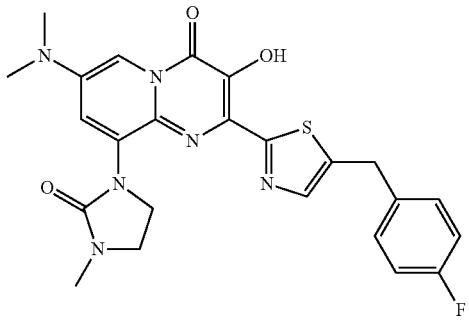

Adapted from example 53 using the product of example 69.

$^1$H NMR (300 MHz, DMSO-d$^6$) δ 2.80 (s, 3H), 2.96 (s, 6H), 3.52 (t, J=7.8 Hz, 2H), 4.06 (t, J=7.8 Hz, 2H), 4.30 (s, 2H), 7.17 (t, J=8.7 Hz, 2H), 7.38 (dd, J=6.1, 8.5 Hz, 2H), 7.74 (d, J=2.2 Hz, 1H), 7.81 (d, J=2.2 Hz, 1H), 7.92 (s, 1H), 11.05 (s, 1H).

MS (ESI$^-$) m/z 493 (M−1)

Example 71

Preparation of 3-Benzyloxy-7-dimethylamino-2-[5-(4-fluoro-benzyl)-1H-imidazol-2-yl]-9-(3-methyl-2-oxo-imidazolidin-1-yl)-pyrido[1,2-a]pyrimidin-4-one

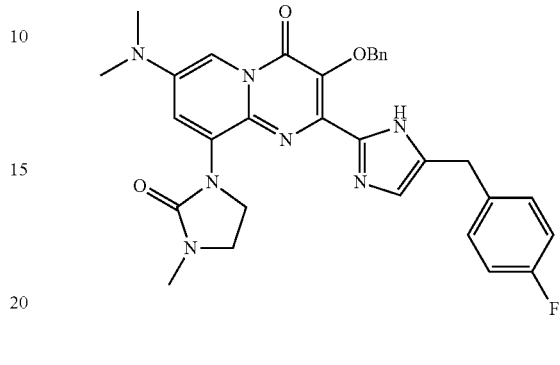

Adapted from example 44 using the product of example 68.

$^1$H NMR (300 MHz, CDCl$_3$) δ 2.93 (s, 3H), 3.05 (s, 6H), 3.64 (t, J=8.1 Hz, 2H), 3.92 (s, 2H), 4.48 (t, J=8.0 Hz, 2H), 5.37 (s, 2H), 6.86 (s, 1H), 6.97 (t, J=8.9 Hz, 2H), 7.10-7.21 (m, 2H), 7.28-7.34 (m, 3H), 7.35-7.43 (m, 2H), 7.86 (d, J=2.6 Hz, 1H), 8.05 (d, J=2.6 Hz, 1H)

MS (ESI$^+$) m/z 568 (M+1)

Example 72

Preparation of 2-(7-(dimethylamino)-3-hydroxy-9-(3-methyl-2-oxoimidazolidin-1-yl)-4-oxo-4H-pyrido[1,2-a]pyrimidin-2-yl)-5-(4-fluorobenzyl)-1H-imidazol-3-ium chloride

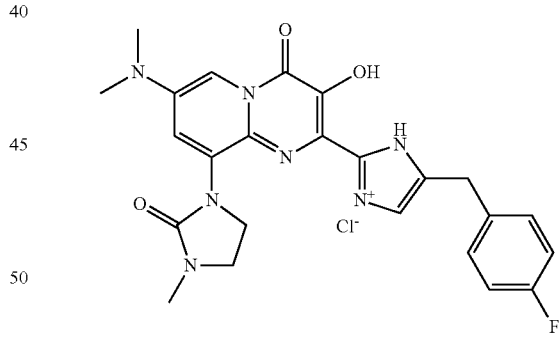

2-(5-(4-fluorobenzyl)-1H-imidazol-2-yl)-3-(benzyloxy)-7-(dimethylamino)-9-iodo-4H-pyrido[1,2-a]pyrimidin-4-one (50 mg, 0.88 mmol) in trifluoroacetic acid (2 ml) was refluxed for 3 h, after which ethyl acetate (20 ml) was added. To the above solution was added a drop of HCl solution (37%). The resulting solids were collected by filtration and washed with ethyl acetate to give the title compound (30 mg, 60%).

$^1$H NMR (300 MHz, DMSO-d$^6$) δ 2.85 (s, 3H), 2.99 (s, 6H), 3.55 (t, J=7.7 Hz, 2H), 4.06-4.19 (m, 4H), 7.18 (t, J=8.9 Hz, 2H), 7.40 (dd, J=5.9, 8.4 Hz, 2H), 7.49 (s, 1H), 7.76 (d, J=2.6 Hz, 1H), 7.81 (d, J=2.6 Hz, 1H)

MS (ESI$^+$) m/z 478 (M−Cl$^-$)

Example 73

Preparation of 3-Benzyloxy-9-(3-methyl-2-oxo-imidazolidin-1-yl)-7-morpholin-4-yl-4-oxo-4H-pyrido[1,2-a]pyrimidine-2-carboxylic acid amide

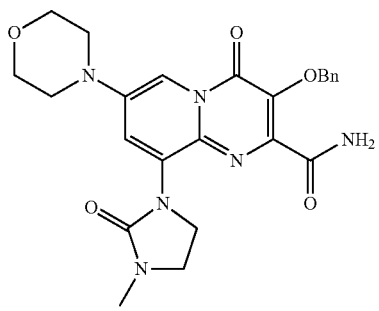

3-Benzyloxy-9-(3-methyl-2-oxo-imidazolidin-1-yl)-7-morpholin-4-yl-4-oxo-4H-pyrido[1,2-a]pyrimidine-2-carboxylic acid methyl ester (example 221, 1 g, 2.03 mmol) was mixed with ammonia water (28%, 50 ml) and the mixture was heated at 40° C. overnight. The precipitates were collected by filtration and dried in vacuo to give the titled compound (600 mg, 62%).

$^1$H NMR (300 MHz, DMSO-d$^6$) δ 2.78 (s, 3H), 3.16-3.25 (m, 4H) ☐3.50 (t, J=7.5 Hz, 2H), 3.72-3.81 (m, 4H), 4.08 (t, J=7.5 Hz, 2H), 5.13 (s, 2H), 7.30-7.43 (m, 3H), 7.50-7.57 (m, 2H), 7.69 (s, 1H), 7.81 (s, 1H), 7.96 (d, J=2.4 Hz, 1H), 8.16 (d, J=2.2 Hz; 1H)

Example 74

Preparation of 3-Benzyloxy-9-(3-methyl-2-oxo-imidazolidin-1-yl)-7-morpholin-4-yl-4-oxo-4H-pyrido[1,2-a]pyrimidine-2-carbothioic acid amide

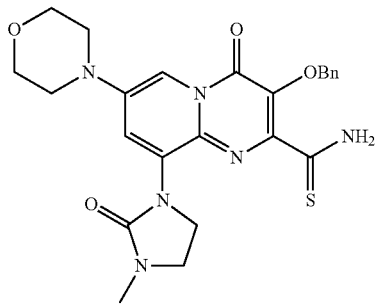

The product of Example 73 (239 mg, 0.5 mmol) in anhydrous tetrahydrofuran (THF, 15 ml) was added Lawesson reagent (240 mg, 0.6 mmol) and the mixture was refluxed for 1 h. The solvent was removed under reduced pressure. The resulting solids were washed with ethyl acetate and dried in vacuo to give the title compound (150 mg, 60%), which was used directly in next step.

Example 75

Preparation of 3-Benzyloxy-9-(3-methyl-2-oxo-imidazolidin-1-yl)-7-morpholin-4-yl-4-oxo-4H-pyrido[1,2-a]pyrimidine-2-carboximidothioic acid methyl ester

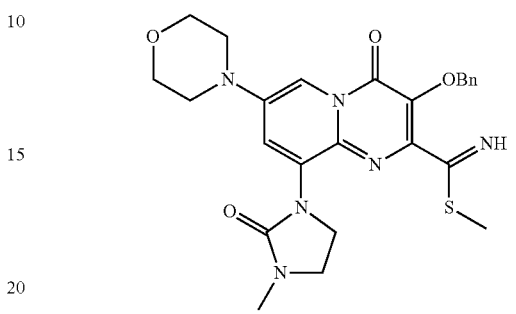

To a solution of the product of example 74 (250 mg, 0.5 mmol) in THF (20 ml) was added diisopropyl ethylamine (65 mg, 0.5 mmol) and methyl iodide (140 mg, 1 mmol), and the mixture was stirred at 60° C. for 1.5 h. The reaction mixture was added ice water, and extracted with ethyl acetate. The organic layer was washed with saturated sodium hydrogen carbonate solution and dried over magnesium sulfate. The solvent was evaporated under reduced pressure to give title product (190 mg, 74%).

$^1$H NMR (300 MHz, CDCl$_3$) δ 2.48 (s, 3H), 2.97 (s, 3H) ☐3.20-3.30 (m, 4H), 3.60 (t 7.8 Hz, 2H), 3.82-3.91 (m, 4H), 4.37 (t, J=7.8 Hz, 2H), 5.42 (s, 2H), 7.28-7.42 (m, 3H), 7.43-7.57 (m, 2H), 7.95 (d, J=2.4 Hz, 1H), 8.20 (d, J=2.4 Hz, 1H).

MS (ESI$^+$) m/z 509 (M+1), 531 (M+23)

Example 76

Preparation of 3-Benzyloxy-2-[5-(3-chloro-4-fluorobenzyl)-1H-imidazol-2-yl]-9-(3-methyl-2-oxo-imidazolidin-1-yl)-7-morpholin-4-yl-pyrido[1,2-a]pyrimidin-4-one

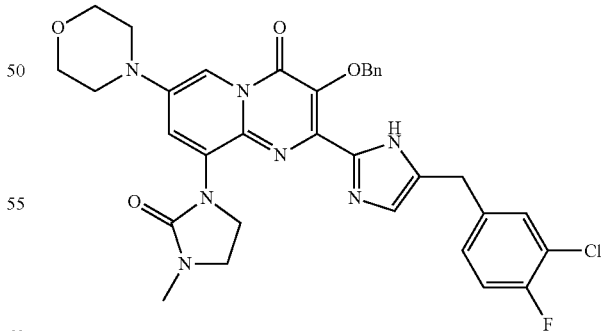

To a solution of the product of Example 75 (120 mg, 0.23 mmol) in acetic acid (4 ml) was added 1-amino-3-(3-chloro-4-fluorophenyl)propan-2-one hydrochloride (71 mg, 0.3 mmol). The mixture was heated at 70° C. for 1.5 h. After cooling to the room temperature, the mixture was concentrated under reduced pressure, poured into ice-water and extracted with ethyl acetate. The combined organic layers were dried and concentrated in vacuo to give the titled compound (100 mg, 65%), which was used directly in next step.

Example 77

Preparation of 5-(3-chloro-4-fluorobenzyl)-2-(3-hydroxy-9-(3-methyl-2-oxoimidazolidin-1-yl)-7-morpholino-4-oxo-4H-pyrido[1,2-a]pyrimidin-2-yl)-1H-imidazol-3-ium chloride

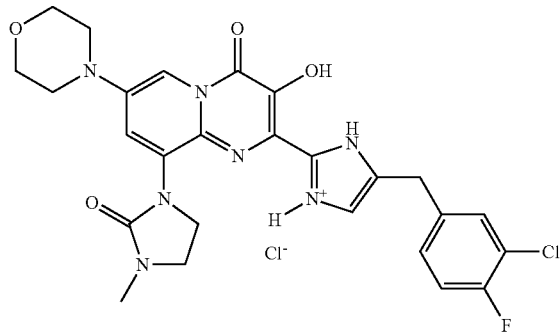

The solution of the product of Example 76 (80 mg, 0.12 mmol) in trifluoroacetic acid (2 ml) was refluxed for 3 h and then concentrated under reduced pressure. The residue was dissolved in ethyl acetate (20 ml) and then a drop of HCl solution (37%) was added. The precipitates were collected by filtration and washed with ethyl acetate to give the title compound (40 mg, 56%).

$^1$H NMR (300 MHz, DMSO-d$^6$) δ 2.85 (s, 3H), 3.10-3.19 (m, 4H), 3.54 (t, J=7.5 Hz, 2H), 3.70-3.78 (m, 4H), 4.10 (t, J=7.5 Hz, 2H), 4.17 (s, 2H), 7.32-7.41 (m, 2H), 7.56 (s, 1H), 7.66 (d, J=6.6 Hz, 1H), 7.79 (d, J=2.7 Hz, 1H), 7.95 (d, J=2.4 Hz, 1H).

MS (ESI$^-$) m/z 588 (M−1)

Example 78

Preparation of 3-Benzyloxy-2-[5-(3,4-difluoro-benzyl)-1H-imidazol-2-yl]-9-(3-methyl-2-oxo-imidazolidin-1-yl)-7-morpholin-4-yl-pyrido[1,2-a]pyrimidin-4-one

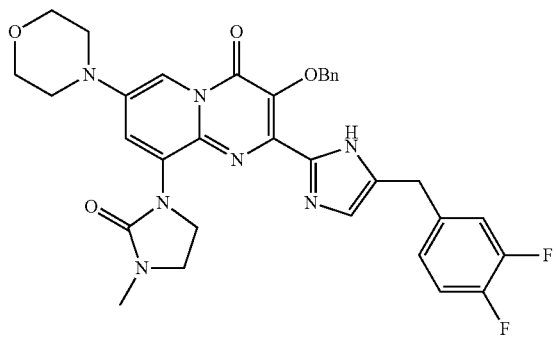

Adapted from the procedure of example 76 using the product of example 75 and 1-amino-3-(3,4-difluorophenyl)propan-2-one hydrochloride. The title product was used directly in next step.

Example 79

5-(3,4-difluorobenzyl)-2-(3-hydroxy-9-(3-methyl-2-oxoimidazolidin-1-yl)-7-morpholino-4-oxo-4H-pyrido[1,2-a]pyrimidin-2-yl)-1H-imidazol-3-ium chloride

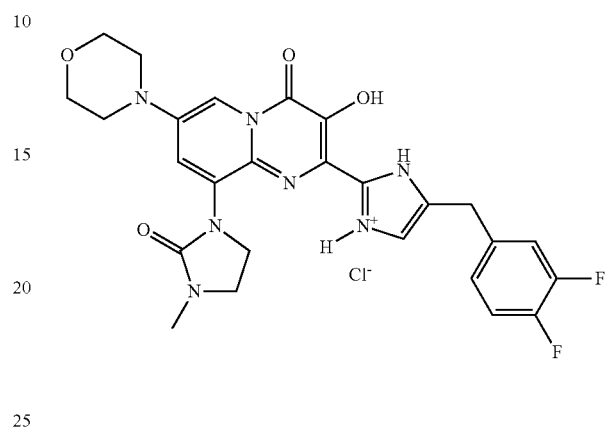

Adapted from the procedure of example 77 using the product of example 78.

$^1$H NMR (300 MHz, DMSO-d$^6$) δ 2.83 (s, 3H), 3.10-3.22 (m, 4H), 3.57 (t, J=7.2 Hz, 2H), 3.71-3.82 (m, 4H), 4.15 (t, J=6.8 Hz, 2H), 4.18 (s, 2H), 7.33-7.44 (m, 2H), 7.49 (s, 1H), 7.47-7.55 (m, 1H), 7.80 (d, J=2.7 Hz, 1H), 7.97 (d, J=2.1 Hz, 1H).

MS (ESI$^-$) m/z 572 (M−1)

Example 80

Preparation of 3-Benzyloxy-7-morpholin-4-yl-4-oxo-9-(2-oxopyrrolidin-1-yl)-4H-pyrido[1,2-a]pyrimidine-2-carboxylic acid methyl ester

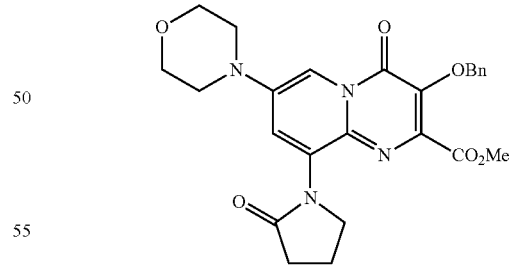

Adapted from example 57 using pyrrolidine-2-one.

$^1$H NMR (300 MHz, CDCl$_3$) δ 2.16-2.30 (m, 2H), 2.60 (t, J=7.8 Hz, 2H), 3.25 (t, 5.1 Hz, 4H), 3.90 (s, 7H), 4.18 (t, J=7.5 Hz, 2H), 5.31 (s, 2H), 7.29-7.42 (m, 3H), 7.47-7.55 (m, 2H), 7.78 (s, 1H), 8.30 (s, 1H)

MS (ESI$^+$) m/z 501 (M+23)

Example 81

Preparation of 3-Benzyloxy-7-morpholin-4-yl-4-oxo-9-(2-oxo-pyrrolidin-1-yl)-4H-pyrido[1,2-a]pyrimidine-2-carboxylic acid [3-(4-fluoro-phenyl)-2-oxo-propyl]-amide

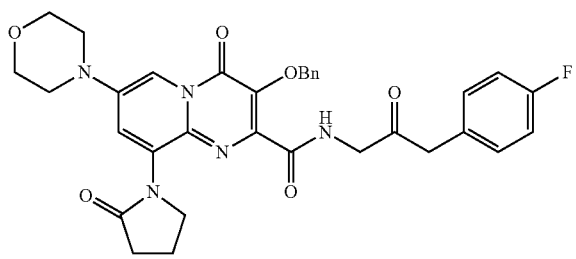

Adapted from example 1 and 2 using the product of example 70.

$^1$H NMR (300 MHz, CDCl$_3$) δ 2.27-2.41 (m, 2H), 2.69 (t, J=8.1 Hz, 2H), 3.18-3.31 (m, 4H), 3.77 (s, 2H) 3.91 (m, 4H), 4.10-4.21 (t, J=6.6 Hz, 2H), 4.34 (d, J=4.5 Hz, 2H), 5.34 (s, 2H), 7.05 (t, J=8.1 Hz, 2H), 7.15-7.39 (m, 5H), 7.53-7.64 (m, 2H), 7.69-7.76 (d, J=2.7 Hz, 1H), 8.22-8.35 (m, 2H)

MS (ESI$^-$) m/z 612 (M−1)

Example 82

Preparation of 3-Benzyloxy-2-[5-(4-fluoro-benzyl)-1H-imidazol-2-yl]-7-morpholin-4-yl-9-(2-oxo-pyrrolidin-1-yl)-pyrido[1,2-a]pyrimidin-4-one

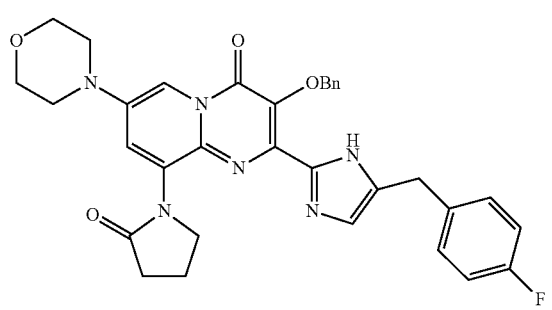

Adapted from example 76 using the product of example 81.

$^1$H NMR (300 MHz, CDCl$_3$) δ 2.20-2.37 (m, 2H), 2.67 (t, J=7.8 Hz, 2H), 3.24 (t, 4.5 Hz, 4H), 3.80-4.02 (m, 6H), 4.38 (t, J=6.9 Hz, 2H), 5.38 (s, 2H), 6.97 (t, J=9 Hz, 2H), 7.41-7.49 (m, 8H), 7.80 (d, J=2.7 Hz, 1H), 8.26 (d, J=2.7 Hz, 1H)

MS (ESI$^+$) m/z 595 (M+1), 617 (M+23)

Example 83

Preparation of 5-(4-fluorobenzyl)-2-(3-hydroxy-7-morpholino-4-oxo-9-(2-oxopyrrolidin-1-yl)-4H-pyrido[1,2-a]pyrimidin-2-yl)-1H-imidazol-3-ium chloride

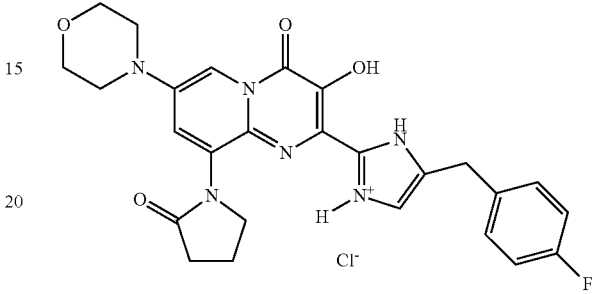

Adapted from example 77 using the product of example 82.

$^1$H NMR (300 MHz, DMSO-d$^6$) δ 2.10-2.25 (m, 2H), 2.50 (t, J=7.8 Hz, 2H), 3.12-3.24 (m, 4H), 3.70-3.83 (m, 4H), 3.94 (t, J=6 Hz, 2H), 4.12 (s, 2H), 7.15 (t, J=8.1 Hz, 2H), 7.38 (t, J=7.2 Hz, 2H), 7.48 (s, 1H), 7.89 (d, J=2.1 Hz, 1H), 8.01 (s, 1H)

MS (ESI$^+$) m/z 505 (M−Cl$^-$)

Example 84

Preparation of 3-Benzyloxy-7-morpholin-4-yl-4-oxo-9-(2-oxooxazolidin-3-yl)-4H-pyrido[1,2-a]pyrimidine-2-carboxylic acid methyl ester

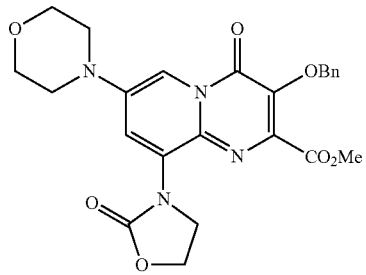

Adapted from example 57 using oxazolidin-2-one.

$^1$H NMR (300 MHz, CDCl$_3$) δ 3.19-3.30 (m, 4H), 3.90 (m, 7H), 4.54 (m, 4H), 5.32 (s, 2H), 7.29-7.55 (m, 5H), 7.93 (d, J=2.4 Hz, 1H), 8.28 (d, J=2.4 Hz, 1H)

MS (ESI$^+$) m/z 481 (M+1), 503 (M+23)

Example 85

Preparation of 3-Benzyloxy-7-morpholin-4-yl-4-oxo-9-(2-oxo-oxazolidin-3-yl)-4H-pyrido[1,2-a]pyrimidine-2-carboxylic acid [3-(4-fluoro-phenyl)-2-oxo-propyl]-amide

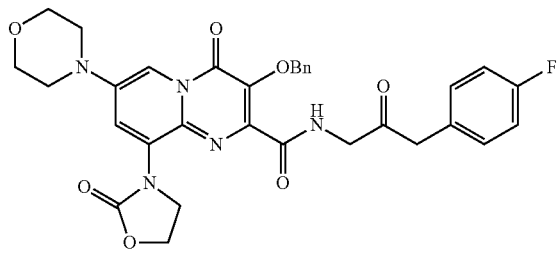

Adapted from example 1 and 2 using the product of example 84.

$^1$H NMR (300 MHz, CDCl$_3$) δ 3.17-3.30 (m, 4H), 3.77 (s, 2H), 3.82-3.94 (m, 4H), 4.33 (d, J=4.5 Hz, 2H), 4.53 (t, J=7.8 Hz, 2H), 4.66 (t, J=7.8 Hz, 2H), 5.37 (s, 2H), 7.06 (t, J=8.4 Hz, 2H), 7.14-7.39 (m, 5H), 7.50-7.61 (m, 2H), 7.90 (d, J=2.1 Hz, 1H), 8.23 (d, J=2.4 Hz, 1H), 8.27-8.36 (br, 1H)

MS (ESI$^-$) m/z 614 (M−1)

Example 86

Preparation of 3-Benzyloxy-2-[5-(4-fluoro-benzyl)-1H-imidazol-2-yl]-7-morpholin-4-yl-9-(2-oxo-oxazolidin-3-yl)-pyrido[1,2-a]pyrimidin-4-one

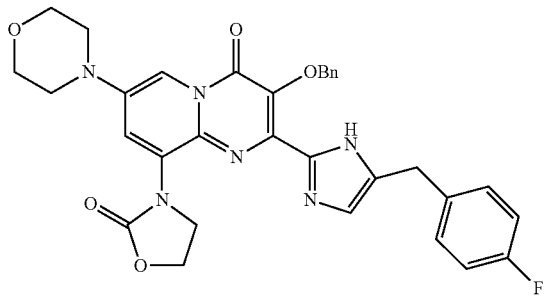

Adapted from example 76 using the product of example 85.

$^1$H NMR (300 MHz, CDCl$_3$) δ 3.18-3.33 (m, 4H), 3.82-3.99 (m, 6H), 4.63-4.80 (m, 4H), 5.40 (s, 2H), 6.84-7.04 (m, 3H), 7.09-7.21 (m, 2H), 7.28-7.40 (m, 5H), 7.94 (d, 1.5 Hz, 1H), 8.25 (s, 1H)

MS (ESI$^+$) m/z 597 (M+1)

Example 87

Preparation of 5-(4-fluorobenzyl)-2-(3-hydroxy-7-morpholino-4-oxo-9-(2-oxooxazolidin-3-yl)-4H-pyrido[1,2-a]pyrimidin-2-yl)-1H-imidazol-3-ium chloride

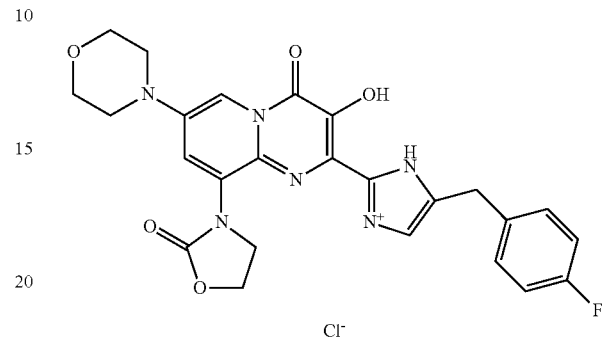

Adapted from example 77 using the product of example 86.

$^1$H NMR (300 MHz, DMSO-d$^6$) δ 3.09-3.27 (m, 4H), 3.68-3.86 (m, 4H), 4.16 (s, 2H), 4.25 (t, J=7.5 Hz, 2H), 4.58 (t, J=7.2 Hz, 2H), 7.16 (t, J=9 Hz, 2H), 7.39 (dd, J=8.2, 5.5 Hz, 2H), 7.50 (s, 1H), 7.98-8.07 (m, 2H)

MS (ESI$^+$) m/z 507 (M−Cl$^-$)

Example 88

Preparation of 3-Benzyloxy-9-(5-methyl-1,1-dioxo-1I6-[1,2,5]thiadiazolidin-2-yl)-7-morpholin-4-yl-4-oxo-4H-pyrido[1,2-a]pyrimidine-2-carboxylic acid methyl ester

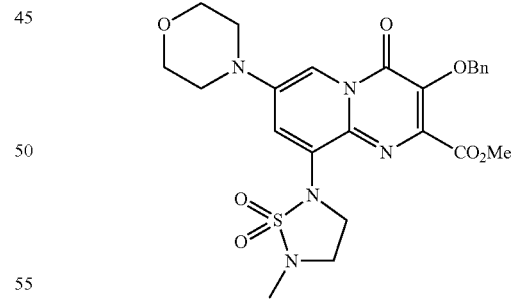

Adapted from example 57 using 2-methyl-[1,2,5]thiadiazolidine 1,1-dioxide.

$^1$H NMR (300 MHz, DMSO-d$^6$) δ 2.75 (s, 3H), 3.18-3.28 (m, 4H), 3.56 (t, J=6.6 Hz, 2H), 3.73-3.87 (m, 7H), 4.16 (t, J=6.6 Hz, 2H), 5.19 (s, 2H), 7.31-7.49 (m, 5H), 7.95 (d, J=2.4 Hz, 1H), 8.16 (d, J=2.0 Hz, 1H)

MS (ESI$^+$) m/z 530 (M+1)

Example 89

Preparation of 3-Benzyloxy-9-(5-methyl-1,1-dioxo-1l6-[1,2,5]thiadiazolidin-2-yl)-7-morpholin-4-yl-4-oxo-4H-pyrido[1,2-a]pyrimidine-2-carboxylic acid [3-(4-fluoro-phenyl)-2-oxo-propyl]-amide

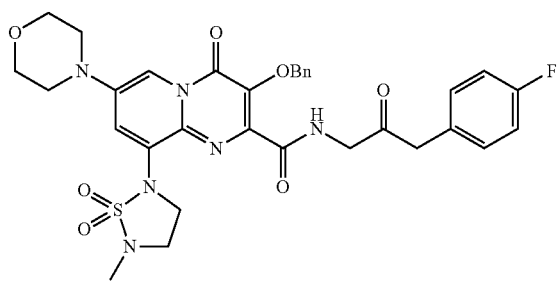

Adapted from example 1 and 2 using the product of example 88.

$^1$H NMR (300 MHz, DMSO-d$^6$) δ 2.86 (s, 3H), 3.18-3.30 (m, 6H), 3.46 (t, J=8.1 Hz, 2H), 3.81-3.96 (m, 6H), 4.23 (t, J=8.4 Hz, 2H), 5.16 (s, 2H), 6.93-7.31 (m, 10H), 7.87 (s, 1H), 8.29 (s, 1H)

Example 90

Preparation of 3-Benzyloxy-2-[5-(4-fluoro-benzyl)-1H-imidazol-2-yl]-9-(5-methyl-1,1-dioxo-1l6-[1,2,5]thiadiazolidin-2-yl)-7-morpholin-4-yl-pyrido[1,2-a]pyrimidin-4-one

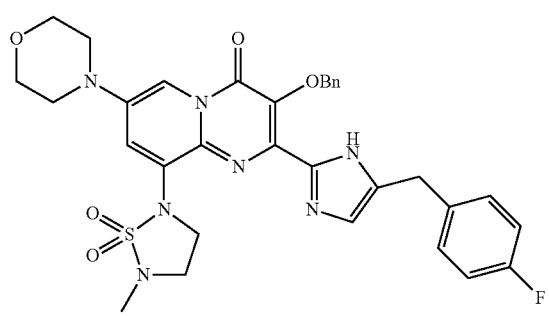

Adapted from example 76 using the product of example 89.

$^1$H NMR (300 MHz, CDCl$_3$) δ 2.84 (s, 3H), 3.11-3.29 (m, 4H), 3.59 (t, J=5.8 Hz, 2H), 3.83-3.96 (m, 4H), 4.01 (s, 2H), 4.14 (t, 5.8 Hz, 2H), 5.44 (s, 2H), 6.90-7.40 (m, 9H), 7.55-7.70 (m, 2H), 8.16 (s, 1H)

MS (ESI$^+$) m/z 646 (M+1)

Example 91

Preparation of 4-(4-Fluoro-benzyl)-2-[3-hydroxy-9-(5-methyl-1,1-dioxo-1l6-[1,2,5]thiadiazolidin-2-yl)-7-morpholin-4-yl-4-oxo-4H-pyrido[1,2-a]pyrimidin-2-yl]-3H-imidazol-1-ium; chloride

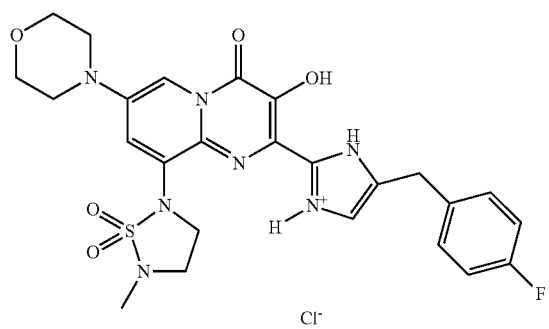

Adapted from example 77 using the product of example 90.

$^1$H NMR (300 MHz, DMSO) δ 2.85 (s, 3H), 3.10-3.23 (m, 4H), 3.55 (t, J=7.2 Hz, 2H), 3.71-3.84 (m, 4H), 4.04-4.19 (m, 4H), 7.18 (t, J=8.7 Hz, 2H), 7.35-7.44 (m, 2H), 7.50 (s, 1H), 7.82 (d, J=2.8 Hz, 1H), 7.99 (d, J=2.7 Hz, 1H)

MS (ESI$^+$) m/z 556 (M–Cl$^-$)

Example 92

Preparation of 3-Benzyloxy-9-(methanesulfonyl-methyl-amino)-7-morpholin-4-yl-4-oxo-4H-pyrido[1,2-a]pyrimidine-2-carboxylic acid methyl ester

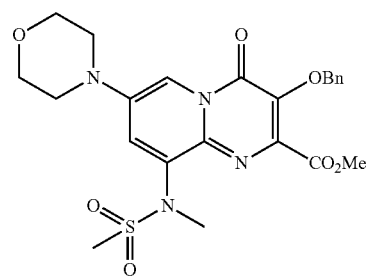

Adapted from example 57 using N-methyl-methanesulfonamide.

$^1$H NMR (300 MHz, CDCl$_3$) δ 3.16-3.29 (m, 7H), 3.42 (s, 3H), 3.83-3.95 (m, 7H), 5.32 (s, 2H), 7.30-7.57 (m, 5H), 7.72-7.90 (d, J=2.4 Hz, 1H), 8.26-8.34 (d, J=2.7 Hz, 1H)

Example 93

Preparation of 3-Benzyloxy-9-(methanesulfonyl-methyl-amino)-7-morpholin-4-yl-4-oxo-4H-pyrido[1,2-a]pyrimidine-2-carboxylic acid [3-(4-fluoro-phenyl)-2-oxo-propyl]-amide

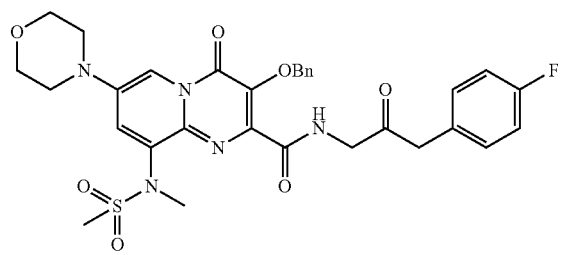

Adapted from example 1 and 2 using the product of example 92.

$^1$H NMR (300 MHz, CDCl$_3$) δ 3.17-3.32 (m, 7H), 3.46 (s, 3H), 3.77 (s, 2H), 3.82-3.94 (t, J=5.1 Hz, 4H), 4.26-4.34 (d, J=4.5 Hz, 2H), 5.38 (s, 2H), 7.00-7.11 (t, J=9 Hz, 2H), 7.15-7.38 (m, 5H), 7.49-7.60 (m, 2H), 7.71-7.78 (d, J=2.7 Hz, 1H), 8.23-8.29 (d, J=2.7 Hz, 1H), 8.34-8.44 (m, 1H)

Example 94

Preparation of N-{3-Benzyloxy-2-[5-(4-fluoro-benzyl)-1H-imidazol-2-yl]-7-morpholin-4-yl-4-oxo-4H-pyrido[1,2-a]pyrimidin-9-yl}-N-methyl-methane-sulfonamide

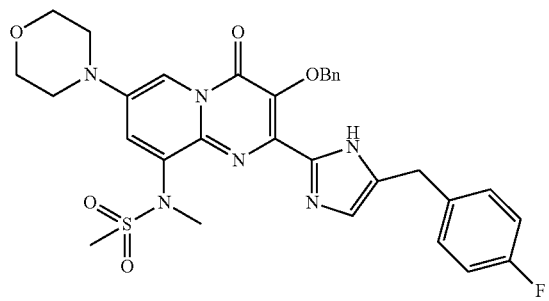

Adapted from example 76 using the product of example 93.

$^1$H NMR (300 MHz, CDCl$_3$) δ 3.16-3.29 (m, 4H), 3.45 (s, 3H), 3.50 (s, 3H), 3.82-3.96 (m, 6H), 5.41 (s, 2H), 6.90-7.20 (m, 5H), 7.32-7.50 (m, 5H), 7.70 (d, J=2.1 Hz, 1H), 8.27 (d, J=2.4 Hz, 1H)

MS (ESI$^+$) m/z 619 (M+1), 641 (M+23)

Example 95

Preparation of 5-(4-fluorobenzyl)-2-(3-hydroxy-9-(N-methylmethyl sulfonamido)-7-morpholino-4-oxo-4H-pyrido[1,2-a]pyrimidin-2-yl)-1H-imidazol-3-ium chloride

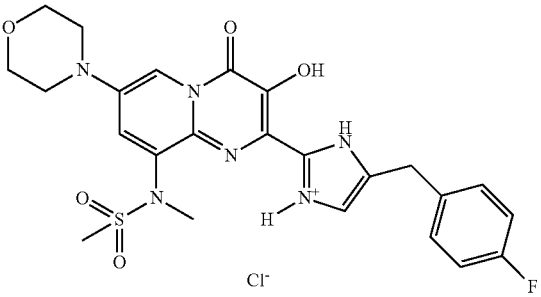

Adapted from example 77 using the product of example 94.

$^1$H NMR (300 MHz, DMSO-d$^6$) δ 3.11-3.27 (m, 7H), 3.48 (s, 3H), 3.70-3.84 (m, 4H), 4.14 (s, 2H), 7.11-7.25 (m, 2H), 7.31-7.51 (m, 3H), 7.92 (s, 1H), 8.06 (s, 1H)

MS (ESI$^+$) m/z 529 (M−Cl$^−$)

Example 96

Preparation of 3-Benzyloxy-2-[5-(4-fluoro-benzyl)-thiazol-2-yl]-7-morpholin-4-yl-9-(2-oxo-pyrrolidin-1-yl)-pyrido[1,2-a]pyrimidin-4-one

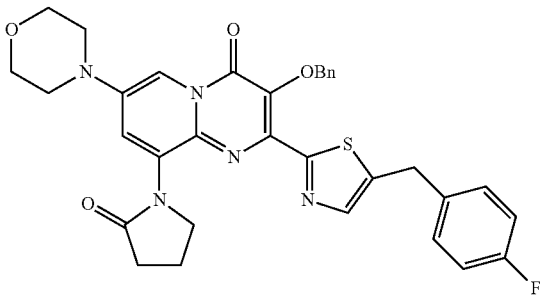

Adapted from example 9 using the product of example 81.

$^1$H NMR (300 MHz, CDCl$_3$) δ 2.25-2.40 (m, 2H), 2.65-2.79 (t, J=7.5 Hz, 2H), 3.18-3.32 (m, 4H), 3.80-4.00 (m, 6H), 4.35 (t, J=6 Hz, 2H), 5.39 (s, 2H), 6.84-7.42 (m, 10H), 7.78 (d, J=2.1 Hz, 1H), 8.24 (d, J=2.1 Hz, 1H)

MS (ESI$^+$) m/z 612 (M+1), 634 (M+23)

Example 97

Preparation of 2-[5-(4-Fluoro-benzyl)-thiazol-2-yl]-3-hydroxy-7-morpholin-4-yl-9-(2-oxo-pyrrolidin-1-yl)-pyrido[1,2-a]pyrimidin-4-one

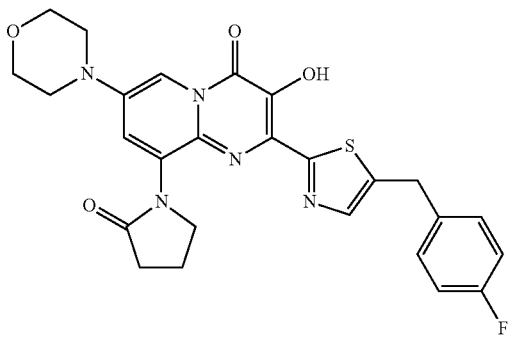

Adapted from example 60 using the product of example 96.

$^1$H NMR (300 MHz, CDCl$_3$) δ 2.12-2.26 (m, 2H), 2.40-2.60 (m, 2H), 3.12-3.26 (m, 4H), 3.70-3.85 (m, 4H), 3.90-4.04 (m, 2H), 4.16 (s, 2H), 7.08-7.51 (m, 5H), 7.66 (s, 1H), 7.90 (d, J=2.4 Hz, 1H), 8.03 (d, J=2.4 Hz, 1H)

MS (ESI$^+$) m/z 522 (M+1)

Example 98

Preparation of 3-Benzyloxy-2-[5-(4-fluoro-benzyl)-thiazol-2-yl]-9-(5-methyl-1,1-dioxo-1I6-[1,2,5]thiadiazolidin-2-yl)-7-morpholin-4-yl-pyrido[1,2-a]pyrimidin-4-one

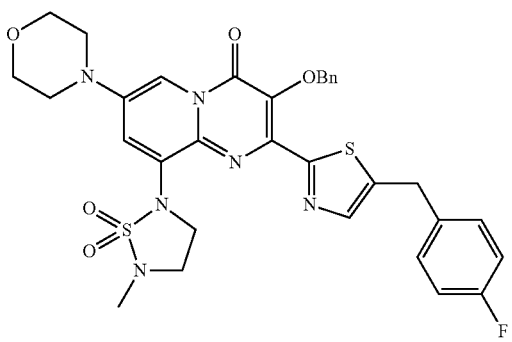

Adapted from example 9 using the product of example 89.

$^1$H NMR (300 MHz, DMSO-d$^6$) δ 2.76 (s, 3H), 3.12-3.26 (m, 4H), 3.62 (t, J=6.3 Hz, 2H), 3.72-3.85 (m, 4H), 4.21-4.35 (m, 4H), 5.23 (s, 2H), 7.18 (t, J=8.8 Hz, 2H), 7.27-7.43 (m, 5H), 7.51-7.61 (m, 2H), 7.88-7.96 (m, 2H), 8.13 (d, J=2.0 Hz, 1H)

MS (ESI$^+$) m/z 663 (M+1)

Example 99

Preparation of 2-[5-(4-Fluoro-benzyl)-thiazol-2-yl]-3-hydroxy-9-(5-methyl-1,1-dioxo-1I6-[1,2,5]thiadiazolidin-2-yl)-7-morpholin-4-yl-pyrido[1,2-a]pyrimidin-4-one

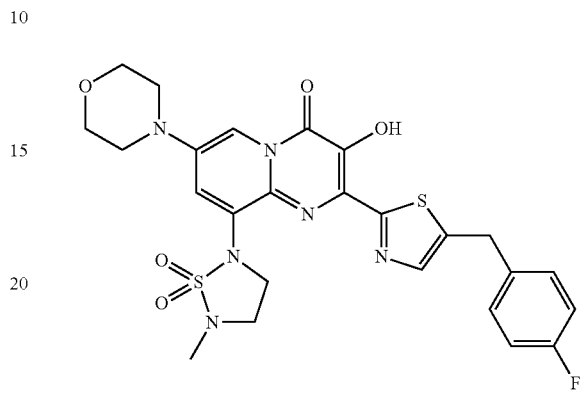

Adapted from example 60 using the product of example 98.

$^1$H NMR (300 MHz, DMSO-d$^6$) δ 2.75 (s, 3H), 3.11-3.22 (m, 4H), 3.58 (t, J=6.5 Hz, 2H), 3.72-3.84 (m, 4H), 4.22 (t, J=6.6 Hz, 2H), 4.32 (s, 2H), 7.18 (t, J=8.8 Hz, 2H), 7.38 (dd, J=5.5, 8.7 Hz, 2H), 7.79 (d, J=2.0 Hz, 1H), 7.94 (s, 1H), 8.00 (d, J=2.0 Hz, 1H), 11.46 (s, 1H)

MS (ESI$^-$) m/z 571 (M−1)

Example 100

Preparation of 3-Benzyloxy-2-[5-(4-fluoro-benzyl)-thiazol-2-yl]-9-(3-methyl-2-oxo-imidazolidin-1-yl)-7-morpholin-4-yl-pyrido[1,2-a]pyrimidin-4-one

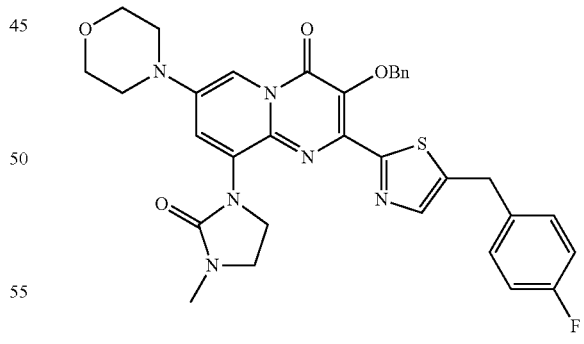

Adapted from example 1, 2 and 9 using the product of example 57.

$^1$H NMR (300 MHz, CDCl$_3$) δ 2.93 (s, 3H), 3.18-3.29 (m, 4H), 3.61 (t, J=8.4 Hz, 2H), 3.80-3.93 (m, 4H), 4.19 (s, 2H), 4.43 (t, J=8.4 Hz, 2H), 5.42 (s, 2H), 7.03 (t, J=8.4 Hz, 2H), 7.12-7.35 (m, 5H), 7.48-7.56 (m, 2H), 7.83 (s, 1H), 7.91 (d, J=2.1 Hz, 1H), 8.22 (d, J=1.8 Hz, 1H)

MS (ESI$^+$) m/z 627 (M+1), 649 (M+23)

Example 101

Preparation of 2-[5-(4-Fluoro-benzyl)-thiazol-2-yl]-3-hydroxy-9-(3-methyl-2-oxo-imidazolidin-1-yl)-7-morpholin-4-yl-pyrido[1,2-a]pyrimidin-4-one

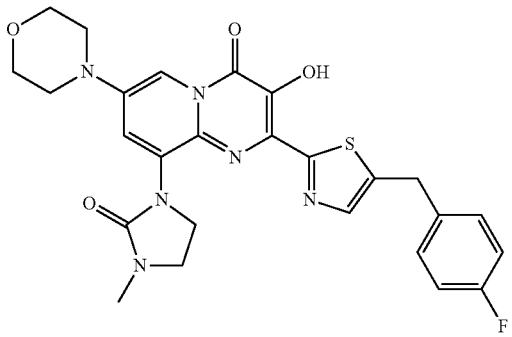

Adapted from example 53 using the product of example 100.

$^1$H NMR (300 MHz, CDCl$_3$) δ 2.94 (s, 3H), 3.15-3.27 (m, 4H), 3.57 (t, J=8.7 Hz, 2H), 3.80-3.93 (m, 4H), 4.17-4.31 (m, 4H), 7.05 (t, J=8.7 Hz, 2H), 7.17-7.29 (m, 2H), 7.66 (s, 1H), 7.71 (s, 1H), 8.20 (s, 1H)

MS (ESI$^+$) m/z 537 (M+1), 559 (M+23)

Example 102

Preparation of 3-Benzyloxy-2-[(5-(4-fluoro-benzyl)-thiazol-2-yl]-7-morpholin-4-yl-9-(2-oxo-oxazolidin-3-yl)-pyrido[1,2-a]pyrimidin-4-one

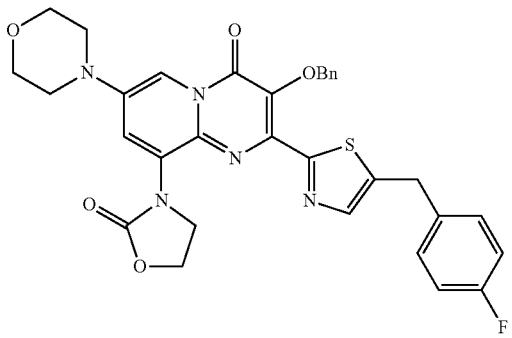

Adapted from example 9 using the product of example 85.

$^1$H NMR (300 MHz, CDCl$_3$) δ 3.23 (t, J=5.4 Hz, 4H), 3.89 (t, J=5.1 Hz, 4H), 4.19 (s, 2H), 4.63 (m, 4H), 5.43 (s, 2H), 7.04 (t, J=8.4 Hz, 2H), 7.15-7.37 (m, 5H), 7.47-7.57 (m, 2H), 7.82 (s, 1H), 7.90 (d, J=2.4 Hz, 1H), 8.26 (d, J=2.7 Hz, 1H)

MS (ESI$^+$) m/z 614 (M+1), 636 (M+23)

Example 103

Preparation of 2-[5-(4-Fluoro-benzyl)-thiazol-2-yl]-3-hydroxy-7-morpholin-4-yl-9-(2-oxo-oxazolidin-3-yl)-pyrido[1,2-a]pyrimidin-4-one

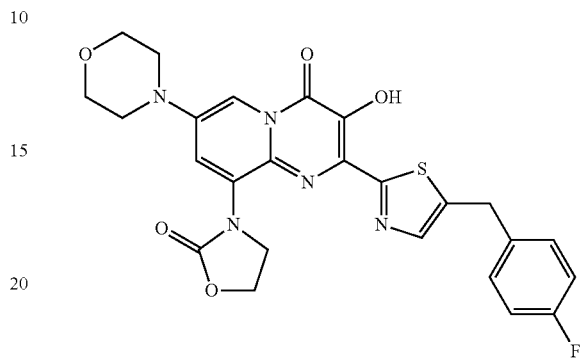

Adapted from example 53 using the product of example 102.

$^1$H NMR (300 MHz, CDCl$_3$) δ 3.20 (t, J=4.8 Hz, 4H), 3.89 (t, J=4.4 Hz, 4H), 4.22 (s, 2H), 4.42 (t, J=7.8 Hz, 2H), 4.61 (t, J=7.8 Hz, 2H), 7.05 (t, J=8.7 Hz, 2H), 7.19-7.29 (m, 2H), 7.66 (s, 1H), 7.70 (d, J=2.4 Hz, 1H), 8.23 (d, J=2.4 Hz, 1H)

MS (ESI$^+$) m/z 524 (M+1), 546 (M+23)

Example 104

Preparation of 3-Benzyloxy-9-(1,1-dioxo-1l6-isothiazolidin-2-yl)-2-[5-(4-fluoro-benzyl)-thiazol-2-yl]-7-morpholin-4-yl-pyrido[1,2-a]pyrimidin-4-one

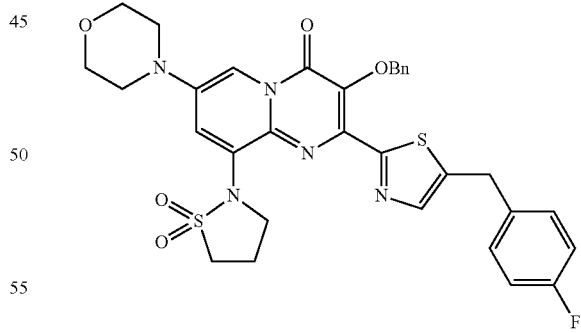

Adapted from example 57 1, 2 and 9 using isothiazolidine 1,1-dioxide.

$^1$H NMR (300 MHz, DMSO-d$^6$) δ 2.48-2.64 (m, 2H? overlapped?), 3.17-3.27 (m, 4H), 3.67-3.84 (m, 6H), 3.98 (t, J=7.0 Hz, 2H), 4.27 (s, 2H), 5.26 (s, 2H), 7.18 (t, J=9.0 Hz, 2H), 7.30-7.42 (m, 2H), 7.48-7.70 (m, 5H), 7.89 (s, 1H), 7.99 (d, J=2.3 Hz, 1H), 8.14 (d, J=2.3 Hz, 1H)

MS (ESI$^+$) m/z 648 (M+1)

Example 105

Preparation of 9-(1,1-Dioxo-1I6-isothiazolidin-2-yl)-2-[5-(4-fluoro-benzyl)-thiazol-2-yl]-3-hydroxy-7-morpholin-4-yl-pyrido[1,2-a]pyrimidin-4-one

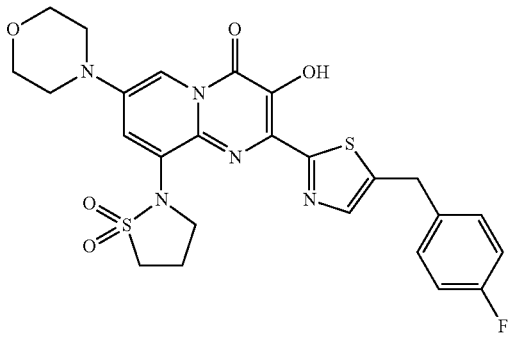

Adapted from example 53 using the product of example 104.

$^1$H NMR (300 MHz, DMSO-d$^6$) δ 2.54-2.68 (m, 2H), 2.97-3.08 (m, 4H), 3.69-3.78 (m, 4H), 3.83-4.02 (m, 4H), 4.13 (s, 2H), 7.07-7.18 (m, 3H), 7.31 (dd, J=5.9, 8.9 Hz, 2H), 7.54 (s, 1H), 7.71 (d, J=2.5 Hz, 1H).

MS (ESI$^-$) m/z 556 (M−1)

Example 106

Preparation of 3-Benzyloxy-9-(1,1-dioxo-1I6-isothiazolidin-2-yl)-7-morpholin-4-yl-4-oxo-4H-pyrido[1,2-a]pyrimidine-2-carboxylic acid [3-(3,4-dichloro-phenyl)-2-oxo-propyl]-amide

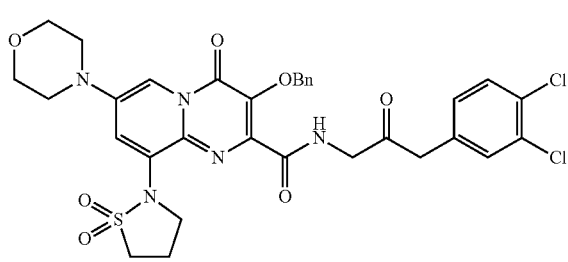

Adapted from example 57, 1, and 2 using isothiazolidine 1,1-dioxide.

$^1$H NMR (300 MHz, CDCl$_3$) δ 2.63-2.77 (m, 2H), 3.17-3.28 (m, 4H), 3.60 (t, J=7.3 Hz, 2H), 3.77 (s, 2H), 3.83-3.94 (m, 4H), 4.09 (t, J=7.0 Hz, 2H), 4.31 (d, J=4.8 Hz, 2H), 5.34 (s, 2H), 6.83 (d, J=8.8 Hz, 2H), 7.05 (d, J=8.6 Hz, 2H), 7.15-7.25 (m, 2H), 7.48 (d, J=8.7 Hz, 2H), 7.73 (d, J=2.5 Hz, 1H), 8.22 (d, J=2.6 Hz, 1H), 8.60 (t, J=4.7 Hz, 1H)

MS (ESI$^+$) m/z 700 (M+1)

Example 107

Preparation of Acetic acid 2-[5-(3,4-dichloro-benzyl)-thiazol-2-yl]-9-(1,1-dioxo-1I6-isothiazolidin-2-yl)-7-morpholin-4-yl-4-oxo-4H-pyrido[1,2-a]pyrimidin-3-yl ester

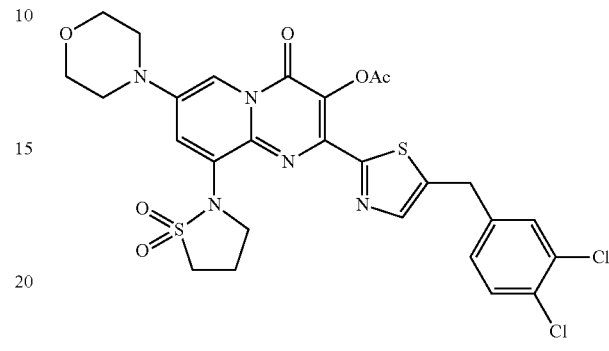

Adapted from example 9 of the present application and example 171 of co-pending International Patent Application filed 2 Jul. 2009 to Avexa Ltd entitled "Imidazopyrimidinones and uses thereof" using product of example 106 of the present application.

$^1$H NMR (300 MHz, CDCl$_3$) δ 2.47 (s, 3H), 2.57-2.72 (m, 2H), 3.23 (t, J=4.7 Hz, 4H) □ 3.48 (t, J=7.3 Hz, 2H), 3.88 (t, J=4.8 Hz, 4H), 4.12-4.30 (m, 4H), 7.08 (dd, J=2.2, 8.7 Hz, 1H), 7.36 (d, J=2.0 Hz, 1H), 7.42 (d, J=8.3 Hz, 1H), 7.71 (s, 1H), 7.88 (d, J=2.4 Hz, 1H), 8.28 (d, J=2.4 Hz, 1H).

MS (ESI$^+$) m/z 650 (M+1)

Example 108

Preparation of 2-[5-(3,4-Dichloro-benzyl)-thiazol-2-yl]-9-(1,1-dioxo-1I6-isothiazolidin-2-yl)-3-hydroxy-7-morpholin-4-yl-pyrido[1,2-a]pyrimidin-4-one

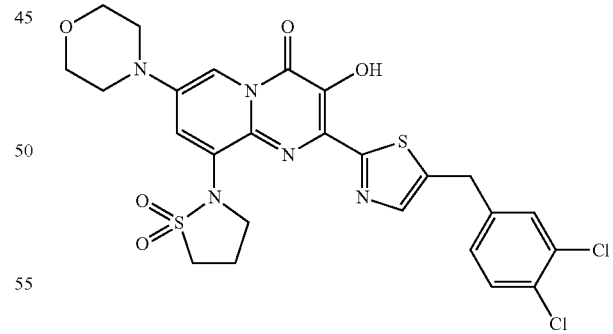

Adapted from example 172 of co-pending International Patent Application filed 2 Jul. 2009 to Avexa Ltd entitled "Imidazopyrimidinones and uses thereof" using the product of example 107.

$^1$H NMR (300 MHz, DMSO-d$^6$) δ 2.54-2.68 (m, 2H), 2.98-3.08 (m, 4H), 3.68-3.78 (m, 4H), 3.83-4.00 (m, 4H), 4.17 (s, 2H), 7.12 (d, J=2.1 Hz, 1H), 7.29 (dd, J=2.0, 8.2 Hz, 1H), 7.53-7.61 (m, 3H), 7.72 (d, J=2.3 Hz, 1H)

MS (ESI$^-$) m/z 606 (M−1)

Example 109

5-(4-Fluoro-benzyl)-2-[3-hydroxy-9-(3-methyl-2-oxo-imidazolidin-1-yl)-7-morpholin-4-yl-4-oxo-4H-pyrido[1,2-a]pyrimidin-2-yl]-1H-imidazol-1-ium; chloride

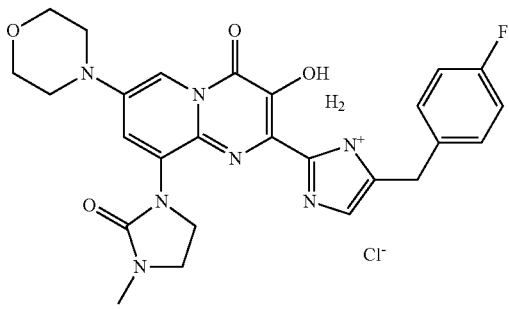

Adapted from example 1, 2, 44 and 45 using the product of example 57.

$^1$H NMR (300 MHz, DMSO-d$^6$) δ: 7.98 (m, 1H), 7.79 (m, 1H), 7.45 (s, 1H), 7.38 (m, 2H), 7.16 (m, 2H), 4.09 (m, 4H), 3.78 (m, 4H), 3.53 (m, 2H), 3.16 (m, 4H), 2.84 (s, 3H).

MS (ESI$^-$) m/z 520 (M+1)

3 Biological Examples

Example 3.1

Activity of Selected Examples Against Wild Type and Mutant Integrases and HIV-s

PhenoScreen Assay

Monogram Bioscience' PhenoScreen assay allows the evaluation of integrase inhibitors for activity against a variety of HIV variants. The assay uses virus generated from 2 DNA constructs; one containing the HIV LTR, gag and pol regions, as well as a luciferase reporter gene in place of the viral envelope genes, and a second DNA construct containing the amphotrophic murine leukemia virus (A-MLV) envelope gene required to pseudotype virions and render them capable of entry into a target cell. Viruses generated using these constructs by transfection into a producer cell line such as 293T are capable of one-round of infection only. Successful integration events are directly proportional to the levels of luciferase expression 48 h after infection.

The viral variants chosen by the present inventors to screen integration inhibitors consist of mutations within the viral integrase enzyme known to confer resistance to a number of known integration inhibitors published in the literature. In particular, the viral variants containing the Q148H/G140S double mutation in integrase, and the N155H/E92Q double mutation in integrase, represent two of the more common viruses identified to arise in patients that are failing treatment with Isentress (Raltegravir, MK-0518).

IN-Screen Assay

Similar to the PhenoScreen assay, the IN-Screen assay relies on reporter gene expression levels 58 h following infection. However, in contrast to the PhenoScreen assay developed at Monogram Bioscie Mutant Enzymes:

HIV integrase was mutated within a shuttle vector (pGEM) containing the majority of the HIV-1 gag and pol sequence using site directed mutagenesis to generate integrase sequences that have been published as conferring resistance to published integrase inhibitors. These include, but are not limited to, mutations such as Q148K. The integrase coding region was then subject to PCR and cloned into a bacterial expression vector. The specific introduction of desired mutation(s) was confirmed by sequence analysis. Proteins were expressed, purified and used in strand transfer assays.

Strand Transfer Assay (Enzyme Assay):

A strand transfer assay procedure similar to that published (Ovenden et al. Phytochemistry. 2004 December; 65(24): 3255-9.) is used. Briefly, 400 ng of the enzyme, wild type or drug resistant mutant, is mixed with the compound to be tested and incubated with 30 nM substrate DNA. The substrate DNA is designed to mimic HIV DNA termini that has undergone 3' end processing, and consists of the annealed U5 LTR sequence oligonucleotides tagged with Digoxigenin (DIG; 5'-ACTGCTAGAGATTTTCCACACTGAC-TAAAAGGGTC-DIG-3') or biotin (5'-Bio-GACCCTTT-TAGTCAGTGTGGAAAATCTCTAGCA-3') so that each substrate has either a DIG or Bio tag on opposite strands. Reactions are carried out for 1 hr at 37° C. Products generated as a result of strand transfer activity are bound to streptavidin plates and detected using anti-DIG-alkaline phosphatase conjugate and p-nitro phenyl phosphate substrate.

TABLE 1

Activity of selected examples against wild type and mutant integrases and HIV-s

| | Phenosense assay | | | | | |
| --- | --- | --- | --- | --- | --- | --- |
| Compound | WT | Y143R | E92Q/ N155H | G140S Q148H | T125K F121Y | T66I S153Y |
| Example 41 | ++++ | ++++ | +++ | +++ | ++++ | ++++ |

TABLE 1-continued
Activity of selected examples against wild type and mutant integrases and HIV-s
| Compound | Phenosense assay | | | | | |
|---|---|---|---|---|---|---|
| | WT | Y143R | E92Q/ N155H | G140S Q148H | T125K F121Y | T66I S153Y |
| Example 42 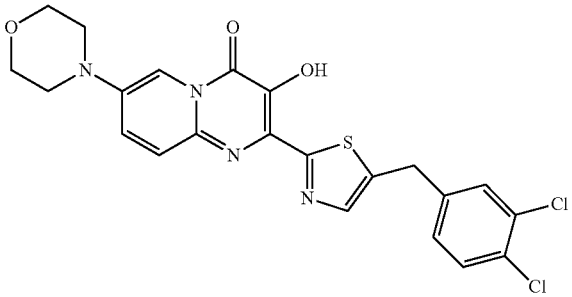 | +++ | +++ | +++ | ++ | +++ | +++ |
| Comparative example 1 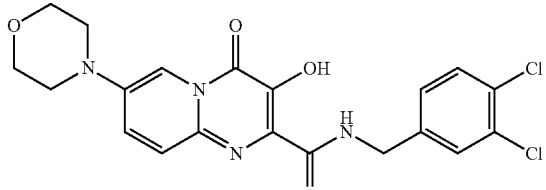 | ++++ | N/A | + | + | N/A | N/A |
| Comparative example 2 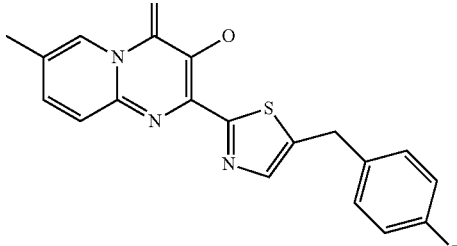 | +++ | +++ | ++ | ++ | +++ | +++ |
| Example 7 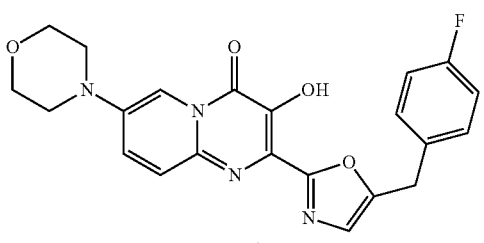 | ++++ | ++++ | +++ | ++ | +++ | ++++ |
| Example 4 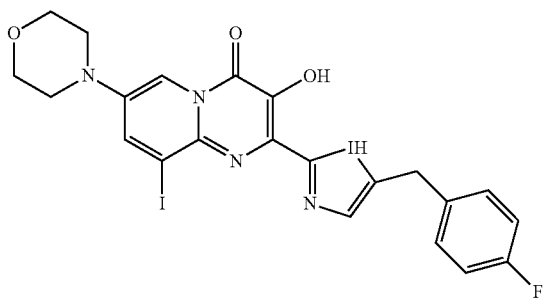 | ++++ | ++++ a | ++++ b | ++++ | + a | ++++ |

TABLE 1-continued

Activity of selected examples against wild type and mutant integrases and HIV-s

| Compound | Phenosense assay | | | | | |
|---|---|---|---|---|---|---|
| | WT | Y143R | E92Q/ N155H | G140S Q148H | T125K F121Y | T66I S153Y |
| 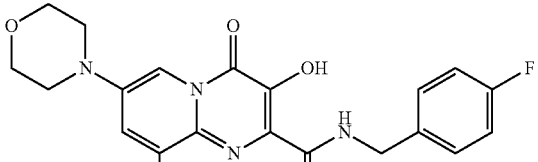<br>Comparative example 3 | ++++ | ++++ | ++++ | + | ++++ | ++++ |

++++ indicates value between 0.001 μM and 0.1 μM
+++ indicates value between 0.1 μM and 1 μM
++ indicates value between 1 μM and 10 μM
+ indicates value greater than 10 μM
a 2.5-fold improvement in activity over comparative example 3
b 2-fold improvement in activity over comparative example 3

The compounds of the present invention have superior activity profiles against mutant HIV integrases than "amide" analogues which are not of the present invention.

Example 3.2

Reporter Viruses

Infectivity assays using reporter viruses derived from lentiviral vectors capable of a single round of infection were used to determine the activity ($EC_{50}$) of compounds. The DNA used to generate viruses for infection was the full-length HIV-1 genome which had been envelope-deleted. In addition, a reporter gene (the firefly luciferase gene from *Photinus pyralis*) was cloned into the nef region of the HIV backbone for ease of assay readout. Viruses were generated via liposomal transfection of the lentiviral-derived DNA backbone together with a vesicular stomatitis virus glycoprotein (VSV-G) expression plasmid into 293T cells. Culture supernatants containing VSV-G pseudotyped virions were harvested 64 h post transfection, clarified by centrifugation to remove cell debris, and frozen at −70° C. until use.

Mutant Integrase Viruses:

HIV integrase was mutated within a shuttle vector (pGEM) containing the majority of the HIV-1 gag and pol sequence using site-directed mutagenesis to generate sequences that are known to confer resistance to published integrase inhibitors. These include but are not limited to mutations such as Q148H/G140S (in table # QHGS), N155H/E92Q (in table # NHEQ), F121Y/T124K (in table FYTK), Y143R (in table # Y143R) and the triple mutant Q148KJG140A/E138A. (in table# QKGAEA). The mutated integrase coding region within the shuttle vector was sequence verified, and then exchanged for the wild-type (WT) coding sequence in the reporter virus DNA backbone.

Assay Method:

293T cells were plated out at 12000 cells per well in CellView 96-well cell culture plates (Invitrogen) 16 h prior to compound addition. Compounds were preincubated with cells for 4 h at 37° C. prior to the addition of virus sufficient to generate approximately 10000 Luciferase light units (as measured by the Victor Wallace luminometer) upon assaying using the Bright-Glo™ reagent (Promega) according to the manufacturer's instructions at 48 h post infection.

| Compound | Luciferase assay results | | | | | |
|---|---|---|---|---|---|---|
| | WT | QHGS | NHEQ | FYTK | Y143R | QKGAEA |
| 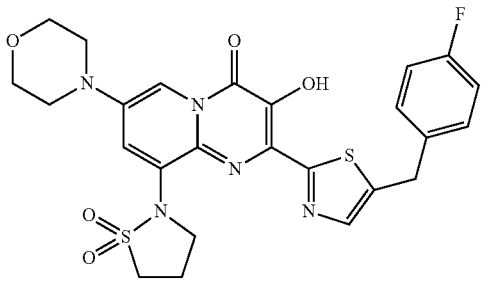<br>Example 105 | +++ | ++ | +++ | +++ | +++ | ++ |

-continued

| Compound | Luciferase assay results | | | | | |
|---|---|---|---|---|---|---|
| | WT | QHGS | NHEQ | FYTK | Y143R | QKGAEA |
| Example 103 | +++ | +++ | +++ | +++ | +++ | ++ |
| Example 101 | +++ | +++ | +++ | +++ | +++ | ++ |
| Example 99 | +++ | +++ | +++ | +++ | +++ | ++ |
| Example 109 | +++ | ++ | ++ | ND | ND | ND |

-continued
| Compound | Luciferase assay results | | | | | |
|---|---|---|---|---|---|---|
| | WT | QHGS | NHEQ | FYTK | Y143R | QKGAEA |
| 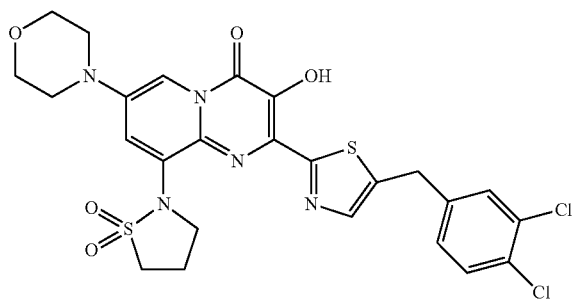 Example 108 | +++ | ++ | ND | ND | ND | ND |
| 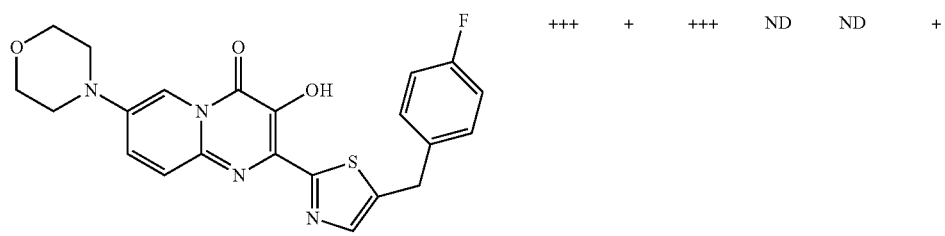 Example 41 | +++ | + | +++ | ND | ND | + |
| 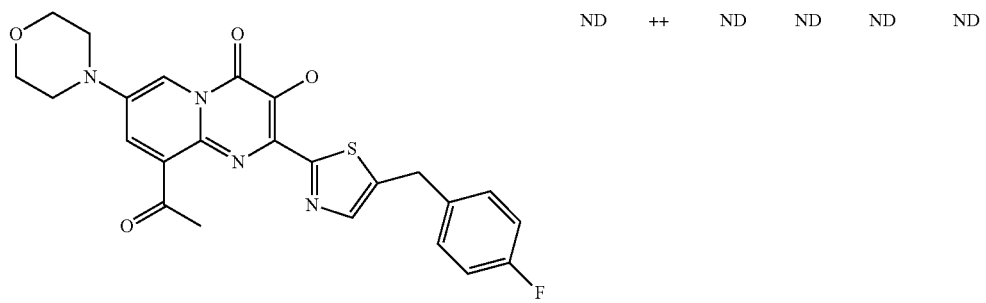 Example 53 | ND | ++ | ND | ND | ND | ND |
| 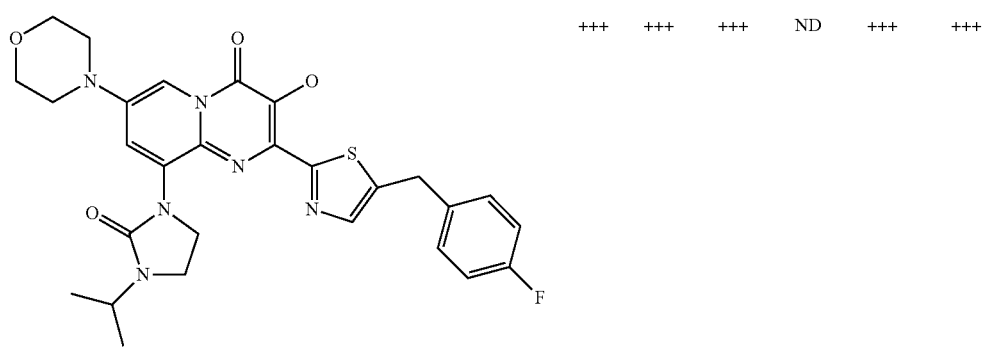 Example 56 | +++ | +++ | +++ | ND | +++ | +++ |

-continued

| Compound | Luciferase assay results | | | | | |
|---|---|---|---|---|---|---|
| | WT | QHGS | NHEQ | FYTK | Y143R | QKGAEA |
| Example 60 | +++ | +++ | +++ | ND | +++ | +++ |
| Example 70 | +++ | +++ | +++ | ND | ND | ND |
| Example 72 | ND | ++ | ND | ND | ND | ND |
| Example 77 | +++ | ++ | +++ | ND | ND | ND |

-continued
| Compound | Luciferase assay results | | | | | |
|---|---|---|---|---|---|---|
| | WT | QHGS | NHEQ | FYTK | Y143R | QKGAEA |
| 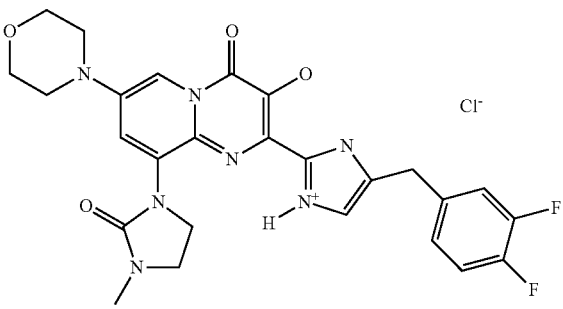 Example 79 | +++ | ++ | +++ | ND | ND | ND |
| 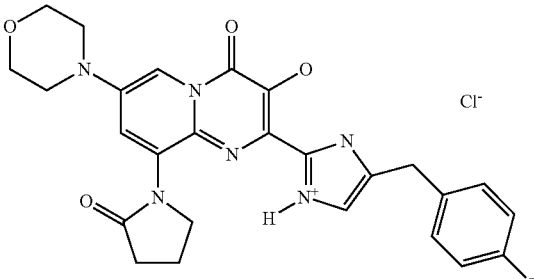 Example 83 | ND | ++ | ND | ND | ND | ND |
| 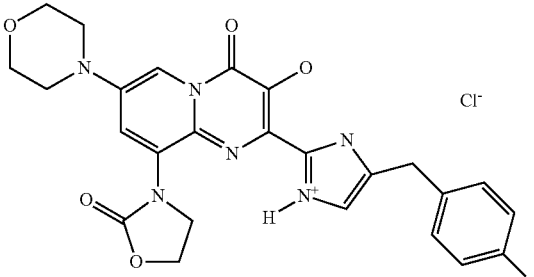 Example 87 | ND | ++ | ND | ND | ND | ND |
| 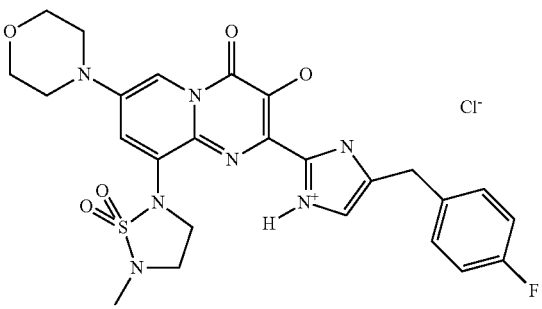 Example 91 | +++ | +++ | +++ | ND | ND | ND |

| Compound | Luciferase assay results | | | | | |
|---|---|---|---|---|---|---|
| | WT | QHGS | NHEQ | FYTK | Y143R | QKGAEA |
| 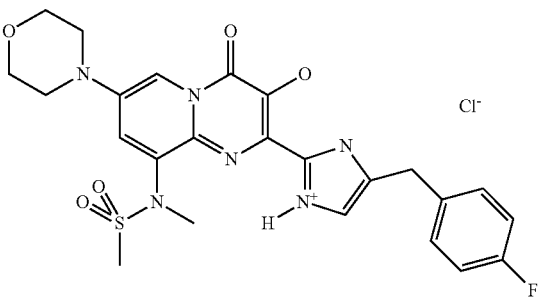 Example 95 | +++ | ++ | +++ | ND | ND | ND |
| 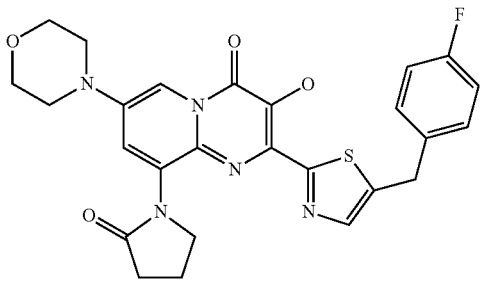 Example 97 | ND | ++ | ND | ND | ND | ND |
| 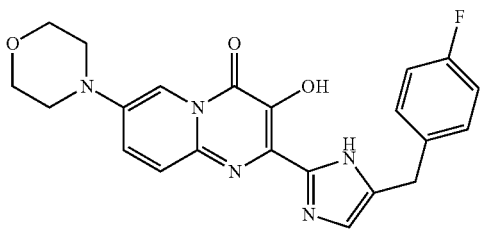 Example 45 | +++ | ++ | ++ | ++ | ++ | ++ |
| 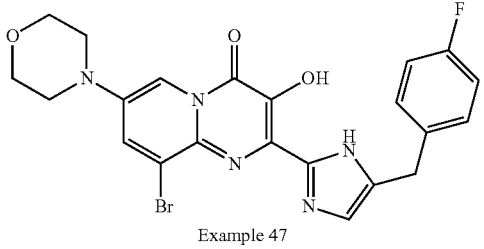 Example 47 | ND | ++ | ND | ND | ND | ND |

The compounds of the present invention show activity against the triple mutant QKGAEA which is resistant to many published integrase inhibitors.

$EC_{50}$ 1 nM-100 nM=+++
$EC_{50}$ 100 nM to 1 uM=++
$EC_{50}$>1 uM=+
ND: Not determined Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

All publications mentioned in this specification are herein incorporated by reference. Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed in Australia or elsewhere before the priority date of each claim of this application.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

The invention claimed is:
1. A compound of Formula II or a pharmaceutically acceptable salt thereof wherein:

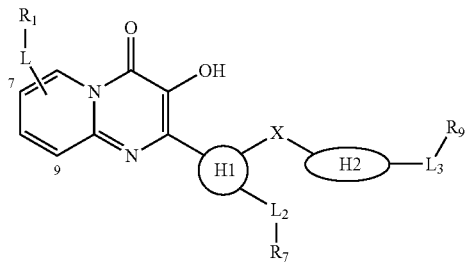

L-R$_1$ is 1-3 substituents wherein:
  each L is independently absent or is selected from the group consisting of Z, C$_{1-3}$alkylene, —C=Z, —CZ$_2$—, —C(=Z)C$_{1-3}$alkylene, —CZ$_2$—C$_{1-3}$alkylene, —C$_{1-3}$alkylene-C(=Z)—, and —C$_{1-3}$alkylene-CZ$_2$— wherein each Z is independently selected from O, S, and NH;
  each R$_1$ is independently selected from the group consisting of hydrogen, C$_{1-10}$alkyl wherein one or more of the carbon atoms of the alkyl chain may optionally be replaced with oxygen atoms, C$_{1-10}$alkylNR$_3$R$_4$, halo, NR$_3$R$_4$, alkylaryl, S(O)NR$_3$R$_4$, SO$_2$NR$_3$R$_4$, SO$_2$C$_{1-10}$alkyl, and C$_{5-10}$cycloalkyl wherein one or more of the carbon atoms of the cycloalkyl ring are replaced with one or more oxygen atoms;
  R$_3$ and R$_4$ are each independently selected from the group consisting of hydrogen, C$_{3-6}$cycloalkyl, C$_{1-10}$alkyl, C$_{1-10}$NR$_5$R$_6$, —(CO)(CO)NR$_5$R$_6$; or R$_3$ and R$_4$ taken together with the attached nitrogen form a 5-7 membered heterocyclic ring which contains zero to two additional heteroatoms selected from N, O or S where S can be at the S, S(O) or S(O)$_2$ oxidation state and wherein said heterocyclic ring is optionally substituted at the carbon or nitrogen atoms with one or more substituents selected from halo, C$_{1-4}$alkyl, CO$_2$C$_{1-4}$alkyl, NR$_5$R$_6$; C$_{1-4}$alkylNR$_5$R$_6$;
  R$_5$ and R$_6$ are each independently selected from the group consisting of H and C$_{1-4}$-alkyl or R$_5$ and R$_6$ together with the attached nitrogen form a 5-7 membered heterocyclic ring which contains zero to two additional heteroatoms selected from N, O or S where S can be at the S, S(O) or S(O)$_2$ oxidation state and wherein said heterocyclic ring is optionally substituted at the carbon or nitrogen atoms with one or more substituents selected from halo and C$_{1-4}$alkyl;
  when R$_1$ is alkylaryl, the aryl group of said alkylaryl substituent is optionally substituted with a substituent selected from C$_{1-10}$alkyl, —O—C$_{1-10}$alkyl, C$_{1-10}$alkylNR$_3$R$_4$, —O—C$_{1-10}$alkylNR$_3$R$_4$, halo, NR$_3$R$_4$, alkylaryl, —O-alkylaryl, SO$_2$NR$_3$R$_4$, provided that at least one L-R$_1$ is morpholino;
H$_1$ is a five membered aromatic heterocycle selected from the group consisting of thiazole, oxazole, oxadiazole, thiadiazole imidazole, triazole, and tetrazole;
L$_2$-R$_7$ is 0-2 substituents wherein:
  each L$_2$ is independently absent or is selected from the group consisting of Z, C$_{1-3}$alkylene, —C=Z, —CZ$_2$—, —C(=Z)C$_{1-3}$alkylene, —CZ$_2$—C$_{1-3}$alkylene, —C$_{1-3}$alkylene-C(=Z)—, and —C$_{1-3}$alkylene-CZ$_2$— wherein each Z is independently selected from O, S, and NH;
  each R$_7$ is independently selected from the group consisting of hydrogen, C$_{1-10}$alkyl wherein one or more of the carbon atoms of the alkyl chain may optionally be replaced with oxygen atoms, C$_{1-10}$alkylNR$_3$R$_4$, halo, NR$_3$R$_4$, alkylaryl, S(O)NR$_3$R$_4$, SO$_2$NR$_3$R$_4$, SO$_2$C$_{1-10}$alkyl, and C$_{5-10}$cycloalkyl wherein one or more of the carbon atoms of the cycloalkyl ring are optionally replaced with one or more oxygen atoms;
X is CR$_8$R$_{8'}$;
  each of R$_8$ and R$_{8'}$ is independently selected from the group consisting of H and CH$_3$;
H$_2$ is phenyl;
L$_3$-R$_9$ is 0-3 substituents wherein:
  each L$_3$ is independently absent or is selected from the group consisting of Z, C$_{1-3}$alkylene, —C=Z, —CZ$_2$—, —C(=Z)C$_{1-3}$alkylene, —CZ$_2$—C$_{1-3}$alkylene, —C$_{1-3}$alkylene-C(=Z)—, and —C$_{1-3}$alkylene-CZ$_2$— wherein each Z is independently selected from O, S, and NH;
  each R$_9$ is independently selected from the group consisting of hydrogen, C$_{1-10}$alkyl wherein one or more of the carbon atoms of the alkyl chain may optionally be replaced with oxygen atoms, C$_{1-10}$alkylNR$_3$R$_4$, halo, NR$_3$R$_4$, heterocyclyl, heteroaryl, alkylaryl, S(O)NR$_3$R$_4$, SO$_2$NR$_3$R$_4$, SO$_2$C$_{1-10}$alkyl, and C$_{5-10}$cycloalkyl wherein one or more of the carbon atoms of the cycloalkyl ring are optionally replaced with one or more oxygen atoms.

2. A compound according to claim 1 wherein H$_1$ is selected from the group consisting of imidazole and thiazole.

3. A compound according to claim 1 wherein L$_2$-R$_7$ is absent.

4. A compound according to claim 1 wherein L$_3$-R$_9$ is at least 2 substituents wherein the first L$_3$-R$_9$ is halo and in the second L$_3$-R$_9$, L$_3$ is absent or is selected from —C=O and R$_9$ is selected from the group consisting of halo, NR$_3$R$_4$ and SO$_2$NR$_3$R$_4$.

5. A compound according to claim 1 wherein L-R$_1$ is at least 2 substituents wherein the first L-R$_1$ is halo.

6. A compound according to claim 1 wherein L-R$_1$ consists of two substituents at positions 7 and 9.

7. A compound according to claim 1 selected from the group consisting of:

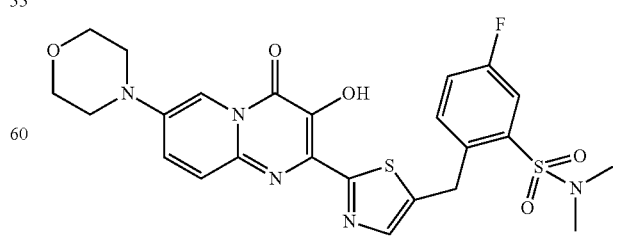

5-Fluoro-2-[2-(3-hydroxy-7-morpholin-4-yl-4-oxo-4H-pyrido[1,2-a]pyrimidin-2-yl)-thiazol-5-ylmethyl]-N,N-dimethyl-benzenesulfonamide;

-continued

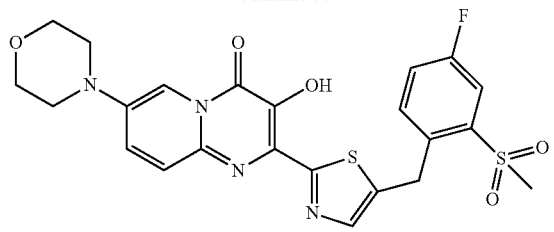

2-[5-(4-Fluoro-2-methanesulfonyl-benzyl)-thiazol-2-yl]-3-hydroxy-7-morpholin-4-yl-pyrido[1,2-a]pyrimidin-4-one;

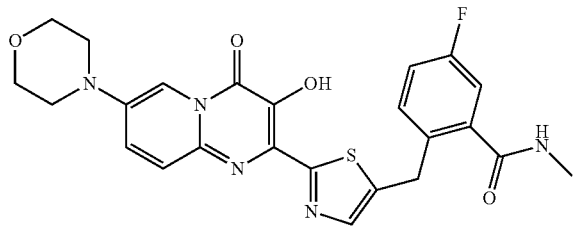

5-Fluoro-2-[2-(3-hydroxy-7-morpholin-4-yl-4-oxo-4H-pyrido[1,2-a]pyrimidin-2-yl)-thiazol-5-ylmethyl]-N-methyl-benzamide;

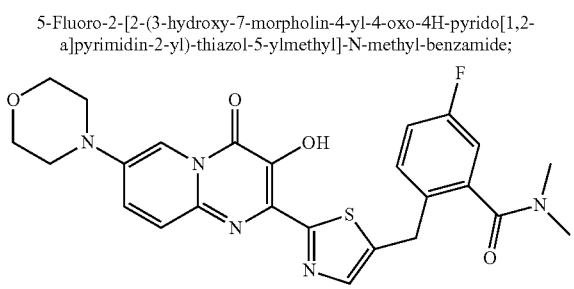

5-Fluoro-2-[2-(3-hydroxy-7-morpholin-4-yl-4-oxo-4H-pyrido[1,2-a]pyrimidin-2-yl)-thiazol-5-ylmethyl]-N-methyl-benzamide;

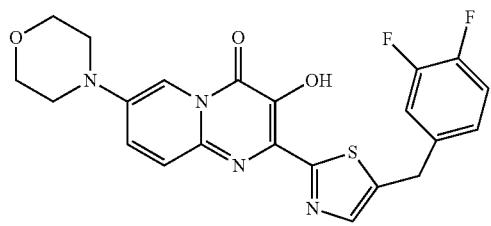

2-[5-(3,4-Difluoro-benzyl)-thiazol-2-yl]-3-hydroxy-7-morpholin-4-yl-pyrido[1,2-a]pyrimidin-4-one;

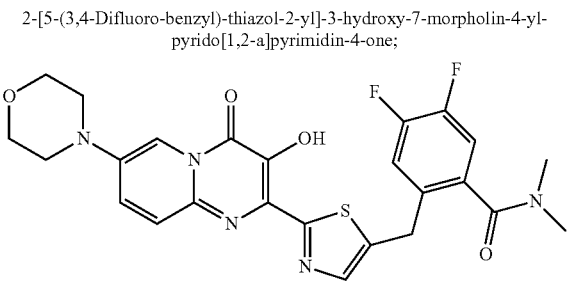

4,5-Difluoro-2-[2-(3-hydroxy-7-morpholin-4-yl-4-oxo-4H-pyrido[1,2-a]pyrimidin-2-yl)thiazol-5-ylmethyl]-N,N-dimethyl-benzamide;

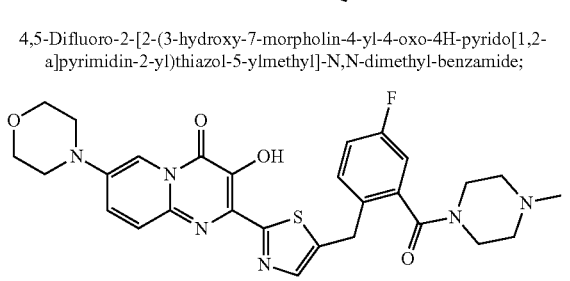

2-{5-[4-Fluoro-2-(4-methyl-piperazine-1-carbonyl)-benzyl]-thiazol-2-yl}-3-hydroxy-7-morpholin-4-yl-pyrido[1,2-a]pyrimidin-4-one;

-continued

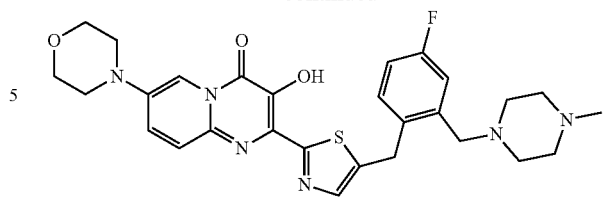

2-{5-[4-Fluoro-2-(4-methyl-piperazin-1-ylmethyl)-benzyl]-thiazol-2-yl}-3-hydroxy-7-morpholin-4-yl-pyrido[1,2-a]pyrimidin-4-one;

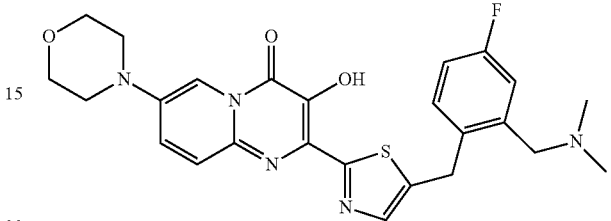

2-[5-(2-Dimethylaminomethyl-4-fluoro-benzyl)-thiazol-2-yl]-3-hydroxy-7-morpholin-4-yl-pyrido[1,2-a]pyrimidin-4-one;

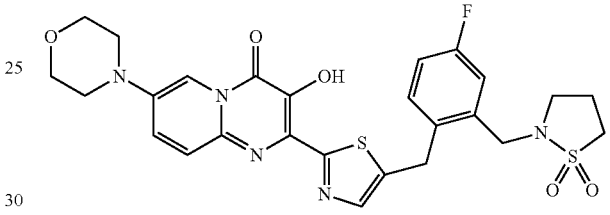

2-{5-[2-(1,1-Dioxo-1lambda*6*-isothiazolidin-2-ylmethyl)-thiazol-2-yl}-3-hydroxy-7-morpholin-4-yl-pyridol[1,2-a]pyrimidin-4-one;

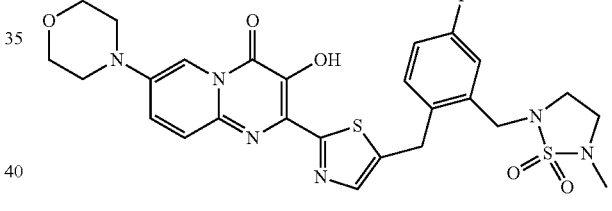

2-{5-[4-Fluoro-2-(5-methyl-1,1-dioxo-1lambda*6*[1,2,5]thiadiazolidin-2-yl)-benzyl]-thiazol-2-yl}-3-hydroxy-7-morpholin-4-yl-pyrido[1,2-a]pyrimidin-4-one;

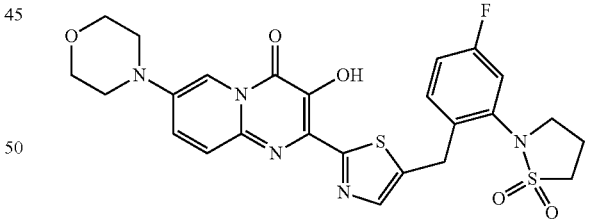

2-{5-[2(1,1-Dioxo-1lambda*6*isothiazolidin-2-yl)-4-fluoro-benzyl]thiazol-2-yl}-3-hydroxy-7-morpholin-4-yl-pyrido[1,2-a]pyrimidin-4-one;

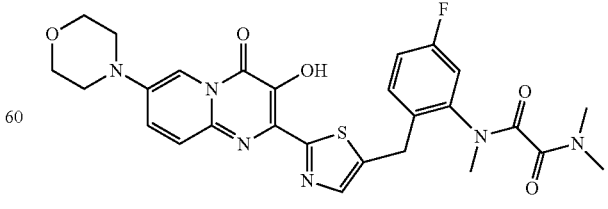

N-{5-Fluoro-2-[2-(3-hydroxy-7-morpholin-4-yl-4-oxo-4H-pyrido[1,2-a]pyrimidin-2-yl)-thiazol-5-ylmethyl]-phenyl}-N,N',N'-trimethyl-oxalamide;

-continued

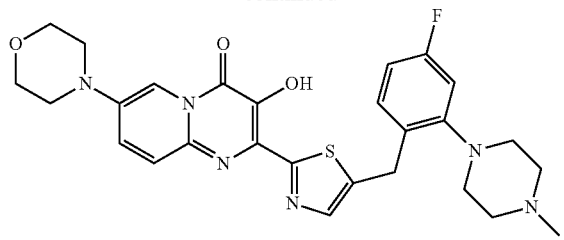

2-{5-[4-Fluoro-2-(4-methyl-piperazin-1-yl)-benzyl]-thiazol-2-yl}-3-hydroxy-7-morpholin-4-yl-pyrido[1,2-a]pyrimidin-4-one;

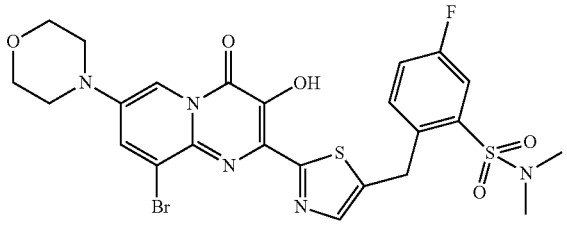

2-[2-(9-Bromo-3-hydroxy-7-morpholin-4-yl-4-oxo-4H-pyrido[1,2-a]pyrimidin-2-yl)-thiazol-5-ylmethyl]-5-fluoro-N,N-dimethyl-benzenesulfonamide;

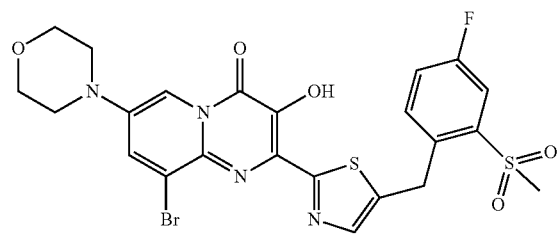

9-Bromo-2-[5-(4-fluoro-2-methanesulfonyl-benzyl)-thiazol-2-yl]-3-hydroxy-7-morpholin-4-yl-pyrido[1,2-a]pyrimidin-4-one;

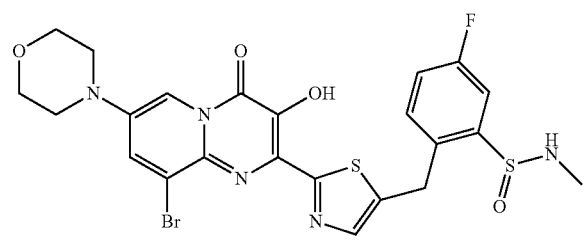

2-[2-(9-Bromo-3-hydroxy-7-morpholin-4-yl-4-oxo-4H-pyrido[1,2-a]pyrimidin-2-yl)-thiazol-5-ylmethyl]-5-fluoro-N-methyl-benzamide;

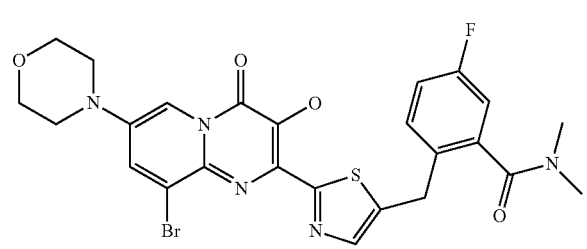

2-[2-(9-Bromo-3-hydroxy-7-morpholin-4-yl-4-oxo-4H-pyrido[1,2-a]pyrimidin-2-yl)-thiazol-5-ylmethyl]-5-fluoro-N,N-dimethyl-benzamide;

-continued

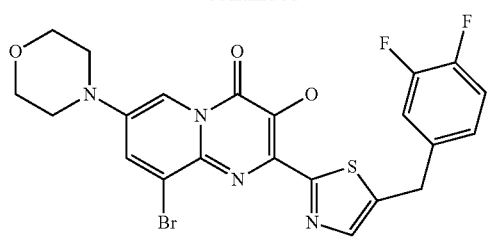

9-Bromo-2-[5-(3,4-difluoro-benzyl)-thiazol-2-yl]-3-hydroxy-7-morpholin-4-yl-pyrido[1,2-a]pyrimidin-4-one;

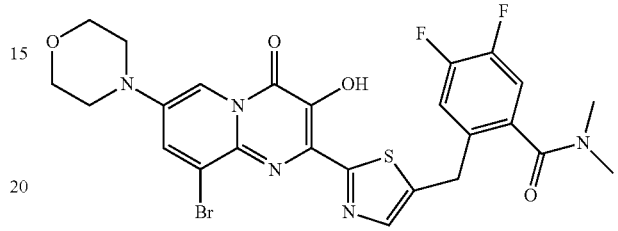

2-[2-(9-Bromo-3-hydroxy-7-morpholin-4-yl-4-oxo-4H-pyrido[1,2-a]pyrimidin-2-yl)-thiazol-5-ylmethyl]-4,5-difluoro-N,N-dimethyl-benzamide;

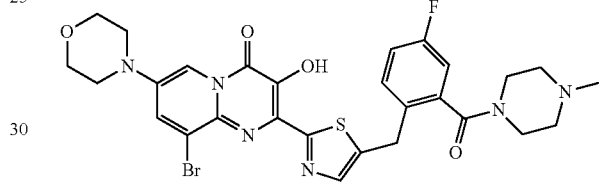

9-Bromo-2-{5-[4-fluoro-2-(4-methyl-piperazine-1-carbonyl)-benzyl]-thiazol-2-yl}-3-hydroxy-7-morpholin-4-yl-pyrido[1,2-a]pyrimidin-4-one;

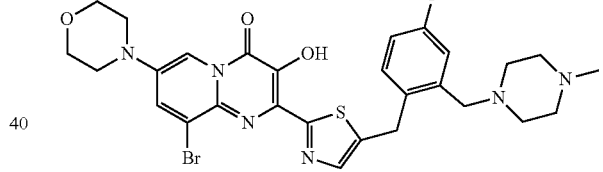

9-Bromo-2-{5-[4-fluoro-2-(4-methyl-piperazin-1-ylmethyl)-benzyl]-thiazol-2-yl}-3-hydroxy-7-morpholin-4-yl-pyrido[1,2-a]pyrimidin-4-one;

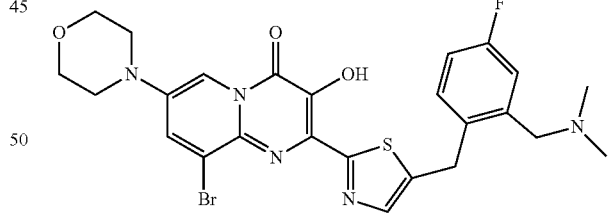

9-Bromo-2-[5-(2-dimethylaminomethyl-4-fluoro-benzyl)-thiazol-2-yl]-3-hydroxy-7-morpholin-4-yl-pyrido[1,2-a]pyrimidin-4-one;

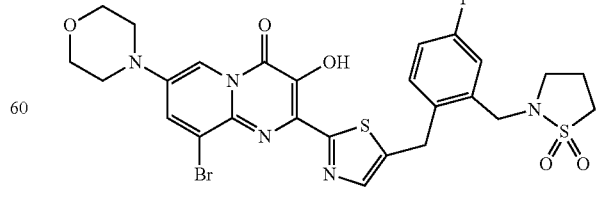

9-Bromo-2-{5-[2-{5-[2-(1,1-dioxo-1lambda*6*-isothiazolidin-2-ylmethyl)-4-fluoro-benzyl]-thiazol-2-yl}3-hydroxy-7-morpholin-4-yl-pyrido[1,2-a]pyrimidin-4-one;

-continued

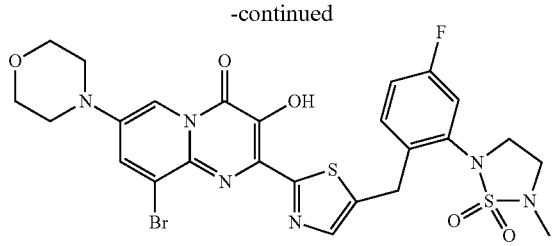

9-Bromo-2-{5-[4-fluoro-2-(5-methyl-1,1-dioxo-1lambda*6*-[1,2,5]thiadiazolidin-2-yl)-benzyl]-thiazol-2-yl}3-hydroxy-7-morpholin-4-yl-pyrido{1,2-a]pyrimidin-4-one;

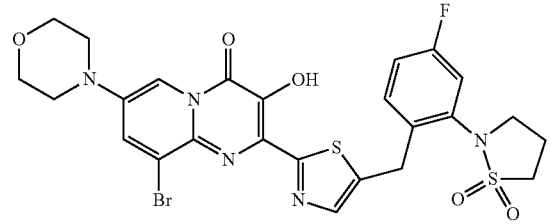

9-Bromo-2-{5-[ 2-(1,1-dioxo-1lambda*6*-isothiazolidin-2-yl)-4-fluoro-benzyl]-thiazol-2-yl}-3-hydroxy-7-morpholin-4-yl-pyrido{1,2-a]pyrimidin-4-one;

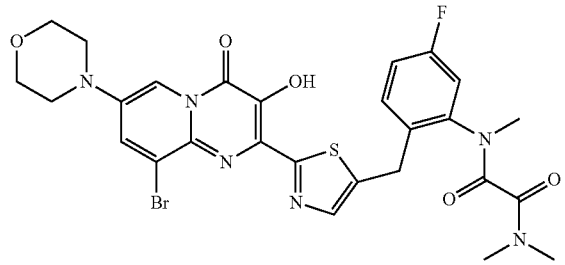

N-(2-[2-(9-Bromo-3-hydroxy-7-morpholin-4-yl-4-oxo-4H-pyrido[1,2-a]pyrimidin-2-yl)-thiazol-5-ylmethyl]-5-fluoro-phenyl}-N,N',N'-trimethyl-oxalamide;

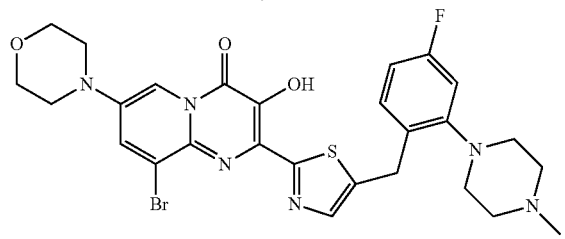

9-Bromo-2-{5-[ 4-fluoro-2-(4-methyl-piperizan-1-yl)-benzyl]-thiazol-2-yl}-3-hydroxy-7-morpholin-4-yl-pyrido{1,2-a]pyrimidin-4-one.

8. A method of reducing viral load and/or inhibiting replication of a virus in a viral infection in a subject, comprising administering to said subject an effective amount of a compound according to claim 1 or a pharmaceutically acceptable salt or prodrug thereof, wherein the viral infection is a HIV infection.

9. The method according to claim 8 wherein the HIV infection comprises a viral strain resistant to other integrase inhibitors.

10. The method according to claim 9 wherein the viral strain comprises HIV integrase enzyme containing the Q148H/G140S double mutation, N155H/E92Q double mutation, the F121Y/T124K double mutation or the Q148K/G140A/E138A triple mutation.

11. A pharmaceutical composition comprising a compound according to claim 1 and a pharmaceutically acceptable carrier, diluent or excipient.

12. A compound according to claim 1 having the structure

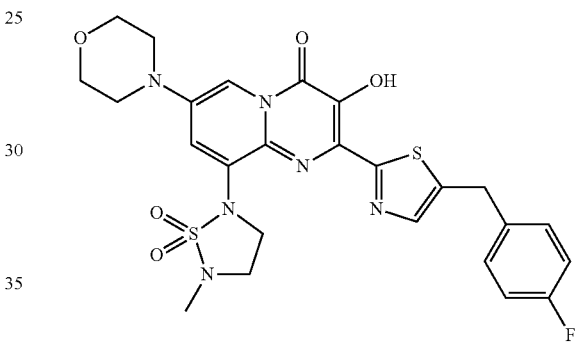

2-[5-(4-Flouro-benzyl)-thiazol-2-yl]-3-hydroxy-9-(5-methyl-1,1-dioxo-1l6-[1,2,5]thiadiazolidin-2-yl)-7-morpholin-4-yl-pyrido[1,2-a]pyrimidin-4-one.

13. The method according to claim 9 wherein the integrase inhibitors are Isentrass (raltregavir, MK-0158) or elvitegravir.

* * * * *

UNITED STATES PATENT AND TRADEMARK OFFICE
CERTIFICATE OF CORRECTION

PATENT NO.        : 8,318,732 B2
APPLICATION NO.   : 12/734036
DATED             : November 27, 2012
INVENTOR(S)       : Deadman et al.

Page 1 of 1

It is certified that error appears in the above-identified patent and that said Letters Patent is hereby corrected as shown below:

On the Title Page

Item [75], please add the following missing inventors:

--Giang Thanh Le (Victoria, AU), Neeranat Thien-Thong (Victoria, AU) and Lisa Jane Winfield (Norfolk, UK)--

Signed and Sealed this
Seventh Day of January, 2014

Margaret A. Focarino
*Commissioner for Patents of the United States Patent and Trademark Office*

UNITED STATES PATENT AND TRADEMARK OFFICE
CERTIFICATE OF CORRECTION

PATENT NO. : 8,318,732 B2
APPLICATION NO. : 12/734036
DATED : November 27, 2012
INVENTOR(S) : John Joseph Deadman et al.

It is certified that error appears in the above-identified patent and that said Letters Patent is hereby corrected as shown below:

Title Page,
Item [75], Inventors, "Giang Thanh Le, Victoria (AU); Neeranat Thien-Thong, Victoria (AU); Lisa Jane Winfield, Norfolk (UK)" (as added in Certificate of Correction issued January 7, 2014) are deleted and patent is returned to its original state with inventorship in patent to read -- John Joseph Deadman, Carlton (AU); Eric Dale Jones, Bentleigh East (AU); David Ian Rhodes, Heidelberg Heights (AU); Nicholas Andrew Van de Graff, Prahran (AU) --.

Signed and Sealed this
Twenty-ninth Day of April, 2014

Michelle K. Lee
*Deputy Director of the United States Patent and Trademark Office*